(12) United States Patent
Boehm et al.

(10) Patent No.: US 7,807,782 B2
(45) Date of Patent: Oct. 5, 2010

(54) METHOD FOR LINKING MOLECULAR SUBSTANCES

(75) Inventors: Gerald Boehm, Halle (DE); Ulrich Schmidt, West Leederville (AU); Christoph Parthier, Halle (DE); Constanze Guenther, Halle (DE)

(73) Assignee: ACGT ProGenomics (DE)

( * ) Notice: Subject to any disclaimer, the term of this patent is extended or adjusted under 35 U.S.C. 154(b) by 264 days.

(21) Appl. No.: 11/446,587

(22) Filed: Jun. 1, 2006

(65) Prior Publication Data

US 2006/0252130 A1 Nov. 9, 2006

Related U.S. Application Data

(63) Continuation of application No. 10/129,315, filed as application No. PCT/EP00/10873 on Nov. 3, 2000, now abandoned.

(30) Foreign Application Priority Data

Nov. 3, 1999 (DE) ................................ 199 52 956

(51) Int. Cl.
   *C07K 1/00* (2006.01)
   *C07K 1/22* (2006.01)
   *C07K 1/113* (2006.01)
(52) U.S. Cl. ........................ 530/333; 530/339; 530/345
(58) Field of Classification Search ....................... None
   See application file for complete search history.

(56) References Cited

U.S. PATENT DOCUMENTS 6,503,703 B1 * 1/2003 Palese et al. ................... 435/5

FOREIGN PATENT DOCUMENTS

EP 0511747 A1 11/1992

OTHER PUBLICATIONS

Sparks et al (Methods in Enzymology, 1995, vol. 255, pp. 498-509).*
Bedford, Mark T. et al.; "WW domain-mediated interactions reveal a spliceosome-associated protein that binds a third class of praline-rich motif: The praline glycine and methionine-rich motif"; 1998, *Proc. Natl. Acad. Sci.*, vol. 95, pp. 10602-10607.
Ermekova, Kira S. et al., "The WW Domain of Neural Protein FE65 Interacts with Proline-rich Motifs in Mena, the Mammalian Homolog of *Drosophila* Enabled"; 1997, *The Journal of Biological Chemistry*, vol. 272, No. 52, pp. 32868-32877.
Schmidt, Thomas G.M. et al., "Molecular Interaction Between the *Strep*-tag Affinity Peptide and its Cognate Target, Streptavidin"; 1996, *J. Mol. Biol.*, vol. 255, pp. 753-766.
Baraldi, E. et al.; "Spectroscopical Studies on the Interaction Between WW Domain and Proline-rich Peptides"; *NATO ASI Series*; 1997; pp. 45-48; vol. H102.
Crane, Jason C., et al.; "Mapping the Transition State of the WW Domain β-Sheet"; *Journal of Molecular Biology*; 2000; pp. 283-292; vol. 298.
Einbond, A. and Sudol, M.; "Towards Prediction of Cognate Complexes Between the WW Domain and Proline-rich Ligands"; *FEBS Letters*; 1996; pp. 1-8; vol. 384.
Harty, R.N. et al.; "A Proline-rich Motif within the Matrix Protein of Vesicular Stomatitis Virus and Rabies Virus Interacts with WW Domains of Cellular Proteins: Implications for Viral Budding"; *J. of Virology*; Apr. 1999; pp. 2921-2929; vol. 73, No. 4.
Hoffmüller, U. et al. "Mapping and Characterization of Epitopes Recognized by WW Domains Using Cellulose-bound Peptide Libraries"; *Peptides: Frontiers of Peptide Science. Proceedings of the 15th American Peptide Symposium.*; Jun. 14-19, 1997; Nashville, Tennessee, U.S.A; Tam, J.P. and Kaumaya, P.T.P., eds. Kluwer Academic Publishers, Dordrecht, The Netherlands, pp. 551-552.
Ibragimova, Gulshat T. and Rebecca C. Wade; "Stability of the β-Sheet of the WW Domain: A Molecular Dynamics Simulation Study"; *Biophysical Journal*; Oct. 1999; pp. 2191-2198; vol. 77.
Kanamuru, Shuji, et al.; "Structure of the cell-puncturing device of bacteriophage T4"; *Nature*; Jan. 21, 2002; pp. 553-557; vol. 415.
Koepf, Edward K., et al.; "Characterization of the Structure and Function of W→F WW Domain Variants: Identification of a Natively Unfolded Protein That Folds upon Ligand Binding"; *Biochemistry*; 1999; pp. 14338-14351; vol. 38.
Linn, H. et al.; "Using Molecular Repertoires to Identify High-affinity Peptide Ligands of the WW Domain of Human and Mouse YAP"; *Biol. Chem.*; 1997; pp. 531-537; vol. 378, No. 6.
Nguyen, J.T. et al.; "Exploiting the Basis of Proline Recognition by SH3 and WW Domains: Design of N-Substituted Inhibitors"; *Science*; Dec. 1998; pp. 2088-2092; vol. 282.
Plank, Christian, et al.; "The Influence of Endosome-disruptive Peptides on Gene Transfer Using Synthetic Virus-Like Gene Transfer Systems"; *Journal of Biological Chemistry*; 1994; pp. 12918-12924; vol. 269.
Schmidt, U. et al.; "Stringent Purification of Recombinant Proteins Using WW Polyproline Affinity Chromatography"; *Int. J. Bio-Chromatogr.*; 2001; pp. 79-85; vol. 6, No. 1.
Schmidt, Uli, et al.; Protein and peptide delivery via engineered polyomavirus-like particles; *The Journal of Biological Chemistry*; 2001; pp. 1646-1648; vol. 15; FASEB.
Sharma, Pranav, et al.; "Endocytosis of lipid rafts: an identity crisis"; *Seminars in Cell and Developmental Biology*; 2002; pp. 205-214; vol. 13.

\* cited by examiner

*Primary Examiner*—Karen A Canella
(74) *Attorney, Agent, or Firm*—Townsend and Townsend and Crew LLP.; M. Henry Heines

(57) ABSTRACT

The invention relates to a method for linking two or more molecular substances, by means of adapter segments, which bring about a targeted interaction based upon the affinity of proline-rich amino acid sequences and protein domains of the type WW.

5 Claims, 19 Drawing Sheets

(a)
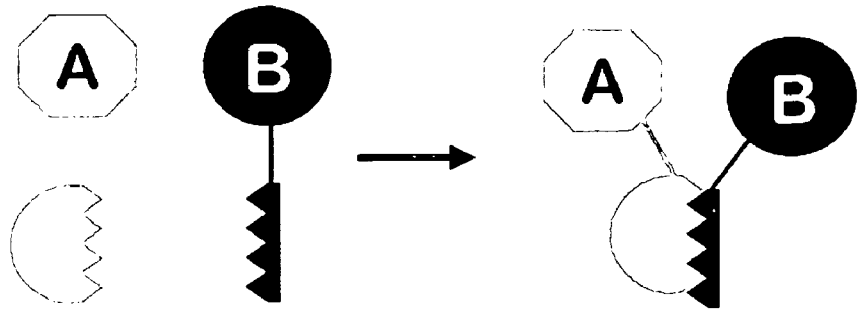
(b)
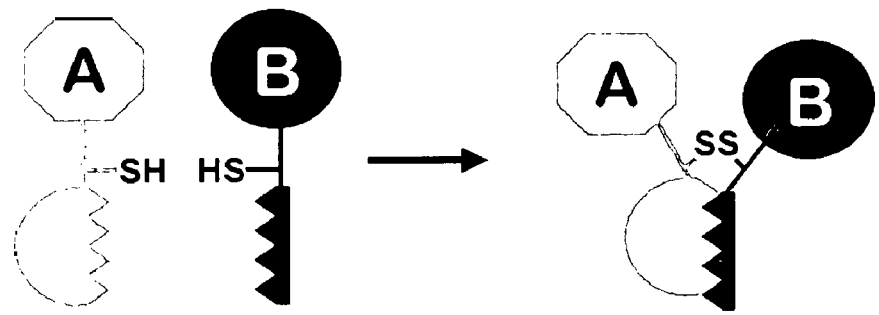
(c)
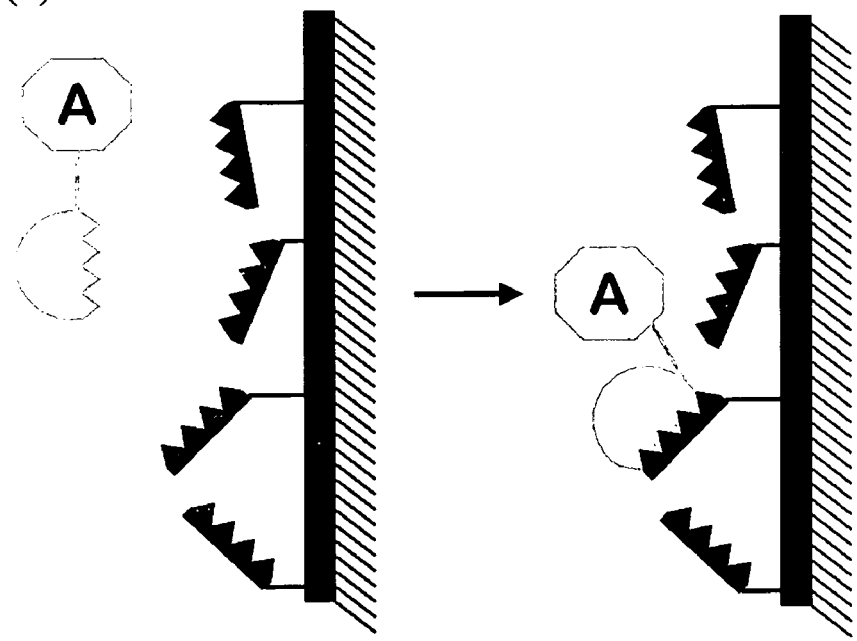
Figure 1. Schematic representation of the invention.

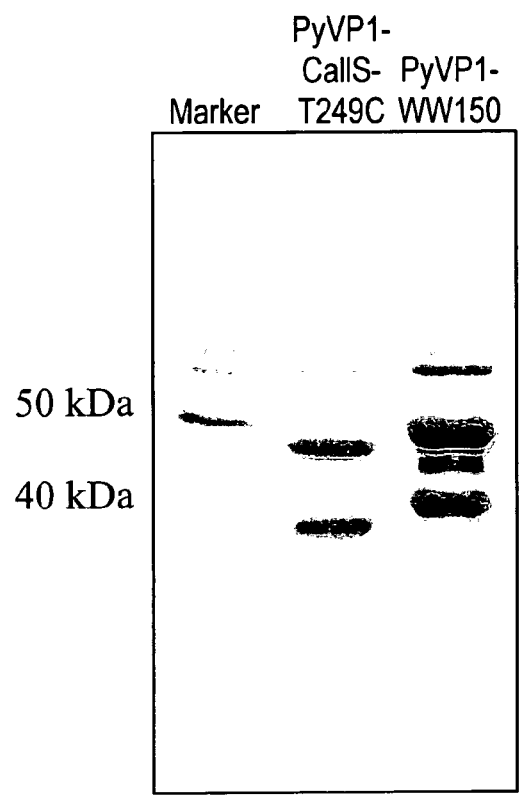
Figure 2a. Variants of polyomavirus VP1, separation in an SDS gel.

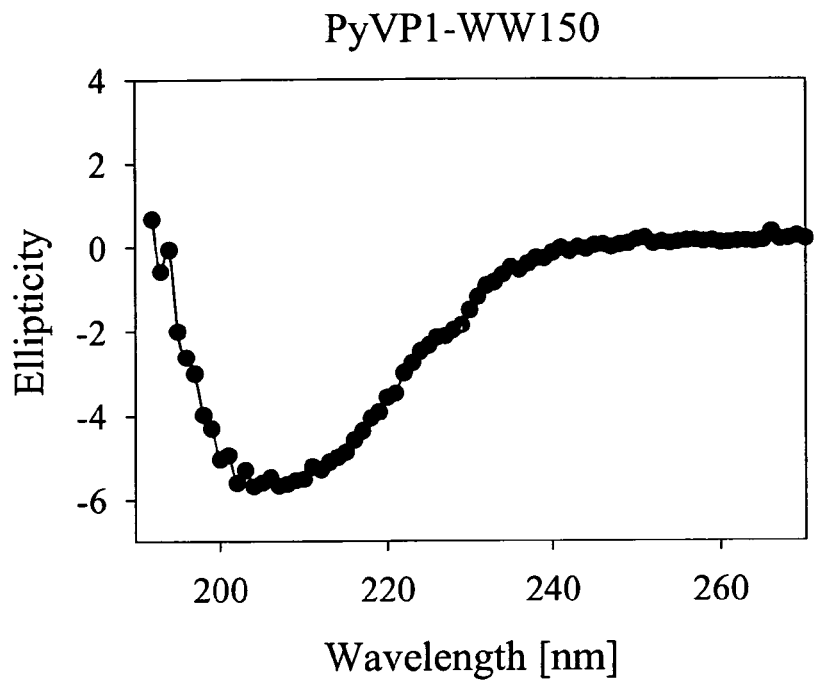
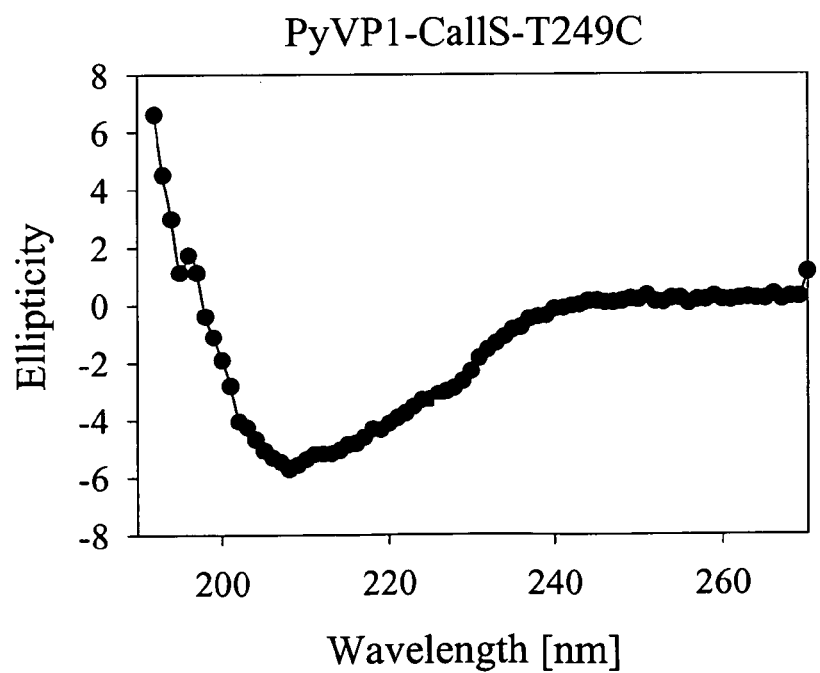
Figure 2b. Variants of polyomavirus VP1, near-UV CD spectra.

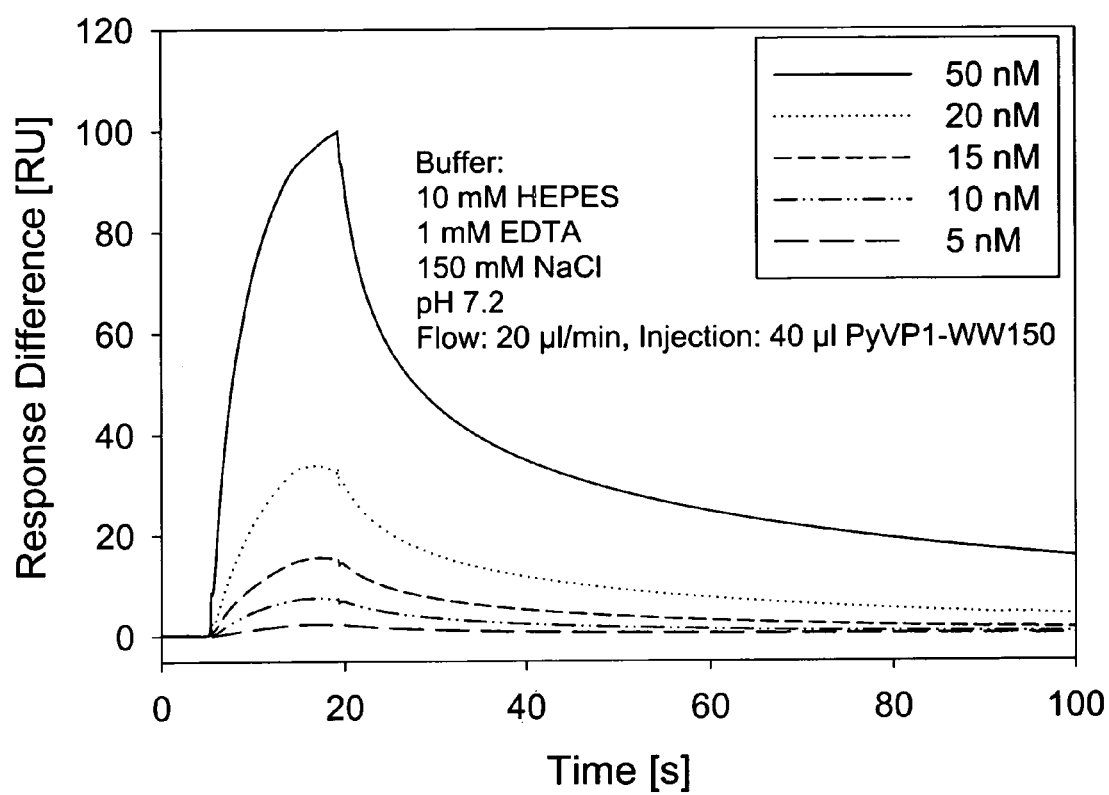
Figure 3a: Binding of PyVP1-WW150 onto a sensor chip.

Figure 3b: Binding of PyVP1-WW150 (in Dulbecco's PBS) onto a sensor chip.

Figure 3c. Binding of PyVP1-WW150 (in Dulbecco's MEM + 10% FCS) onto a sensor chip.

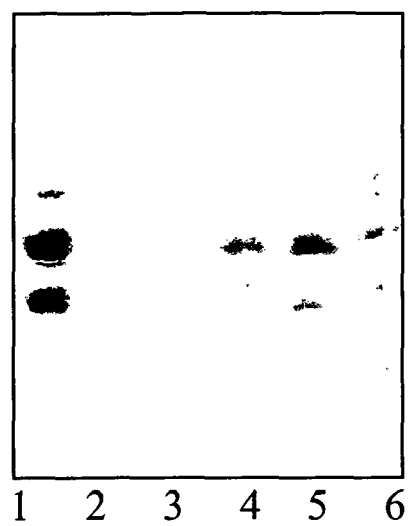
Figure 4. SDS gel for the representation of the specific binding.

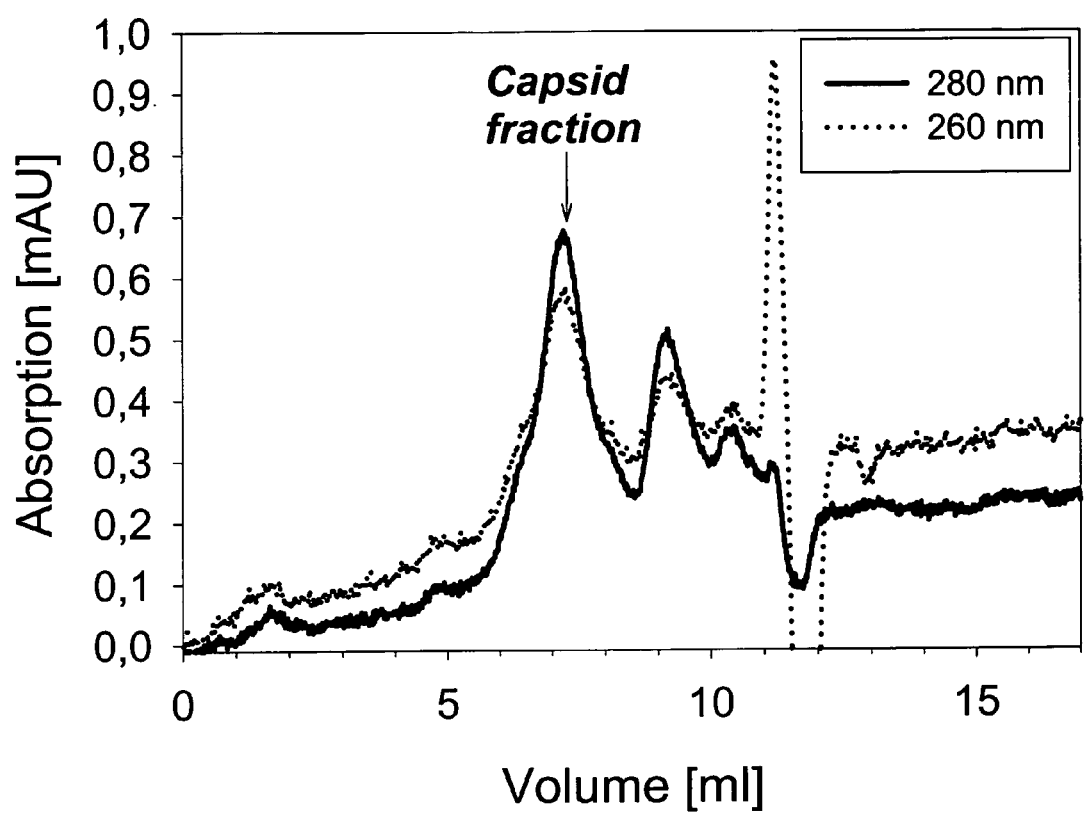
Figure 5a: Gel filtration.

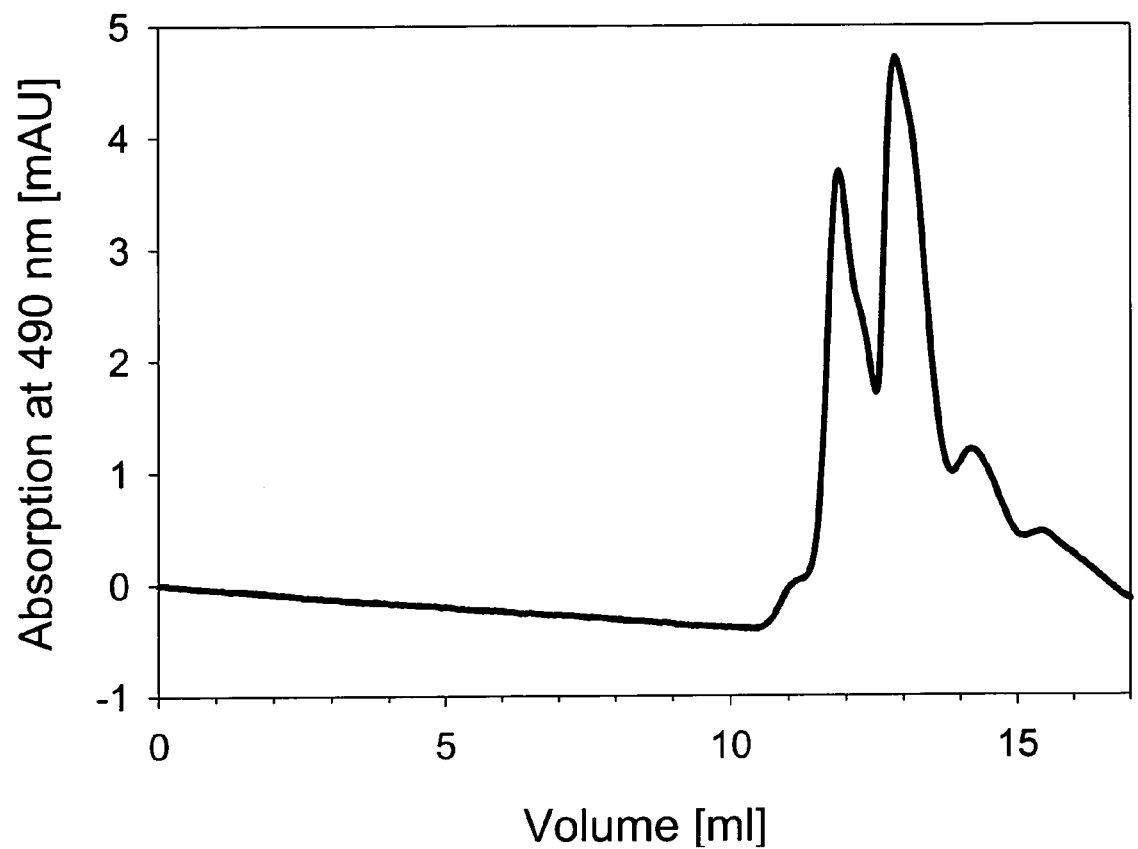
Figure 5b: Gel filtration.

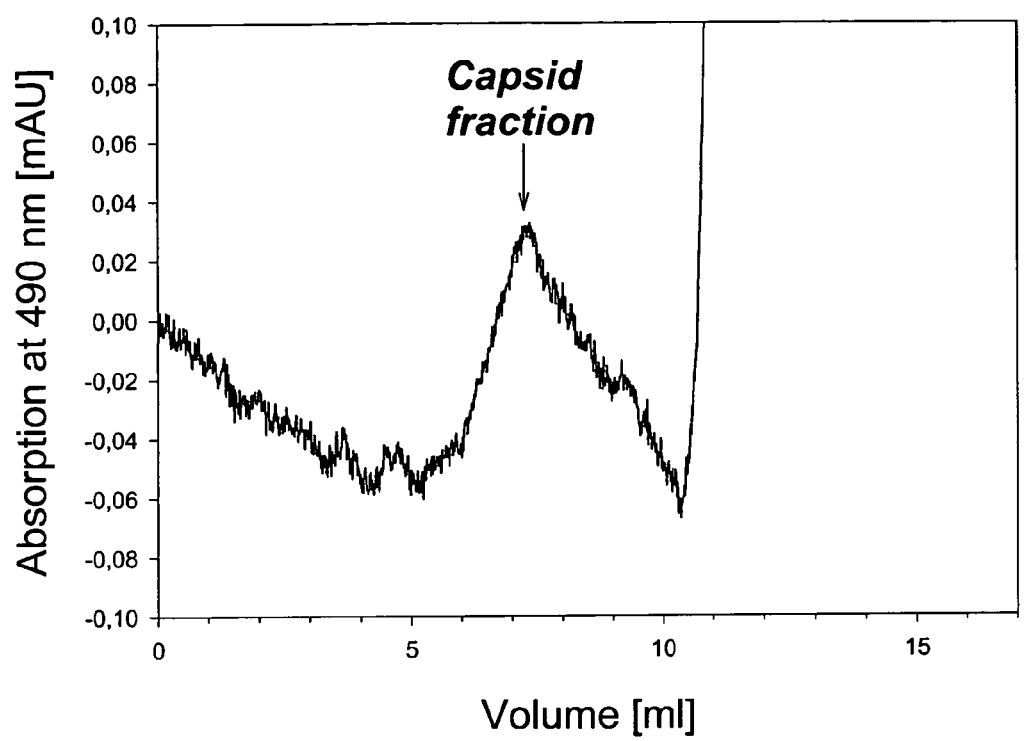
Figure 5c: Gel filtration.

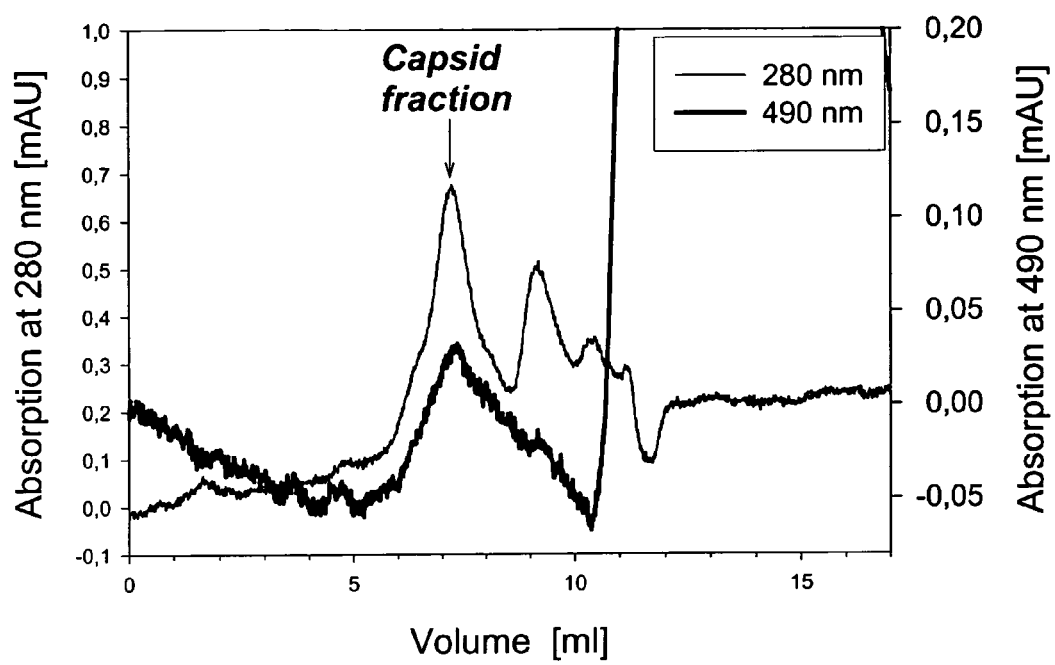
Figure 5d. Gel filtration.

(a)
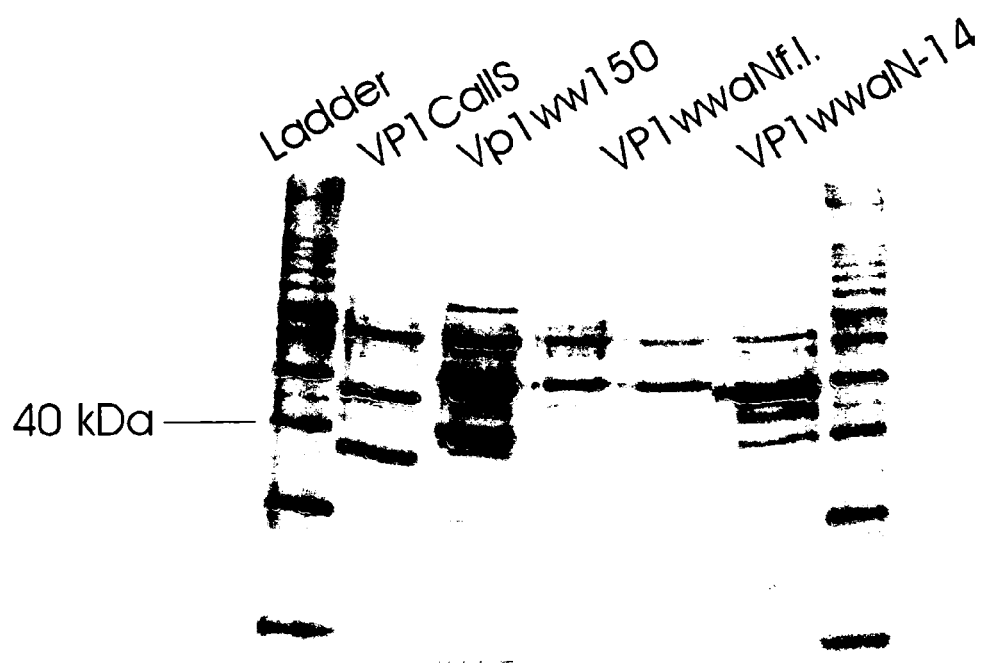
(b)
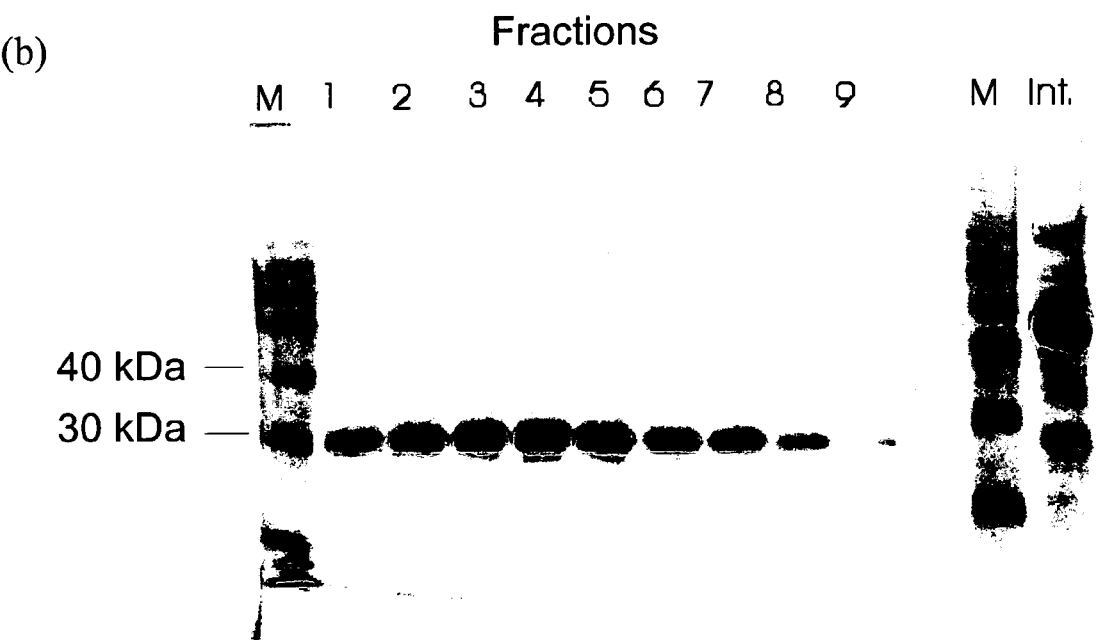
Figure 6. Variants.

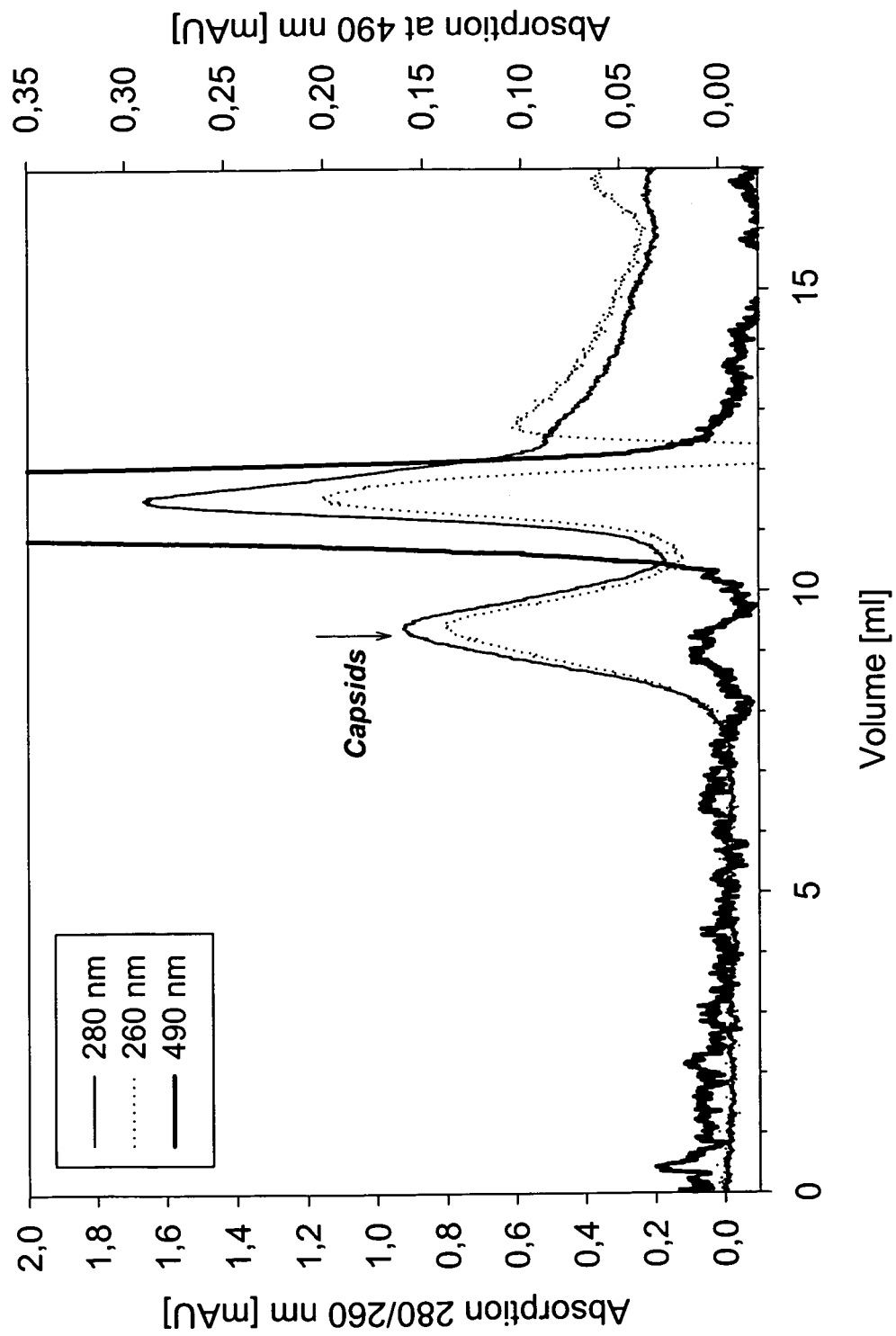
Figure 7a: Packaging.

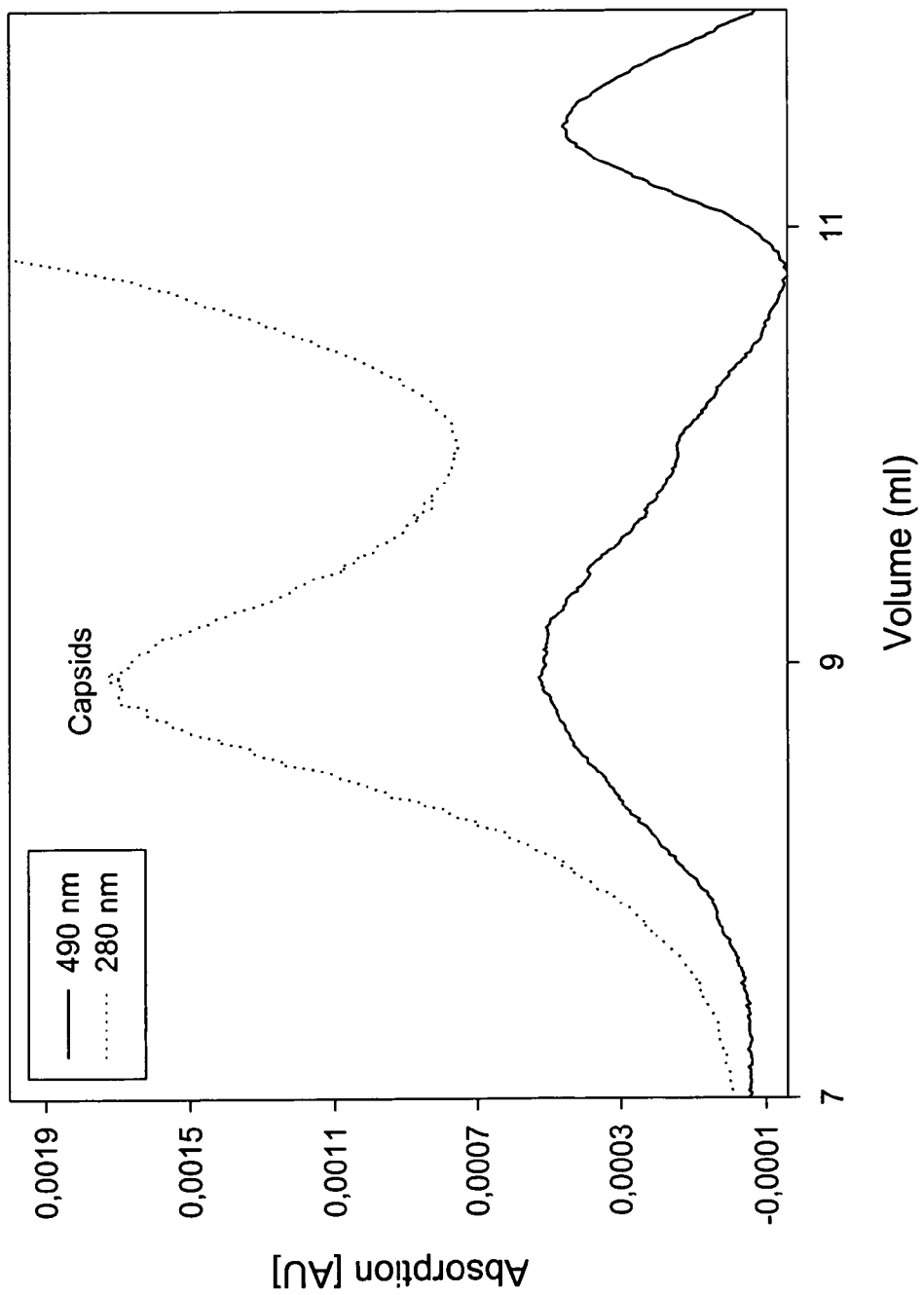
Figure 7b: Packaging.

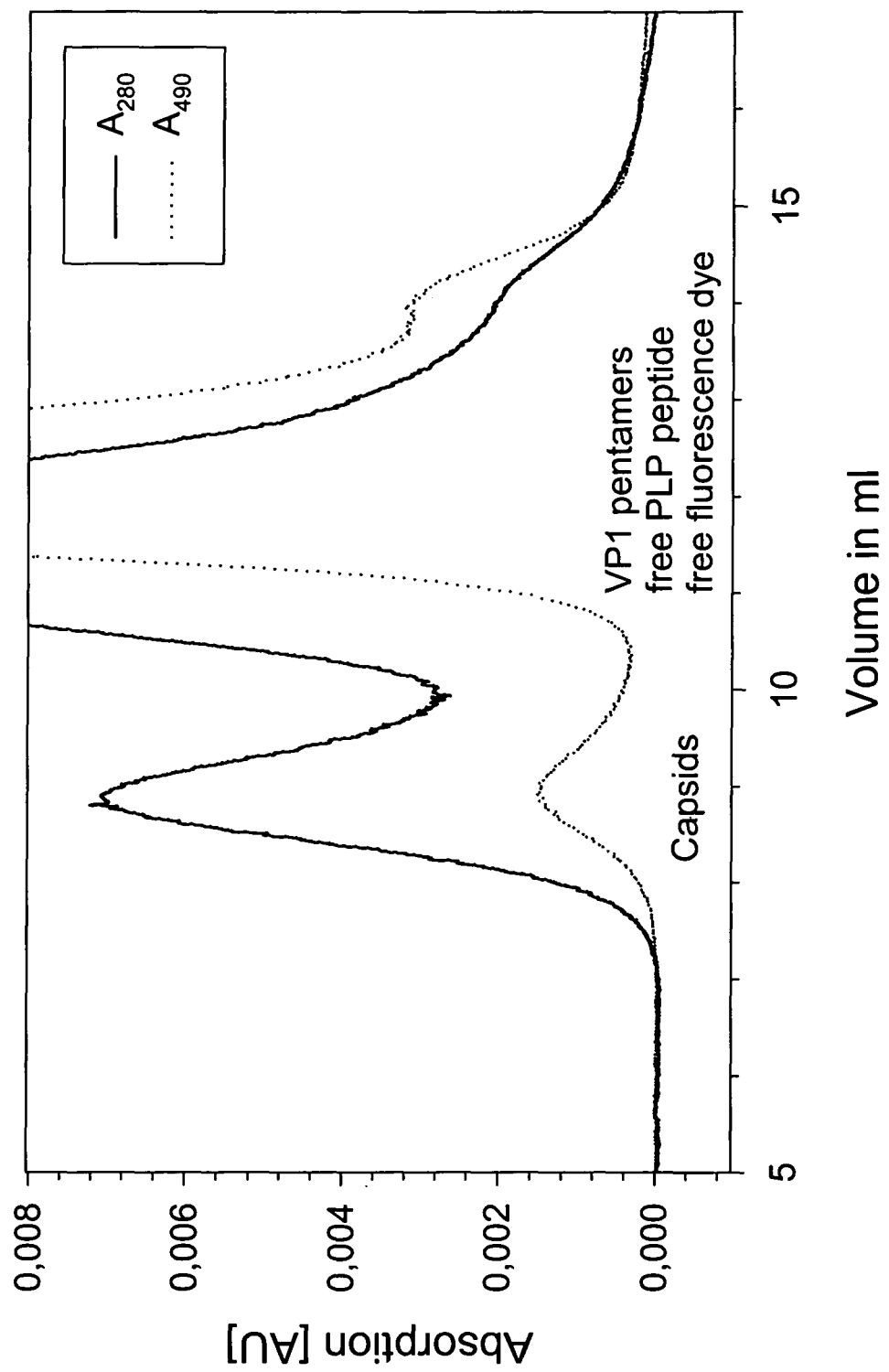
Figure 7c: Packaging.

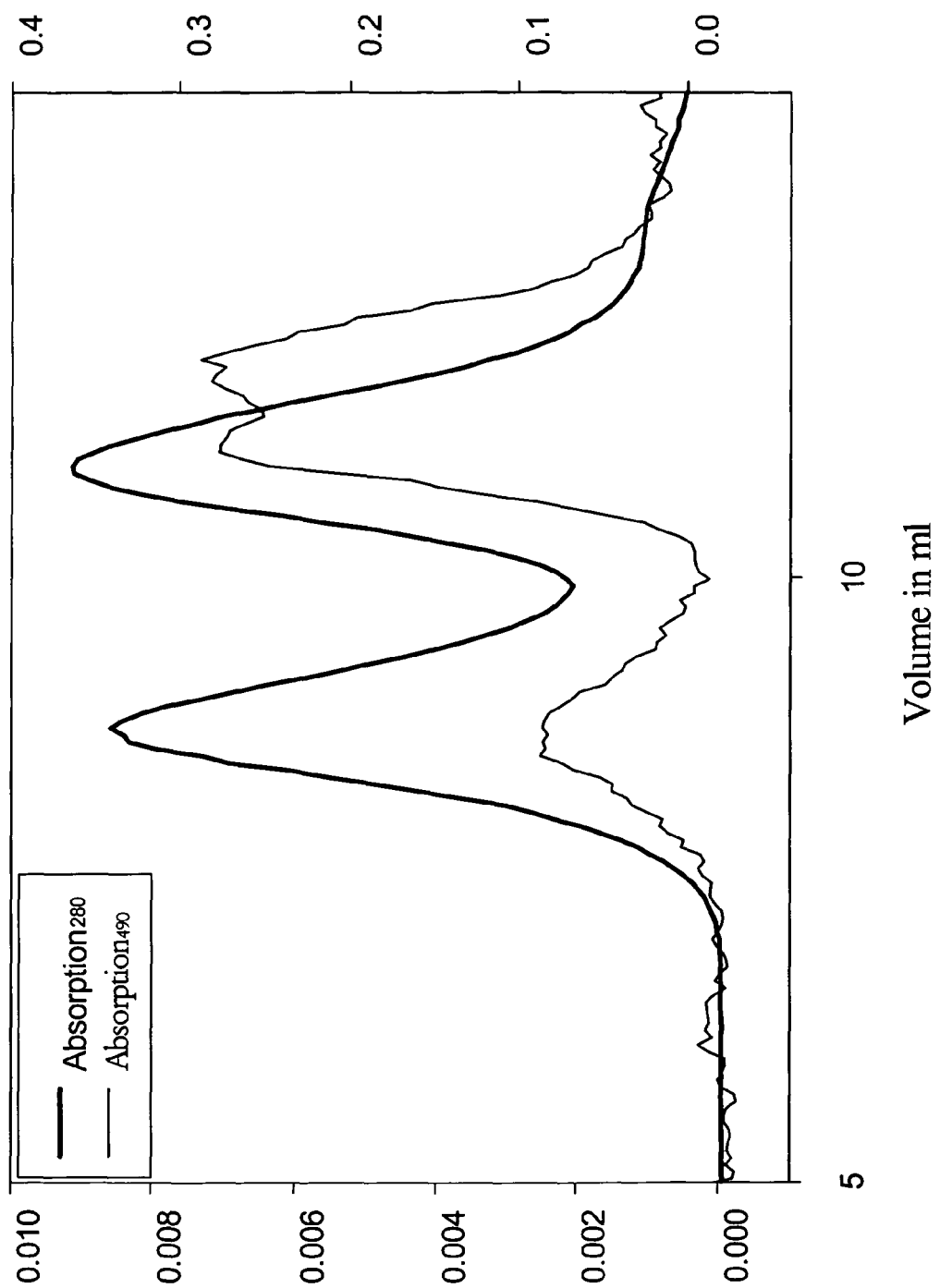
Figure 7d: Packaging.

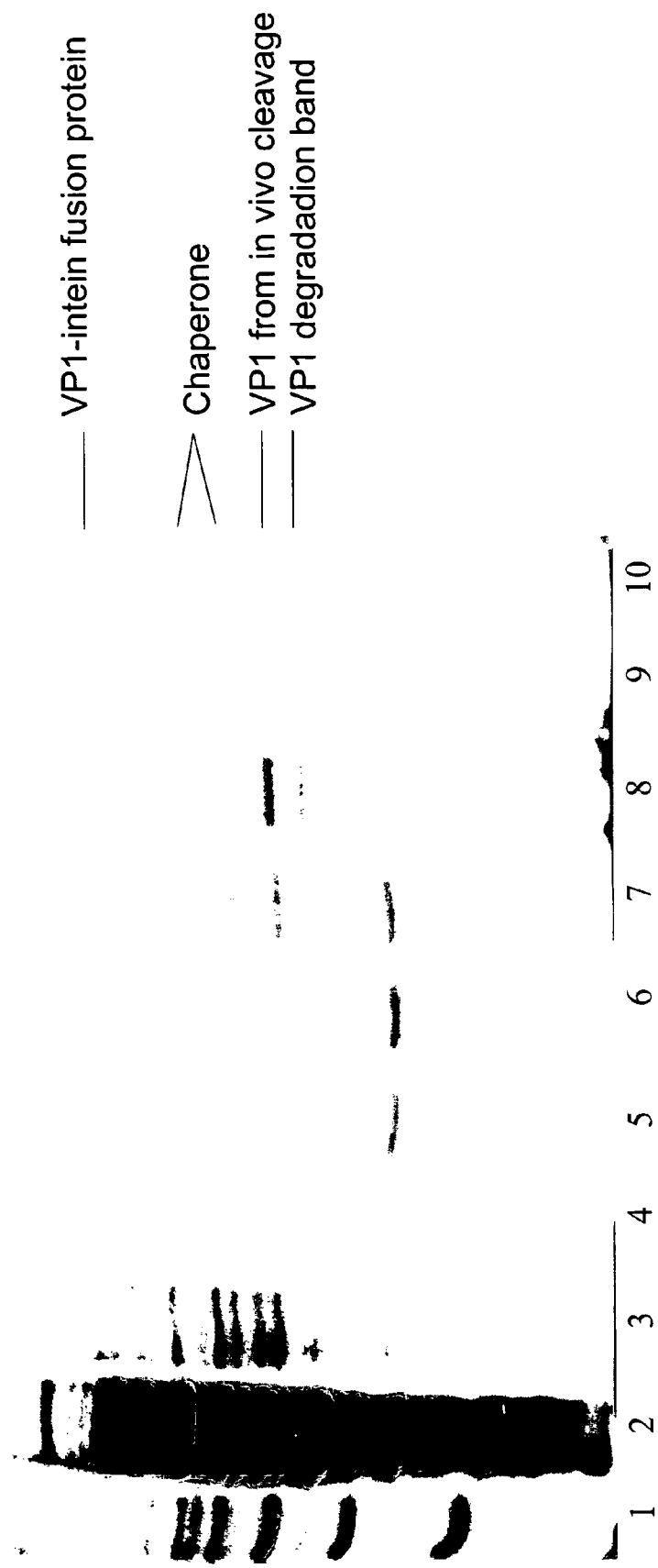
Figure 8. SDS gel.

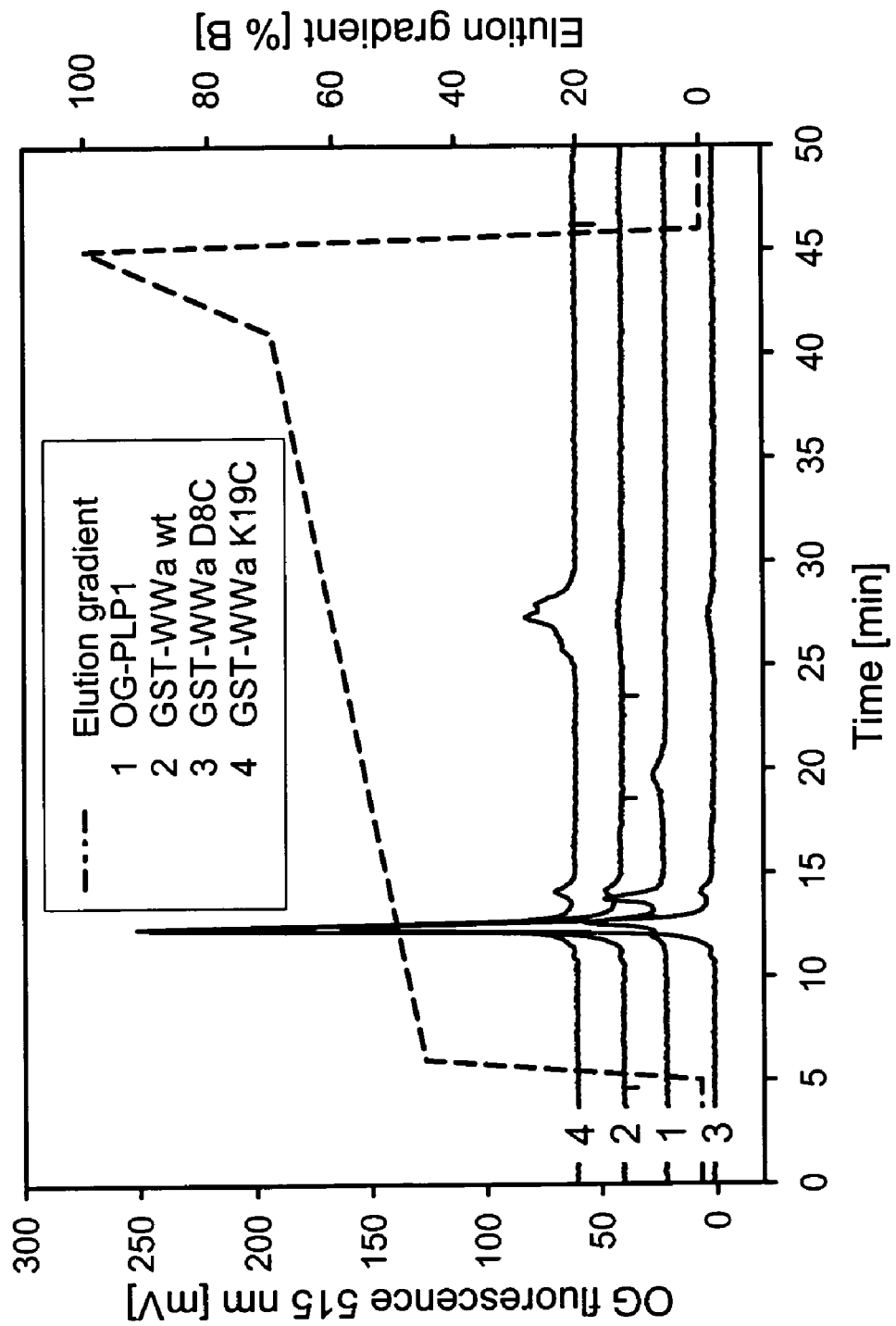
Figure 9a. HPLC analysis of the disulfide bridging.

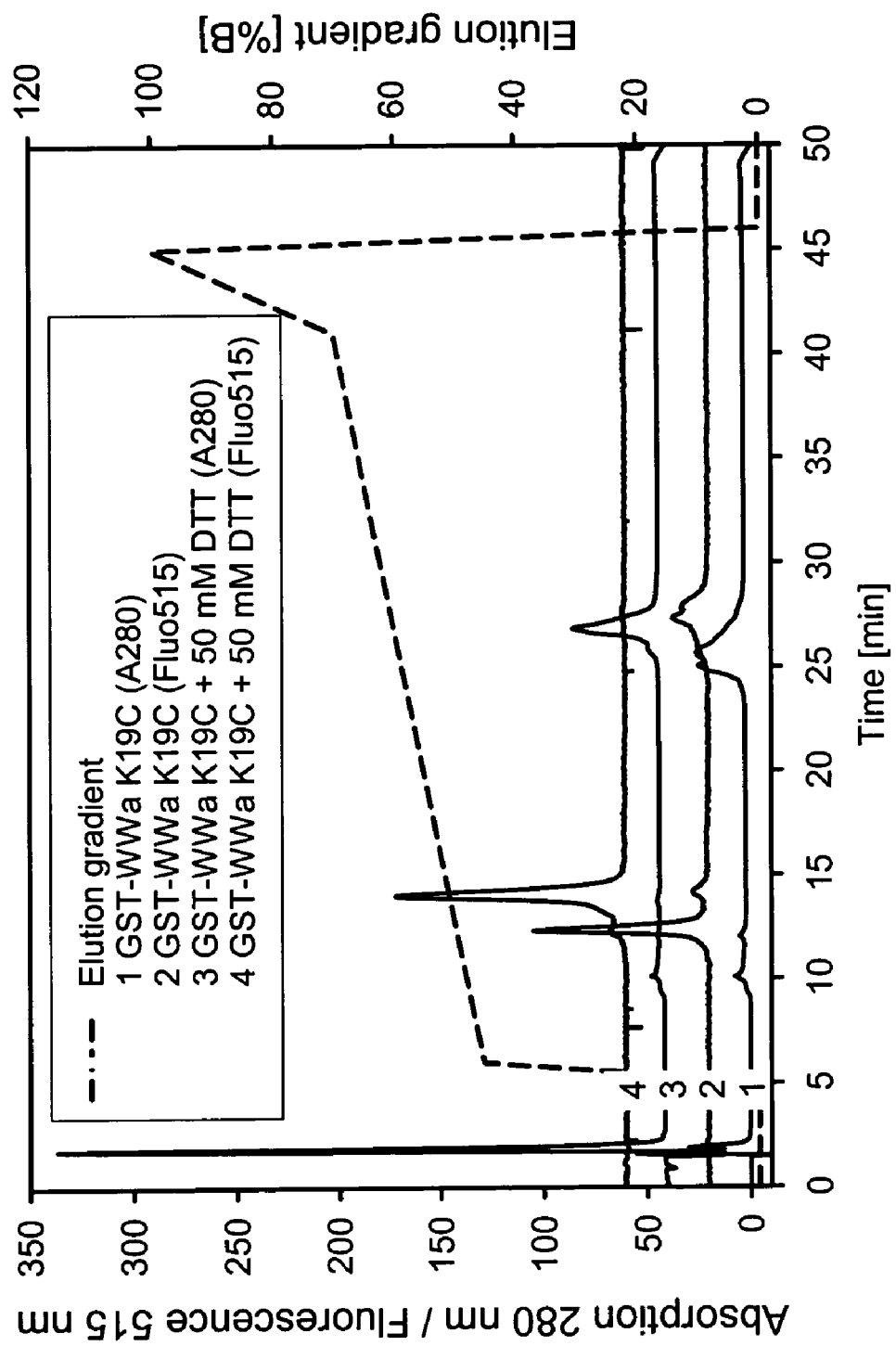
Figure 9b. HPLC analysis of the disulfide bridging.

SEQUENCE LISTING

```
<160> NUMBER OF SEQ ID NOS: 38

<210> SEQ ID NO 1
<211> LENGTH: 1266
<212> TYPE: DNA
<213> ORGANISM: Artificial Sequence
<220> FEATURE:
<223> OTHER INFORMATION: Description of Artificial Sequence:cysteine
      variant of VP1-WW150 with amino acid exchange D8C
      at position 8 of the WW domain (PyVP1-WW150-D8C)
<220> FEATURE:
<221> NAME/KEY: CDS
<222> LOCATION: (1)..(1266)
<223> OTHER INFORMATION: PyVP1-WW150-D8C
<220> FEATURE:
<221> NAME/KEY: misc_feature
<222> LOCATION: (445)..(558)
<223> OTHER INFORMATION: inserted WW domain (WW150)
<220> FEATURE:
<221> NAME/KEY: misc_feature
<222> LOCATION: (481)..(483)
<223> OTHER INFORMATION: inserted Cys in WW domain (WW150)

<400> SEQUENCE: 1 atg gcc ccc aaa aga aaa agc ggc gtc tct aaa agc gag aca aaa agc      48
Met Ala Pro Lys Arg Lys Ser Gly Val Ser Lys Ser Glu Thr Lys Ser
 1               5                  10                  15
```

-continued

| | | |
|---|---|---|
| aca aag gct agc cca aga ccc gca ccc gtt ccc aaa ctg ctt att aaa<br>Thr Lys Ala Ser Pro Arg Pro Ala Pro Val Pro Lys Leu Leu Ile Lys<br>20 25 30 | 96 |
| ggg ggt atg gag gtg ctg gac ctt gtg aca ggg cca gac agt gtg aca<br>Gly Gly Met Glu Val Leu Asp Leu Val Thr Gly Pro Asp Ser Val Thr<br>35 40 45 | 144 |
| gaa ata gaa gct ttt ctg aac ccc aga atg ggg cag cca ccc acc cct<br>Glu Ile Glu Ala Phe Leu Asn Pro Arg Met Gly Gln Pro Pro Thr Pro<br>50 55 60 | 192 |
| gaa agc cta aca gag gga ggg caa tac tat ggt tgg agc aga ggg att<br>Glu Ser Leu Thr Glu Gly Gly Gln Tyr Tyr Gly Trp Ser Arg Gly Ile<br>65 70 75 80 | 240 |
| aat ttg gct aca tca gat aca gag gat tcc cca gga aat aat aca ctt<br>Asn Leu Ala Thr Ser Asp Thr Glu Asp Ser Pro Gly Asn Asn Thr Leu<br>85 90 95 | 288 |
| ccc aca tgg agt atg gca aag ctc cag ctt ccc atg ctc aat gag gac<br>Pro Thr Trp Ser Met Ala Lys Leu Gln Leu Pro Met Leu Asn Glu Asp<br>100 105 110 | 336 |
| ctc acg tct gac acc cta caa atg tgg gag gca gtc tca gtg aaa acc<br>Leu Thr Ser Asp Thr Leu Gln Met Trp Glu Ala Val Ser Val Lys Thr<br>115 120 125 | 384 |
| gag gtg gtg ggc tct ggc tca ctg tta gat gtg cat ggg ttc aac aaa<br>Glu Val Val Gly Ser Gly Ser Leu Leu Asp Val His Gly Phe Asn Lys<br>130 135 140 | 432 |
| ccc aca gat aca ggc agc ggc agc ggc tgg aca gaa cat aaa tca cct<br>Pro Thr Asp Thr Gly Ser Gly Ser Gly Trp Thr Glu His Lys Ser Pro<br>145 150 155 160 | 480 |
| tgt gga agg act tat tat tac aat act gaa aca aaa cag tct acc tgg<br>Cys Gly Arg Thr Tyr Tyr Tyr Asn Thr Glu Thr Lys Gln Ser Thr Trp<br>165 170 175 | 528 |
| gaa aag cca gat gat ggt agt ggt agc ggc gta aac aca aaa gga att<br>Glu Lys Pro Asp Asp Gly Ser Gly Ser Gly Val Asn Thr Lys Gly Ile<br>180 185 190 | 576 |
| tcc act cca gtg gaa ggc agc caa tat cat gtg ttt gct gtg ggc ggg<br>Ser Thr Pro Val Glu Gly Ser Gln Tyr His Val Phe Ala Val Gly Gly<br>195 200 205 | 624 |
| gaa ccg ctt gac ctc cag gga ctt gtg aca gat gcc aga aca aaa tac<br>Glu Pro Leu Asp Leu Gln Gly Leu Val Thr Asp Ala Arg Thr Lys Tyr<br>210 215 220 | 672 |
| aag gaa gaa ggg gta gta aca atc aaa aca atc aca aag aag gac atg<br>Lys Glu Glu Gly Val Val Thr Ile Lys Thr Ile Thr Lys Lys Asp Met<br>225 230 235 240 | 720 |
| gtc aac aaa gac caa gtc ctg aat cca att agc aag gcc aag ctg gat<br>Val Asn Lys Asp Gln Val Leu Asn Pro Ile Ser Lys Ala Lys Leu Asp<br>245 250 255 | 768 |
| aag gac gga atg tat cca gtt gaa atc tgg cat cca gat cca gca aaa<br>Lys Asp Gly Met Tyr Pro Val Glu Ile Trp His Pro Asp Pro Ala Lys<br>260 265 270 | 816 |
| aat gag aac aca agg tac ttt ggc aat tac act gga ggc acg tgc acc<br>Asn Glu Asn Thr Arg Tyr Phe Gly Asn Tyr Thr Gly Gly Thr Cys Thr<br>275 280 285 | 864 |
| cca ccc gtc ctg cag ttc aca aac acc ctg aca act gtg ctc cta gat<br>Pro Pro Val Leu Gln Phe Thr Asn Thr Leu Thr Thr Val Leu Leu Asp<br>290 295 300 | 912 |
| gaa aat gga gtt ggg ccc ctc agc aaa gga gaa ggt cta tac ctc tcg<br>Glu Asn Gly Val Gly Pro Leu Ser Lys Gly Glu Gly Leu Tyr Leu Ser<br>305 310 315 320 | 960 |
| agc gta gat ata atg ggc tgg aga gtt aca aga aac tat gat gtc cat<br>Ser Val Asp Ile Met Gly Trp Arg Val Thr Arg Asn Tyr Asp Val His<br>325 330 335 | 1008 |

```
cac tgg aga ggg ctt ccc aga tat ttc aaa atc acc ctg aga aaa aga    1056
His Trp Arg Gly Leu Pro Arg Tyr Phe Lys Ile Thr Leu Arg Lys Arg
            340                 345                 350 tgg gtc aaa aat ccc tat ccc atg gcc tcc ctc ata agt tcc ctt ttc    1104
Trp Val Lys Asn Pro Tyr Pro Met Ala Ser Leu Ile Ser Ser Leu Phe
            355                 360                 365 aac aac atg ctc ccc caa gtg cag ggc caa ccc atg gaa ggg gag aac    1152
Asn Asn Met Leu Pro Gln Val Gln Gly Gln Pro Met Glu Gly Glu Asn
    370                 375                 380 acc cag gta gag gag gtt aga gtg tat gat ggg act gaa cct gta ccg    1200
Thr Gln Val Glu Glu Val Arg Val Tyr Asp Gly Thr Glu Pro Val Pro
385                 390                 395                 400 ggg gac cct gat atg acg cgc tat gtt gac cgc ttt gga aaa aca aag    1248
Gly Asp Pro Asp Met Thr Arg Tyr Val Asp Arg Phe Gly Lys Thr Lys
                405                 410                 415 act gta ttt cct ccc ggg                                            1266
Thr Val Phe Pro Pro Gly
            420

<210> SEQ ID NO 2
<211> LENGTH: 422
<212> TYPE: PRT
<213> ORGANISM: Artificial Sequence
<220> FEATURE:
<223> OTHER INFORMATION: Description of Artificial Sequence:cysteine
      variant of VP1-WW150 with amino acid exchange D8C
      at position 8 of the WW domain (PyVP1-WW150-D8C)
<220> FEATURE:
<221> NAME/KEY: DOMAIN
<222> LOCATION: (149)..(186)
<223> OTHER INFORMATION: inserted WW domain (WW150)
<220> FEATURE:
<221> NAME/KEY: SITE
<222> LOCATION: (161)
<223> OTHER INFORMATION: inserted Cys in WW domain (WW150)

<400> SEQUENCE: 2

Met Ala Pro Lys Arg Lys Ser Gly Val Ser Lys Ser Glu Thr Lys Ser
  1               5                  10                  15

Thr Lys Ala Ser Pro Arg Pro Ala Pro Val Pro Lys Leu Leu Ile Lys
                 20                  25                  30

Gly Gly Met Glu Val Leu Asp Leu Val Thr Gly Pro Asp Ser Val Thr
             35                  40                  45

Glu Ile Glu Ala Phe Leu Asn Pro Arg Met Gly Gln Pro Pro Thr Pro
         50                  55                  60

Glu Ser Leu Thr Glu Gly Gly Gln Tyr Tyr Gly Trp Ser Arg Gly Ile
 65                  70                  75                  80

Asn Leu Ala Thr Ser Asp Thr Glu Asp Ser Pro Gly Asn Asn Thr Leu
                 85                  90                  95

Pro Thr Trp Ser Met Ala Lys Leu Gln Leu Pro Met Leu Asn Glu Asp
            100                 105                 110

Leu Thr Ser Asp Thr Leu Gln Met Trp Glu Ala Val Ser Val Lys Thr
        115                 120                 125

Glu Val Val Gly Ser Gly Ser Leu Leu Asp Val His Gly Phe Asn Lys
    130                 135                 140

Pro Thr Asp Thr Gly Ser Gly Ser Gly Trp Thr Glu His Lys Ser Pro
145                 150                 155                 160

Cys Gly Arg Thr Tyr Tyr Tyr Asn Thr Glu Thr Lys Gln Ser Thr Trp
                165                 170                 175

Glu Lys Pro Asp Asp Gly Ser Gly Ser Gly Val Asn Thr Lys Gly Ile
```

-continued

```
                    180                 185                 190
Ser Thr Pro Val Glu Gly Ser Gln Tyr His Val Phe Ala Val Gly Gly
        195                 200                 205

Glu Pro Leu Asp Leu Gln Gly Leu Val Thr Asp Ala Arg Thr Lys Tyr
210                 215                 220

Lys Glu Glu Gly Val Val Thr Ile Lys Thr Ile Thr Lys Lys Asp Met
225                 230                 235                 240

Val Asn Lys Asp Gln Val Leu Asn Pro Ile Ser Lys Ala Lys Leu Asp
                245                 250                 255

Lys Asp Gly Met Tyr Pro Val Glu Ile Trp His Pro Asp Pro Ala Lys
            260                 265                 270

Asn Glu Asn Thr Arg Tyr Phe Gly Asn Tyr Thr Gly Gly Thr Cys Thr
            275                 280                 285

Pro Pro Val Leu Gln Phe Thr Asn Thr Leu Thr Thr Val Leu Leu Asp
        290                 295                 300

Glu Asn Gly Val Gly Pro Leu Ser Lys Gly Glu Gly Leu Tyr Leu Ser
305                 310                 315                 320

Ser Val Asp Ile Met Gly Trp Arg Val Thr Arg Asn Tyr Asp Val His
                325                 330                 335

His Trp Arg Gly Leu Pro Arg Tyr Phe Lys Ile Thr Leu Arg Lys Arg
            340                 345                 350

Trp Val Lys Asn Pro Tyr Pro Met Ala Ser Leu Ile Ser Ser Leu Phe
            355                 360                 365

Asn Asn Met Leu Pro Gln Val Gln Gly Gln Pro Met Glu Gly Glu Asn
        370                 375                 380

Thr Gln Val Glu Glu Val Arg Val Tyr Asp Gly Thr Glu Pro Val Pro
385                 390                 395                 400

Gly Asp Pro Asp Met Thr Arg Tyr Val Asp Arg Phe Gly Lys Thr Lys
                405                 410                 415

Thr Val Phe Pro Pro Gly
            420

<210> SEQ ID NO 3
<211> LENGTH: 1266
<212> TYPE: DNA
<213> ORGANISM: Artificial Sequence
<220> FEATURE:
<223> OTHER INFORMATION: Description of Artificial Sequence:VP1-WW150,
      inserted WW domain from FBP11
<220> FEATURE:
<221> NAME/KEY: CDS
<222> LOCATION: (1)..(1266)
<223> OTHER INFORMATION: VP1-WW150
<220> FEATURE:
<221> NAME/KEY: misc_feature
<222> LOCATION: (445)..(558)
<223> OTHER INFORMATION: inserted WW domain (WW150)
<220> FEATURE:
<223> OTHER INFORMATION:

<400> SEQUENCE: 3 atg gcc ccc aaa aga aaa agc ggc gtc tct aaa agc gag aca aaa agc        48
Met Ala Pro Lys Arg Lys Ser Gly Val Ser Lys Ser Glu Thr Lys Ser
1               5                   10                  15 aca aag gct agc cca aga ccc gca ccc gtt ccc aaa ctg ctt att aaa        96
Thr Lys Ala Ser Pro Arg Pro Ala Pro Val Pro Lys Leu Leu Ile Lys
                20                  25                  30 ggg ggt atg gag gtg ctg gac ctt gtg aca ggg cca gac agt gtg aca       144
Gly Gly Met Glu Val Leu Asp Leu Val Thr Gly Pro Asp Ser Val Thr
            35                  40                  45
```

```
gaa ata gaa gct ttt ctg aac ccc aga atg ggg cag cca ccc acc cct     192
Glu Ile Glu Ala Phe Leu Asn Pro Arg Met Gly Gln Pro Pro Thr Pro
     50                  55                  60 gaa agc cta aca gag gga ggg caa tac tat ggt tgg agc aga ggg att     240
Glu Ser Leu Thr Glu Gly Gly Gln Tyr Tyr Gly Trp Ser Arg Gly Ile
 65                  70                  75                  80 aat ttg gct aca tca gat aca gag gat tcc cca gga aat aat aca ctt     288
Asn Leu Ala Thr Ser Asp Thr Glu Asp Ser Pro Gly Asn Asn Thr Leu
                 85                  90                  95 ccc aca tgg agt atg gca aag ctc cag ctt ccc atg ctc aat gag gac     336
Pro Thr Trp Ser Met Ala Lys Leu Gln Leu Pro Met Leu Asn Glu Asp
            100                 105                 110 ctc acg tct gac acc cta caa atg tgg gag gca gtc tca gtg aaa acc     384
Leu Thr Ser Asp Thr Leu Gln Met Trp Glu Ala Val Ser Val Lys Thr
        115                 120                 125 gag gtg gtg ggc tct ggc tca ctg tta gat gtg cat ggg ttc aac aaa     432
Glu Val Val Gly Ser Gly Ser Leu Leu Asp Val His Gly Phe Asn Lys
    130                 135                 140 ccc aca gat aca ggc agc ggc agc ggc tgg aca gaa cat aaa tca cct     480
Pro Thr Asp Thr Gly Ser Gly Ser Gly Trp Thr Glu His Lys Ser Pro
145                 150                 155                 160 gat gga agg act tat tat tac aat act gaa aca aaa cag tct acc tgg     528
Asp Gly Arg Thr Tyr Tyr Tyr Asn Thr Glu Thr Lys Gln Ser Thr Trp
                165                 170                 175 gaa aag cca gat gat ggt agt ggt agc ggc gta aac aca aaa gga att     576
Glu Lys Pro Asp Asp Gly Ser Gly Ser Gly Val Asn Thr Lys Gly Ile
            180                 185                 190 tcc act cca gtg gaa ggc agc caa tat cat gtg ttt gct gtg ggc ggg     624
Ser Thr Pro Val Glu Gly Ser Gln Tyr His Val Phe Ala Val Gly Gly
        195                 200                 205 gaa ccg ctt gac ctc cag gga ctt gtg aca gat gcc aga aca aaa tac     672
Glu Pro Leu Asp Leu Gln Gly Leu Val Thr Asp Ala Arg Thr Lys Tyr
    210                 215                 220 aag gaa gaa ggg gta gta aca atc aaa aca atc aca aag aag gac atg     720
Lys Glu Glu Gly Val Val Thr Ile Lys Thr Ile Thr Lys Lys Asp Met
225                 230                 235                 240 gtc aac aaa gac caa gtc ctg aat cca att agc aag gcc aag ctg gat     768
Val Asn Lys Asp Gln Val Leu Asn Pro Ile Ser Lys Ala Lys Leu Asp
                245                 250                 255 aag gac gga atg tat cca gtt gaa atc tgg cat cca gat cca gca aaa     816
Lys Asp Gly Met Tyr Pro Val Glu Ile Trp His Pro Asp Pro Ala Lys
            260                 265                 270 aat gag aac aca agg tac ttt ggc aat tac act gga ggc acg tgc acc     864
Asn Glu Asn Thr Arg Tyr Phe Gly Asn Tyr Thr Gly Gly Thr Cys Thr
        275                 280                 285 cca ccc gtc ctg cag ttc aca aac acc ctg aca act gtg ctc cta gat     912
Pro Pro Val Leu Gln Phe Thr Asn Thr Leu Thr Thr Val Leu Leu Asp
    290                 295                 300 gaa aat gga gtt ggg ccc ctc agc aaa gga gaa ggt cta tac ctc tcg     960
Glu Asn Gly Val Gly Pro Leu Ser Lys Gly Glu Gly Leu Tyr Leu Ser
305                 310                 315                 320 agc gta gat ata atg ggc tgg aga gtt aca aga aac tat gat gtc cat    1008
Ser Val Asp Ile Met Gly Trp Arg Val Thr Arg Asn Tyr Asp Val His
                325                 330                 335 cac tgg aga ggg ctt ccc aga tat ttc aaa atc acc ctg aga aaa aga    1056
His Trp Arg Gly Leu Pro Arg Tyr Phe Lys Ile Thr Leu Arg Lys Arg
            340                 345                 350 tgg gtc aaa aat ccc tat ccc atg gcc tcc ctc ata agt tcc ctt ttc    1104
Trp Val Lys Asn Pro Tyr Pro Met Ala Ser Leu Ile Ser Ser Leu Phe
```

-continued

```
              355                 360                 365
aac aac atg ctc ccc caa gtg cag ggc caa ccc atg gaa ggg gag aac      1152
Asn Asn Met Leu Pro Gln Val Gln Gly Gln Pro Met Glu Gly Glu Asn
        370                 375                 380 acc cag gta gag gag gtt aga gtg tat gat ggg act gaa cct gta ccg      1200
Thr Gln Val Glu Glu Val Arg Val Tyr Asp Gly Thr Glu Pro Val Pro
385                 390                 395                 400 ggg gac cct gat atg acg cgc tat gtt gac cgc ttt gga aaa aca aag      1248
Gly Asp Pro Asp Met Thr Arg Tyr Val Asp Arg Phe Gly Lys Thr Lys
                405                 410                 415 act gta ttt cct ccc ggg                                              1266
Thr Val Phe Pro Pro Gly
            420
```

<210> SEQ ID NO 4
<211> LENGTH: 422
<212> TYPE: PRT
<213> ORGANISM: Artificial Sequence
<220> FEATURE:
<223> OTHER INFORMATION: Description of Artificial Sequence:VP1-WW150,
      inserted WW domain from FBP11
<220> FEATURE:
<221> NAME/KEY: DOMAIN
<222> LOC -continued

```
                245                 250                 255

Lys Asp Gly Met Tyr Pro Val Glu Ile Trp His Pro Asp Pro Ala Lys
            260                 265                 270

Asn Glu Asn Thr Arg Tyr Phe Gly Asn Tyr Thr Gly Gly Thr Cys Thr
        275                 280                 285

Pro Pro Val Leu Gln Phe Thr Asn Thr Leu Thr Thr Val Leu Leu Asp
    290                 295                 300

Glu Asn Gly Val Gly Pro Leu Ser Lys Gly Glu Gly Leu Tyr Leu Ser
305                 310                 315                 320

Ser Val Asp Ile Met Gly Trp Arg Val Thr Arg Asn Tyr Asp Val His
                325                 330                 335

His Trp Arg Gly Leu Pro Arg Tyr Phe Lys Ile Thr Leu Arg Lys Arg
            340                 345                 350

Trp Val Lys Asn Pro Tyr Pro Met Ala Ser Leu Ile Ser Ser Leu Phe
        355                 360                 365

Asn Asn Met Leu Pro Gln Val Gln Gly Gln Pro Met Glu Gly Glu Asn
    370                 375                 380

Thr Gln Val Glu Glu Val Arg Val Tyr Asp Gly Thr Glu Pro Val Pro
385                 390                 395                 400

Gly Asp Pro Asp Met Thr Arg Tyr Val Asp Arg Phe Gly Lys Thr Lys
                405                 410                 415

Thr Val Phe Pro Pro Gly
            420

<210> SEQ ID NO 5
<211> LENGTH: 1251
<212> TYPE: DNA
<213> ORGANISM: Artificial Sequence
<220> FEATURE:
<223> OTHER INFORMATION: Description of Artificial Sequence:
      PyVP1-3C-WW1, N-terminal WW domain
<220> FEATURE:
<221> NAME/KEY: CDS
<222> LOCATION: (1)..(1251)
<223> OTHER INFORMATION: PyVP1-3C-WW1
<220> FEATURE:
<221> NAME/KEY: misc_feature
<222> LOCATION: (4)..(96)
<223> OTHER INFORMATION: N-terminal WW domain

<400> SEQUENCE: 5 atg agc ggc tgg aca gaa cat aaa tca cct gat gga agg act tat tat       48
Met Ser Gly Trp Thr Glu His Lys Ser Pro Asp Gly Arg Thr Tyr Tyr
  1               5                  10                  15 tac aat act gaa aca aaa cag tct acc tgg gaa aag cca gat gat gga       96
Tyr Asn Thr Glu Thr Lys Gln Ser Thr Trp Glu Lys Pro Asp Asp Gly
             20                  25                  30 cat atg gcc ccc aaa aga aaa agc ggc gtc tct aaa tct gag aca aaa      144
His Met Ala Pro Lys Arg Lys Ser Gly Val Ser Lys Ser Glu Thr Lys
         35                  40                  45 agc aca aag gcc tgt cca aga ccc gca ccc gtt ccc aaa ctg ctt att      192
Ser Thr Lys Ala Cys Pro Arg Pro Ala Pro Val Pro Lys Leu Leu Ile
     50                  55                  60 aaa ggg ggt atg gag gtg ctg gac ctt gtg aca ggg cca gac agt gtg      240
Lys Gly Gly Met Glu Val Leu Asp Leu Val Thr Gly Pro Asp Ser Val
 65                  70                  75                  80 aca gaa ata gaa gct ttt ctg aac ccc aga atg ggg cag cca ccc acc      288
Thr Glu Ile Glu Ala Phe Leu Asn Pro Arg Met Gly Gln Pro Pro Thr
                 85                  90                  95 cct gaa agc cta aca gag gga ggg caa tac tat ggt tgg agc aga ggg      336
```

```
Pro Glu Ser Leu Thr Glu Gly Gly Gln Tyr Tyr Gly Trp Ser Arg Gly
            100                 105                 110 att aat ttg gct aca tca gat aca gag gat tcc cca gga aat aat aca        384
Ile Asn Leu Ala Thr Ser Asp Thr Glu Asp Ser Pro Gly Asn Asn Thr
            115                 120                 125 ctt ccc aca tgg agt atg gca aag ctc cag ctt ccc atg ctc aat gag        432
Leu Pro Thr Trp Ser Met Ala Lys Leu Gln Leu Pro Met Leu Asn Glu
            130                 135                 140 gac ctc acc tgt gac acc cta caa atg tgg gag gca gtc tca gtg aaa        480
Asp Leu Thr Cys Asp Thr Leu Gln Met Trp Glu Ala Val Ser Val Lys
145                 150                 155                 160 acc gag gtg gtg ggc tct ggc tca ctg tta gat gtg cat ggg ttc aac        528
Thr Glu Val Val Gly Ser Gly Ser Leu Leu Asp Val His Gly Phe Asn
                165                 170                 175 aaa ccc aca gat aca gta aac aca aaa gga att tcc act cca gtg gaa        576
Lys Pro Thr Asp Thr Val Asn Thr Lys Gly Ile Ser Thr Pro Val Glu
                180                 185                 190 ggc agc caa tat cat gtg ttt gct gtg ggc ggg gaa ccg ctt gac ctc        624
Gly Ser Gln Tyr His Val Phe Ala Val Gly Gly Glu Pro Leu Asp Leu
                195                 200                 205 cag gga ctt gtg aca gat gcc aga aca aaa tac aag gaa gaa ggg gta        672
Gln Gly Leu Val Thr Asp Ala Arg Thr Lys Tyr Lys Glu Glu Gly Val
210                 215                 220 gta aca atc aaa aca atc aca aag aag gac atg gtc aac aaa gac caa        720
Val Thr Ile Lys Thr Ile Thr Lys Lys Asp Met Val Asn Lys Asp Gln
225                 230                 235                 240 gtc ctg aat cca att agc aag gcc aag ctg gat aag gac gga atg tat        768
Val Leu Asn Pro Ile Ser Lys Ala Lys Leu Asp Lys Asp Gly Met Tyr
                245                 250                 255 cca gtt gaa atc tgg cat cca gat cca gca aaa aat gag aac aca agg        816
Pro Val Glu Ile Trp His Pro Asp Pro Ala Lys Asn Glu Asn Thr Arg
                260                 265                 270 tac ttt ggc aat tac act gga ggc acg tgc act cca ccc gtc ctg cag        864
Tyr Phe Gly Asn Tyr Thr Gly Gly Thr Cys Thr Pro Pro Val Leu Gln
                275                 280                 285 ttc aca aac acc ctg aca act gtg ctc cta gat gaa aat gga gtt ggg        912
Phe Thr Asn Thr Leu Thr Thr Val Leu Leu Asp Glu Asn Gly Val Gly
            290                 295                 300 ccc ctc agc aaa gga gag ggc cta tac ctc tcg agc gta gat ata atg        960
Pro Leu Ser Lys Gly Glu Gly Leu Tyr Leu Ser Ser Val Asp Ile Met
305                 310                 315                 320 ggc tgg aga gtt aca aga aac tat gat gtc cat cac tgg aga ggg ctt       1008
Gly Trp Arg Val Thr Arg Asn Tyr Asp Val His His Trp Arg Gly Leu
                325                 330                 335 ccc aga tat ttc aaa atc acc ctg aga aaa aga tgg gtc aaa aat ccc       1056
Pro Arg Tyr Phe Lys Ile Thr Leu Arg Lys Arg Trp Val Lys Asn Pro
                340                 345                 350 tat ccc atg gcc tcc ctc ata agt tcc ctt ttc aac aac atg ctc ccc       1104
Tyr Pro Met Ala Ser Leu Ile Ser Ser Leu Phe Asn Asn Met Leu Pro
                355                 360                 365 caa gtg cag ggc caa ccc atg gaa ggg gag aac acc cag gta gag gag       1152
Gln Val Gln Gly Gln Pro Met Glu Gly Glu Asn Thr Gln Val Glu Glu
            370                 375                 380 gtt aga gtg tat gat ggg act gaa cct gta ccg ggg gac cct gat atg       1200
Val Arg Val Tyr Asp Gly Thr Glu Pro Val Pro Gly Asp Pro Asp Met
385                 390                 395                 400 acg cgc tat gtt gac cgc ttt gga aaa aca aag act gta ttt cct ccc       1248
Thr Arg Tyr Val Asp Arg Phe Gly Lys Thr Lys Thr Val Phe Pro Pro
                405                 410                 415
```

-continued

```
ggg                                                                1251
Gly

<210> SEQ ID NO 6
<211> LENGTH: 417
<212> TYPE: PRT
<213> ORGANISM: Artificial Sequence
<220> FEATURE:
<223> OTHER INFORMATION: Description of Artificial Sequence:
      PyVP1-3C-WW1, N

```
                    325                 330                 335
Pro Arg Tyr Phe Lys Ile Thr Leu Arg Lys Arg Trp Val Lys Asn Pro
            340                 345                 350
Tyr Pro Met Ala Ser Leu Ile Ser Ser Leu Phe Asn Asn Met Leu Pro
            355                 360                 365
Gln Val Gln Gly Gln Pro Met Glu Gly Glu Asn Thr Gln Val Glu Glu
            370                 375                 380
Val Arg Val Tyr Asp Gly Thr Glu Pro Val Pro Gly Asp Pro Asp Met
385                 390                 395                 400
Thr Arg Tyr Val Asp Arg Phe Gly Lys Thr Lys Thr Val Phe Pro Pro
            405                 410                 415
Gly

<210> SEQ ID NO 7
<211> LENGTH: 1179
<212> TYPE: DNA
<213> ORGANISM: Artificial Sequence
<220> FEATURE:
<223> OTHER INFORMATION: Description of Artificial
      Sequence:PyVP1-3C-[N-14]-PLP, proline-rich
      sequence at shortened N-terminus
<220> FEATURE:
<221> NAME/KEY: CDS
<222> LOCATION: (1)..(1179)
<223> OTHER INFORMATION: PyVP1-3C-[N-14]-PLP
<220> FEATURE:

```
aaa gga att tcc act cca gtg gaa ggc agc caa tat cat gtg ttt gct    528
Lys Gly Ile Ser Thr Pro Val Glu Gly Ser Gln Tyr His Val Phe Ala
            165                 170                 175 gtg ggc ggg gaa ccg ctt gac ctc cag gga ctt gta aca gat gcc aga    576
Val Gly Gly Glu Pro Leu Asp Leu Gln Gly Leu Val Thr Asp Ala Arg
        180                 185                 190 aca aaa tac aag gaa gaa ggg gta gta aca atc aaa aca atc aca aag    624
Thr Lys Tyr Lys Glu Glu Gly Val Val Thr Ile Lys Thr Ile Thr Lys
    195                 200                 205 aag gac atg gtc aac aaa gac caa gtc ctg aat cca att agc aag gcc    672
Lys Asp Met Val Asn Lys Asp Gln Val Leu Asn Pro Ile Ser Lys Ala
210                 215                 220 aag ctg gat aag gac gga atg tat cca gtt gaa atc tgg cat cca gat    720
Lys Leu Asp Lys Asp Gly Met Tyr Pro Val Glu Ile Trp His Pro Asp
225                 230                 235                 240 cca gca aaa aat gag aac aca agg tac ttt ggc aat tac act gga ggc    768
Pro Ala Lys Asn Glu Asn Thr Arg Tyr Phe Gly Asn Tyr Thr Gly Gly
                245                 250                 255 acg tgc acc cca ccc gtc ctg cag ttc aca aac acc ctg aca act gtg    816
Thr Cys Thr Pro Pro Val Leu Gln Phe Thr Asn Thr Leu Thr Thr Val
            260                 265                 270 ctc cta gat gaa aat gga gtt ggg ccc ctc agc aaa gga gaa ggt cta    864
Leu Leu Asp Glu Asn Gly Val Gly Pro Leu Ser Lys Gly Glu Gly Leu
        275                 280                 285 tac ctc tcg agc gta gat ata atg ggc tgg aga gtt aca aga aac tat    912
Tyr Leu Ser Ser Val Asp Ile Met Gly Trp Arg Val Thr Arg Asn Tyr
    290                 295                 300 gat gtc cat cac tgg aga ggg ctt ccc aga tat ttc aaa atc acc ctg    960
Asp Val His His Trp Arg Gly Leu Pro Arg Tyr Phe Lys Ile Thr Leu
305                 310                 315                 320 aga aaa aga tgg gtc aaa aat ccc tat ccc atg gcc tcc ctc ata agt   1008
Arg Lys Arg Trp Val Lys Asn Pro Tyr Pro Met Ala Ser Leu Ile Ser
                325                 330                 335 tcc ctt ttc aac aac atg ctc ccc caa gtg cag ggc caa ccc atg gaa   1056
Ser Leu Phe Asn Asn Met Leu Pro Gln Val Gln Gly Gln Pro Met Glu
            340                 345                 350 ggg gag aac acc cag gta gag gag gtt aga gtg tat gat ggg act gaa   1104
Gly Glu Asn Thr Gln Val Glu Glu Val Arg Val Tyr Asp Gly Thr Glu
        355                 360                 365 cct gta ccg ggg gac cct gat atg acg cgc tat gtt gac cgc ttt gga   1152
Pro Val Pro Gly Asp Pro Asp Met Thr Arg Tyr Val Asp Arg Phe Gly
    370                 375                 380 aaa aca aag act gta ttt cct ccc ggg                               1179
Lys Thr Lys Thr Val Phe Pro Pro Gly
385                 390
```

<210> SEQ ID NO 8
<211> LENGTH: 393
<212> TYPE: PRT
<213> ORGANISM: Artificial Sequence
<220> FEATURE:
<223> OTHER INFORMATION: Description of Artificial
      Sequence:PyVP1-3C-[N-14]-PLP, proline-rich
      sequence at shortened N-terminus
<220> FEATURE:
<221> NAME/KEY: PEPTIDE
<222> LOCATION: (2)..(11)
<223> OTHER INFORMATION: proline-rich sequence

<400> SEQUENCE: 8

```
Met Pro Pro Pro Pro Pro Pro Pro Leu Pro Gly Leu Gly Arg Arg
 1               5                  10

```
Gly Leu Ala Thr Ser His Gly Leu Ser Thr Lys Ala Cys Pro Arg Pro
             20                  25                  30

Ala Pro Val Pro Lys Leu Leu Ile Lys Gly Gly Met Glu Val Leu Asp
         35                  40                  45

Leu Val Thr Gly Pro Asp Cys Val Thr Glu Ile Glu Ala Phe Leu Asn
 50                  55                  60

Pro Arg Met Gly Gln Pro Pro Thr Pro Glu Ser Leu Thr Glu Gly Gly
 65                  70                  75                  80

Gln Tyr Tyr Gly Trp Ser Arg Gly Ile Asn Leu Ala Thr Ser Asp Thr
                 85                  90                  95

Glu Asp Ser Pro Gly Asn Asn Thr Leu Pro Thr Trp Ser Met Ala Lys
            100                 105                 110

Leu Gln Leu Pro Met Leu Asn Glu Asp Leu Thr Cys Asp Thr Leu Gln
        115                 120                 125

Met Trp Glu Ala Val Ser Val Lys Thr Glu Val Val Gly Ser Gly Ser
130                 135                 140

Leu Leu Asp Val His Gly Phe Asn Lys Pro Thr Asp Thr Val Asn Thr
145                 150                 155                 160

Lys Gly Ile Ser Thr Pro Val Glu Gly Ser Gln Tyr His Val Phe Ala
                165                 170                 175

Val Gly Gly Glu Pro Leu Asp Leu Gln Gly Leu Val Thr Asp Ala Arg
            180                 185                 190

Thr Lys Tyr Lys Glu Glu Gly Val Val Thr Ile Lys Thr Ile Thr Lys
        195                 200                 205

Lys Asp Met Val Asn Lys Asp Gln Val Leu Asn Pro Ile Ser Lys Ala
210                 215                 220

Lys Leu Asp Lys Asp Gly Met Tyr Pro Val Glu Ile Trp His Pro Asp
225                 230                 235                 240

Pro Ala Lys Asn Glu Asn Thr Arg Tyr Phe Gly Asn Tyr Thr Gly Gly
                245                 250                 255

Thr Cys Thr Pro Pro Val Leu Gln Phe Thr Asn Thr Leu Thr Thr Val
            260                 265                 270

Leu Leu Asp Glu Asn Gly Val Gly Pro Leu Ser Lys Gly Glu Gly Leu
        275                 280                 285

Tyr Leu Ser Ser Val Asp Ile Met Gly Trp Arg Val Thr Arg Asn Tyr
290                 295                 300

Asp Val His His Trp Arg Gly Leu Pro Arg Tyr Phe Lys Ile Thr Leu
305                 310                 315                 320

Arg Lys Arg Trp Val Lys Asn Pro Tyr Pro Met Ala Ser Leu Ile Ser
                325                 330                 335

Ser Leu Phe Asn Asn Met Leu Pro Gln Val Gln Gly Gln Pro Met Glu
            340                 345                 350

Gly Glu Asn Thr Gln Val Glu Glu Val Arg Val Tyr Asp Gly Thr Glu
        355                 360                 365

Pro Val Pro Gly Asp Pro Asp Met Thr Arg Tyr Val Asp Arg Phe Gly
370                 375                 380

Lys Thr Lys Thr Val Phe Pro Pro Gly
385                 390

<210> SEQ ID NO 9
<211> LENGTH: 1209
<212> TYPE: DNA
<213> ORGANISM: Artificial Sequence
<220> FEATURE:
<223> OTHER INFORMATION: Description of Artificial
```

```
        Sequence:PyVP1-3C-WW[N-14], WW domain
        at shortened N-terminus
<220> FEATURE:
<221> NAME/K -continued

```
            260                 265                 270 ctg cag ttc aca aac acc ctg aca act gtg ctc cta gat gaa aat gga      864
Leu Gln Phe Thr Asn Thr Leu Thr Thr Val Leu Leu Asp Glu Asn Gly
        275                 280                 285 gtt ggg ccc ctc agc aaa gga gaa ggt cta tac ctc tcg agc gta gat      912
Val Gly Pro Leu Ser Lys Gly Glu Gly Leu Tyr Leu Ser Ser Val Asp
    290                 295                 300 ata atg ggc tgg aga gtt aca aga aac tat gat gtc cat cac tgg aga      960
Ile Met Gly Trp Arg Val Thr Arg Asn Tyr Asp Val His His Trp Arg
305                 310                 315                 320 ggg ctt ccc aga tat ttc aaa atc acc ctg aga aaa aga tgg gtc aaa     1008
Gly Leu Pro Arg Tyr Phe Lys Ile Thr Leu Arg Lys Arg Trp Val Lys
                325                 330                 335 aat ccc tat ccc atg gcc tcc ctc ata agt tcc ctt ttc aac aac atg     1056
Asn Pro Tyr Pro Met Ala Ser Leu Ile Ser Ser Leu Phe Asn Asn Met
            340                 345                 350 ctc ccc caa gtg cag ggc caa ccc atg gaa ggg gag aac acc cag gta     1104
Leu Pro Gln Val Gln Gly Gln Pro Met Glu Gly Glu Asn Thr Gln Val
        355                 360                 365 gag gag gtt aga gtg tat gat ggg act gaa cct gta ccg ggg gac cct     1152
Glu Glu Val Arg Val Tyr Asp Gly Thr Glu Pro Val Pro Gly Asp Pro
    370                 375                 380 gat atg acg cgc tat gtt gac cgc ttt gga aaa aca aag act gta ttt     1200
Asp Met Thr Arg Tyr Val Asp Arg Phe Gly Lys Thr Lys Thr Val Phe
385                 390                 395                 400 cct ccc ggg                                                         1209
Pro Pro Gly <210> SEQ ID NO 10
<211> LENGTH: 403
<212> TYPE: PRT
<213> ORGANISM: Artificial Sequence
<220> FEATURE:
<223> OTHER INFORMATION: Description of Artificial
      Sequence:PyVP1-3C-WW[N-14], WW domain
      at shortened N-terminus
<220> FEATURE:
<221> NAME/KEY: DOMAIN
<222> LOCATION: (2)..(32)
<223> OTHER INFORMATION: WW domain

<400> SEQUENCE: 10

Met Ser Gly Trp Thr Glu His Lys Ser Pro Asp Gly Arg Thr Tyr Tyr
  1               5                  10                  15

Tyr Asn Thr Glu Thr Lys Gln Ser Thr Trp Glu Lys Pro Asp Asp Gly
             20                  25                  30

His Met Ser Thr Lys Ala Cys Pro Arg Pro Ala Pro Val Pro Lys Leu
         35                  40                  45

Leu Ile Lys Gly Gly Met Glu Val Leu Asp Leu Val Thr Gly Pro Asp
     50                  55                  60

Ser Val Thr Glu Ile Glu Ala Phe Leu Asn Pro Arg Met Gly Gln Pro
 65                  70                  75                  80

Pro Thr Pro Glu Ser Leu Thr Glu Gly Gly Gln Tyr Tyr Gly Trp Ser
                 85                  90                  95

Arg Gly Ile Asn Leu Ala Thr Ser Asp Thr Glu Asp Ser Pro Gly Asn
            100                 105                 110

Asn Thr Leu Pro Thr Trp Ser Met Ala Lys Leu Gln Leu Pro Met Leu
        115                 120                 125

Asn Glu Asp Leu Thr Cys Asp Thr Leu Gln Met Trp Glu Ala Val Ser
    130                 135                 140
```

```
Val Lys Thr Glu Val Val Gly Ser Gly Ser Leu Leu Asp Val His Gly
145                 150                 155                 160

Phe Asn Lys Pro Thr Asp Thr Val Asn Thr Lys Gly Ile Ser Thr Pro
                165                 170                 175

Val Glu Gly Ser Gln Tyr His Val Phe Ala Val Gly Gly Glu Pro Leu
            180                 185                 190

Asp Leu Gln Gly Leu Val Thr Asp Ala Arg Thr Lys Tyr Lys Glu Glu
            195                 200                 205

Gly Val Val Thr Ile Lys Thr Ile Thr Lys Lys Asp Met Val Asn Lys
210                 215                 220

Asp Gln Val Leu Asn Pro Ile Ser Lys Ala Lys Leu Asp Lys Asp Gly
225                 230                 235                 240

Met Tyr Pro Val Glu Ile Trp His Pro Asp Pro Ala Lys Asn Glu Asn
                245                 250                 255

Thr Arg Tyr Phe Gly Asn Tyr Thr Gly Gly Thr Cys Thr Pro Pro Val
                260                 265                 270

Leu Gln Phe Thr Asn Thr Leu Thr Thr Val Leu Leu Asp Glu Asn Gly
            275                 280                 285

Val Gly Pro Leu Ser Lys Gly Glu Gly Leu Tyr Leu Ser Ser Val Asp
290                 295                 300

Ile Met Gly Trp Arg Val Thr Arg Asn Tyr Asp Val His His Trp Arg
305                 310                 315                 320

Gly Leu Pro Arg Tyr Phe Lys Ile Thr Leu Arg Lys Arg Trp Val Lys
                325                 330                 335

Asn Pro Tyr Pro Met Ala Ser Leu Ile Ser Ser Leu Phe Asn Asn Met
                340                 345                 350

Leu Pro Gln Val Gln Gly Gln Pro Met Glu Gly Glu Asn Thr Gln Val
            355                 360                 365

Glu Glu Val Arg Val Tyr Asp Gly Thr Glu Pro Val Pro Gly Asp Pro
            370                 375                 380

Asp Met Thr Arg Tyr Val Asp Arg Phe Gly Lys Thr Lys Thr Val Phe
385                 390                 395                 400

Pro Pro Gly

<210> SEQ ID NO 11
<211> LENGTH: 765
<212> TYPE: DNA
<213> ORGANISM: Artificial Sequence
<220> FEATURE:
<223> OTHER INFORMATION: Description of Artificial Sequence:GFP-PLP,
      proline-rich sequence at C-terminus
<220> FEATURE:
<221> NAME/KEY: CDS
<222> LOCATION: (1)..(765)
<223> OTHER INFORMATION: GFP-PLP
<220> FEATURE:
<221> NAME/KEY: misc_feature
<222> LOCATION: (736)..(765)
<223> OTHER INFORMATION: proline-rich sequence

<400> SEQUENCE: 11 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc     144
```

```
                                                                                            -continued Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc       192
Cys Thr Thr Gly Lys Leu Pro Val Pro Trp Pro Thr Leu Val Thr Thr
 50                  55                  60 ctg acc tac ggc gtg cag tgc ttc agc cgc tac ccc gac cac atg aag       240
Leu Thr Tyr Gly Val Gln Cys Phe Ser Arg Tyr Pro Asp His Met Lys
 65                  70                  75                  80 cag cac gac ttc ttc aag tcc gcc atg ccc gaa ggc tac gtc cag gag       288
Gln His Asp Phe Phe Lys Ser Ala Met Pro Glu Gly Tyr Val Gln Glu
                     85                  90                  95 cgc acc atc ttc ttc aag gac gac ggc aac tac aag acc cgc gcc gag       336
Arg Thr Ile Phe Phe Lys Asp Asp Gly Asn Tyr Lys Thr Arg Ala Glu
                100                 105                 110 gtg aag ttc gag ggc gac acc ctg gtg aac cgc atc gag ctg aag ggc       384
Val Lys Phe Glu Gly Asp Thr Leu Val Asn Arg Ile Glu Leu Lys Gly
            115                 120                 125 atc gac ttc aag gag gac ggc aac atc ctg ggg cac aag ctg gag tac       432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac       480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag ggc ggc agc       528
Gly Ile Lys Val Asn Phe Lys Ile Arg His Asn Ile Glu Gly Gly Ser
                165                 170                 175 gtg cag ctc gcc gac cac tac cag cag aac acc ccc atc ggc gac ggc       576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg       624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc       672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac tta agc       720
Val Thr Ala Ala Gly Ile Thr Leu Gly Met Asp Glu Leu Tyr Leu Ser
225                 230                 235                 240 cga cgt gcc tca ggt ccg ccg cct cca ccg cca ccg cct tta ccc           765
Arg Arg Ala Ser Gly Pro Pro Pro Pro Pro Pro Pro Leu Pro
                245                 250                 255

<210> SEQ ID NO 12
<211> LENGTH: 255
<212> TYPE: PRT
<213> ORGANISM: Artificial Sequence
<220> FEATURE:
<223> OTHER INFORMATION: Description of Artificial Sequence:GFP-PLP,
      proline-rich sequence at C-terminus
<220> FEATURE:
<221> NAME/KEY: PEPTIDE
<222> LOCATION: (246)..(255)
<223> OTHER INFORMATION: proline-rich sequence

<400> SEQUENCE: 12

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45
```

```
Cys Thr Thr Gly Lys Leu Pro Val Pro Trp Pro Thr Leu Val Thr Thr
         50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
             100                 105                 110

Val Lys Phe Glu Gly Asp Thr Leu Val Asn Arg Ile Glu Leu Lys Gly
         115                 120                 125

Ile Asp Phe Lys Glu Asp Gly Asn Ile Leu Gly His Lys Leu Glu Tyr
     130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Gly Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Leu Ser
225                 230                 235                 240

Arg Arg Ala Ser Gly Pro Pro Pro Pro Pro Pro Leu Pro
                245                 250                 255

<210> SEQ ID NO 13
<211> LENGTH: 837
<212> TYPE: DNA
<213> ORGANISM: Artificial Sequence
<220> FEATURE:
<223> OTHER INFORMATION: Description of Artificial Sequence:GFP-WW1, WW
      domain at N-terminus
<220> FEATURE:
<221> NAME/KEY: CDS
<222> LOCATION: (1)..(837)
<223> OTHER INFORMATION: GFP-WW1
<220> FEATURE:
<221> NAME/KEY: misc_feature
<222> LOCATION: (4)..(96)
<223> OTHER INFORMATION: WW domain

<400> SEQUENCE: 13 atg agc ggc tgg aca gaa cat aaa tca cct gat gga agg act tat tat      48
Met Ser Gly Trp Thr Glu His Lys Ser Pro Asp Gly Arg Thr Tyr Tyr
 1               5                  10                  15 tac aat act gaa aca aaa cag tct acc tgg gaa aag cca gat gat gga      96
Tyr Asn Thr Glu Thr Lys Gln Ser Thr Trp Glu Lys Pro Asp Asp Gly
             20                  25                  30 cat atg agc acc aag gct agc gtg agc aag ggc gag gag ctg ttc acc     144
His Met Ser Thr Lys Ala Ser Val Ser Lys Gly Glu Glu Leu Phe Thr
         35                  40                  45 ggg gtg gtg ccc atc ctg gtc gag ctg gac ggc gac gta aac ggc cac     192
Gly Val Val Pro Ile Leu Val Glu Leu Asp Gly Asp Val Asn Gly His
     50                  55                  60 aag ttc agc gtg tcc ggc gag ggc gag ggc gat gcc acc tac ggc aag     240
Lys Phe Ser Val Ser Gly Glu Gly Glu Gly Asp Ala Thr Tyr Gly Lys
 65                  70                  75                  80 ctg acc ctg aag ttc atc tgc acc acc ggc aag ctg ccc gtg ccc tgg     288
```

```
                                                                        336
ccc acc ctc gtg acc acc ctg acc tac ggc gtg cag tgc ttc agc cgc
Pro Thr Leu Val Thr Thr Leu Thr Tyr Gly Val Gln Cys Phe Ser Arg
            100                 105                 110

384
tac ccc gac cac atg aag cag cac gac ttc ttc aag tcc gcc atg ccc
Tyr Pro Asp His Met Lys Gln His Asp Phe Phe Lys Ser Ala Met Pro
            115                 120                 125

432
gaa ggc tac gtc cag gag cgc acc atc ttc ttc aag gac gac ggc aac
Glu Gly Tyr Val Gln Glu Arg Thr Ile Phe Phe Lys Asp Asp Gly Asn
            130                 135                 140

480
tac aag acc cgc gcc gag gtg aag ttc gag ggc gac acc ctg gtg aac
Tyr Lys Thr Arg Ala Glu Val Lys Phe Glu Gly Asp Thr Leu Val Asn
145                 150                 155                 160

528
cgc atc gag ctg aag ggc atc gac ttc aag gag gac ggc aac atc ctg
Arg Ile Glu Leu Lys Gly Ile Asp Phe Lys Glu Asp Gly Asn Ile Leu
                165                 170                 175

576
ggg cac aag ctg gag tac aac tac aac agc cac aac gtc tat atc atg
Gly His Lys Leu Glu Tyr Asn Tyr Asn Ser His Asn Val Tyr Ile Met
            180                 185                 190

624
gcc gac aag cag aag aac ggc atc aag gtg aac ttc aag atc cgc cac
Ala Asp Lys Gln Lys Asn Gly Ile Lys Val Asn Phe Lys Ile Arg His
195                 200                 205

672
aac atc gag gac ggc agc gtg cag ctc gcc gac cac tac cag cag aac
Asn Ile Glu Asp Gly Ser Val Gln Leu Ala Asp His Tyr Gln Gln Asn
        210                 215                 220

720
acc ccc atc ggc gac ggc ccc gtg ctg ctg ccc gac aac cac tac ctg
Thr Pro Ile Gly Asp Gly Pro Val Leu Leu Pro Asp Asn His Tyr Leu
225                 230                 235                 240

768
agc acc cag tcc gcc ctg agc aaa gac ccc aac gag aag cgc gat cac
Ser Thr Gln Ser Ala Leu Ser Lys Asp Pro Asn Glu Lys Arg Asp His
                245                 250                 255

816
atg gtc ctg ctg gag ttc gtg acc gcc gcc ggg atc act ctc ggc atg
Met Val Leu Leu Glu Phe Val Thr Ala Ala Gly Ile Thr Leu Gly Met
            260                 265                 270

837
gac gag ctg tac tta att ccc
Asp Glu Leu Tyr Leu Ile Pro
        275

<210> SEQ ID NO 14
<211> LENGTH: 279
<212> TYPE: PRT
<213> ORGANISM: Artificial Sequence
<220> FEATURE:
<223> OTHER INFORMATION: Description of Artificial Sequence:GFP-WW1, WW
      domain at N-terminus
<220> FEATURE:
<221> NAME/KEY: DOMAIN
<222> LOCATION: (2)..(32)
<223> OTHER INFORMATION: WW domain

<400> SEQUENCE: 14

Met Ser Gly Trp Thr Glu His Lys Ser Pro Asp Gly Arg Thr Tyr Tyr
 1               5                  10                  15

Tyr Asn Thr Glu Thr Lys Gln Ser Thr Trp Glu Lys Pro Asp Asp Gly
            20                  25                  30

His Met Ser Thr Lys Ala Ser Val Ser Lys Gly Glu Glu Leu Phe Thr
        35                  40                  45

Gly Val Val Pro Ile Leu Val Glu Leu Asp Gly Asp Val Asn Gly His
    50                  55                  60

Lys Phe Ser Val Ser Gly Glu Gly Glu Gly Asp Ala Thr Tyr Gly Lys
```

-continued

```
                 65                  70                  75                  80
Leu Thr Leu Lys Phe Ile Cys Thr Thr Gly Lys Leu Pro Val Pro Trp
                         85                  90                  95

Pro Thr Leu Val Thr Thr Leu Thr Tyr Gly Val Gln Cys Phe Ser Arg
            100                 105                 110

Tyr Pro Asp His Met Lys Gln His Asp Phe Phe Lys Ser Ala Met Pro
        115                 120                 125

Glu Gly Tyr Val Gln Glu Arg Thr Ile Phe Phe Lys Asp Asp Gly Asn
    130                 135                 140

Tyr Lys Thr Arg Ala Glu Val Lys Phe Glu Gly Asp Thr Leu Val Asn
145                 150                 155                 160

Arg Ile Glu Leu Lys Gly Ile Asp Phe Lys Glu Asp Gly Asn Ile Leu
                165                 170                 175

Gly His Lys Leu Glu Tyr Asn Tyr Asn Ser His Asn Val Tyr Ile Met
            180                 185                 190

Ala Asp Lys Gln Lys Asn Gly Ile Lys Val Asn Phe Lys Ile Arg His
        195                 200                 205

Asn Ile Glu Asp Gly Ser Val Gln Leu Ala Asp His Tyr Gln Gln Asn
    210                 215                 220

Thr Pro Ile Gly Asp Gly Pro Val Leu Leu Pro Asp Asn His Tyr Leu
225                 230                 235                 240

Ser Thr Gln Ser Ala Leu Ser Lys Asp Pro Asn Glu Lys Arg Asp His
                245                 250                 255

Met Val Leu Leu Glu Phe Val Thr Ala Ala Gly Ile Thr Leu Gly Met
            260                 265                 270

Asp Glu Leu Tyr Leu Ile Pro
        275
```

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence:synthetic proline-rich peptide (PLP)

<400> SEQUENCE: 15

```
Cys Ser Gly Pro Pro Pro Pro Pro Pro Pro Pro Leu Pro
  1               5                  10
```

<210> SEQ ID NO 16
<211> LENGTH: 1152
<212> TYPE: DNA
<213> ORGANISM: Artificial Sequence
<220> FEATURE:
<223> OTHER INFORMATION: Description of Artificial
     Sequence:PyVP1-CallS-T249C variant of polyoma VP1
     protein with all Cys replaced by Ser and exchange
     of Thr 249 to Cys
<220> FEATURE:
<221> NAME/KEY: CDS
<222> LOCATION: (1)..(1152)
<223> OTHER INFORMATION: PyVP1-CallS-T249C variant

<400> SEQUENCE: 16

```
atg gcc ccc aaa aga aaa agc ggc gtc tct aaa agc gag aca aaa agc      48
Met Ala Pro Lys Arg Lys Ser Gly Val Ser Lys Ser Glu Thr Lys Ser
  1               5                  10                  15 aca aag gct agc cca aga ccc gca ccc gtt ccc aaa ctg ctt att aaa      96
Thr Lys Ala Ser Pro Arg Pro Ala Pro Val Pro Lys Leu Leu Ile Lys
                 20                  25                  30
```

```
ggg ggt atg gag gtg ctg gac ctt gtg aca ggg cca gac agt gtg aca      144
Gly Gly Met Glu Val Leu Asp Leu Val Thr Gly Pro Asp Ser Val Thr
        35                  40                  45 gaa ata gaa gct ttt ctg aac ccc aga atg ggg cag cca ccc acc cct      192
Glu Ile Glu Ala Phe Leu Asn Pro Arg Met Gly Gln Pro Pro Thr Pro
 50                  55                  60 gaa agc cta aca gag gga ggg caa tac tat ggt tgg agc aga ggg att      240
Glu Ser Leu Thr Glu Gly Gly Gln Tyr Tyr Gly Trp Ser Arg Gly Ile
 65                  70                  75                  80 aat ttg gct aca tca gat aca gag gat tcc cca gga aat aat aca ctt      288
Asn Leu Ala Thr Ser Asp Thr Glu Asp Ser Pro Gly Asn Asn Thr Leu
                 85                  90                  95 ccc aca tgg agt atg gca aag ctc cag ctt ccc atg ctc aat gag gac      336
Pro Thr Trp Ser Met Ala Lys Leu Gln Leu Pro Met Leu Asn Glu Asp
            100                 105                 110 ctc acg tct gac acc cta caa atg tgg gag gca gtc tca gtg aaa acc      384
Leu Thr Ser Asp Thr Leu Gln Met Trp Glu Ala Val Ser Val Lys Thr
        115                 120                 125 gag gtg gtg ggc tct ggc tca ctg tta gat gtg cat ggg ttc aac aaa      432
Glu Val Val Gly Ser Gly Ser Leu Leu Asp Val His Gly Phe Asn Lys
130                 135                 140 ccc aca gat aca gta aac aca aaa gga att tcc act cca gtg gaa ggc      480
Pro Thr Asp Thr Val Asn Thr Lys Gly Ile Ser Thr Pro Val Glu Gly
145                 150                 155                 160 agc caa tat cat gtg ttt gct gtg ggc ggg gaa ccg ctt gac ctc cag      528
Ser Gln Tyr His Val Phe Ala Val Gly Gly Glu Pro Leu Asp Leu Gln
                165                 170                 175 gga ctt gtg aca gat gcc aga aca aaa tac aag gaa gaa ggg gta gta      576
Gly Leu Val Thr Asp Ala Arg Thr Lys Tyr Lys Glu Glu Gly Val Val
            180                 185                 190 aca atc aaa aca atc aca aag aag gac atg gtc aac aaa gac caa gtc      624
Thr Ile Lys Thr Ile Thr Lys Lys Asp Met Val Asn Lys Asp Gln Val
        195                 200                 205 ctg aat cca att agc aag gcc aag ctg gat aag gac gga atg tat cca      672
Leu Asn Pro Ile Ser Lys Ala Lys Leu Asp Lys Asp Gly Met Tyr Pro
210                 215                 220 gtt gaa atc tgg cat cca gat cca gca aaa aat gag aac aca agg tac      720
Val Glu Ile Trp His Pro Asp Pro Ala Lys Asn Glu Asn Thr Arg Tyr
225                 230                 235                 240 ttt ggc aat tac act gga ggc acg tgc acc cca ccc gtc ctg cag ttc      768
Phe Gly Asn Tyr Thr Gly Gly Thr Cys Thr Pro Pro Val Leu Gln Phe
                245                 250                 255 aca aac acc ctg aca act gtg ctc cta gat gaa aat gga gtt ggg ccc      816
Thr Asn Thr Leu Thr Thr Val Leu Leu Asp Glu Asn Gly Val Gly Pro
            260                 265                 270 ctc agc aaa gga gaa ggt cta tac ctc tcg agc gta gat ata atg ggc      864
Leu Ser Lys Gly Glu Gly Leu Tyr Leu Ser Ser Val Asp Ile Met Gly
        275                 280                 285 tgg aga gtt aca aga aac tat gat gtc cat cac tgg aga ggg ctt ccc      912
Trp Arg Val Thr Arg Asn Tyr Asp Val His His Trp Arg Gly Leu Pro
290                 295                 300 aga tat ttc aaa atc acc ctg aga aaa aga tgg gtc aaa aat ccc tat      960
Arg Tyr Phe Lys Ile Thr Leu Arg Lys Arg Trp Val Lys Asn Pro Tyr
305                 310                 315                 320 ccc atg gcc tcc ctc ata agt tcc ctt ttc aac aac atg ctc ccc caa     1008
Pro Met Ala Ser Leu Ile Ser Ser Leu Phe Asn Asn Met Leu Pro Gln
                325                 330                 335 gtg cag ggc caa ccc atg gaa ggg gag aac acc cag gta gag gag gtt     1056
Val Gln Gly Gln Pro Met Glu Gly Glu Asn Thr Gln Val Glu Glu Val
```

-continued

```
              340                 345                 350
aga gtg tat gat ggg act gaa cct gta ccg ggg gac cct gat atg acg      1104
Arg Val Tyr Asp Gly Thr Glu Pro Val Pro Gly Asp Pro Asp Met Thr
            355                 360                 365 cgc tat gtt gac cgc ttt gga aaa aca aag act gta ttt cct ccc ggg      1152
Arg Tyr Val Asp Arg Phe Gly Lys Thr Lys Thr Val Phe Pro Pro Gly
370                 375                 380
```

<210> SEQ ID NO 17
<211> LENGTH: 384
<212> TYPE: PRT
<213> ORGANISM: Artificial Sequence
<220> FEATURE:
<223> OTHER INFORMATION: Description of Artificial
      Sequence:PyVP1-CallS-T249C variant of polyoma VP1
      protein with all Cys replaced by Ser and exchange
      of Thr 249 to Cys

<400> SEQUENCE: 17

```
Met Ala Pro Lys Arg Lys Ser Gly Val Ser Lys Ser Glu Thr Lys Ser
1               5                   10                  15

Thr Lys Ala Ser Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Asp Thr Glu Asp Ser Pro Gly Asn Asn Thr Leu
                85                  90                  95

Pro Thr Trp Ser Met Ala Lys Leu Gln Leu Pro Met Leu Asn Glu Asp
            100                 105                 110

Leu Thr Ser Asp Thr Leu Gln Met Trp Glu Ala Val Ser Val Lys Thr
        115                 120                 125

Glu Val Val Gly Ser Gly Ser Leu Leu Asp Val His Gly Phe Asn Lys
    130                 135                 140

Pro Thr Asp Thr Val Asn Thr Lys Gly Ile Ser Thr Pro Val Glu Gly
145                 150                 155                 160

Ser Gln Tyr His Val Phe Ala Val Gly Gly Glu Pro Leu Asp Leu Gln
                165                 170                 175

Gly Leu Val Thr Asp Ala Arg Thr Lys Tyr Lys Glu Glu Gly Val Val
            180                 185                 190

Thr Ile Lys Thr Ile Thr Lys Lys Asp Met Val Asn Lys Asp Gln Val
        195                 200                 205

Leu Asn Pro Ile Ser Lys Ala Lys Leu Asp Lys Asp Gly Met Tyr Pro
    210                 215                 220

Val Glu Ile Trp His Pro Asp Pro Ala Lys Asn Glu Asn Thr Arg Tyr
225                 230                 235                 240

Phe Gly Asn Tyr Thr Gly Gly Thr Cys Thr Pro Pro Val Leu Gln Phe
                245                 250                 255

Thr Asn Thr Leu Thr Thr Val Leu Leu Asp Glu Asn Gly Val Gly Pro
            260                 265                 270

Leu Ser Lys Gly Glu Gly Leu Tyr Leu Ser Ser Val Asp Ile Met Gly
        275                 280                 285

Trp Arg Val Thr Arg Asn Tyr Asp Val His His Trp Arg Gly Leu Pro
    290                 295                 300
```

```
Arg Tyr Phe Lys Ile Thr Leu Arg Lys Arg Trp Val Lys Asn Pro Tyr
305                 310                 315                 320

Pro Met Ala Ser Leu Ile Ser Ser Leu Phe Asn Asn Met Leu Pro Gln
            325                 330                 335

Val Gln Gly Gln Pro Met Glu Gly Glu Asn Thr Gln Val Glu Val
        340                 345                 350

Arg Val Tyr Asp Gly Thr Glu Pro Val Pro Gly Asp Pro Asp Met Thr
            355                 360                 365

Arg Tyr Val Asp Arg Phe Gly Lys Thr Lys Thr Val Phe Pro Pro Gly
        370                 375                 380

<210> SEQ ID NO 18
<211> LENGTH: 1110
<212> TYPE: DNA
<213> ORGANISM: Artificial Sequence
<220> FEATURE:
<223> OTHER INFORMATION: Description of Artificial Sequence:
      PyVP1-3C-[N-14] variant of polyomavirus VP1 protein shortened -continued

```
                180                 185                 190
caa gtc ctg aat cca att agc aag gcc aag ctg gat aag gac gga atg      624
Gln Val Leu Asn Pro Ile Ser Lys Ala Lys Leu Asp Lys Asp Gly Met
        195                 200                 205 tat cca gtt gaa atc tgg cat cca gat cca gca aaa aat gag aac aca      672
Tyr Pro Val Glu Ile Trp His Pro Asp Pro Ala Lys Asn Glu Asn Thr
210                 215                 220 agg tac ttt ggc aat tac act gga ggc acg tgc acc cca ccc gtc ctg      720
Arg Tyr Phe Gly Asn Tyr Thr Gly Gly Thr Cys Thr Pro Pro Val Leu
225                 230                 235                 240 cag ttc aca aac acc ctg aca act gtg ctc cta gat gaa aat gga gtt      768
Gln Phe Thr Asn Thr Leu Thr Thr Val Leu Leu Asp Glu Asn Gly Val
            245                 250                 255 ggg ccc ctc agc aaa gga gaa ggt cta tac ctc tcg agc gta gat ata      816
Gly Pro Leu Ser Lys Gly Glu Gly Leu Tyr Leu Ser Ser Val Asp Ile
        260                 265                 270 atg ggc tgg aga gtt aca aga aac tat gat gtc cat cac tgg aga ggg      864
Met Gly Trp Arg Val Thr Arg Asn Tyr Asp Val His His Trp Arg Gly
    275                 280                 285 ctt ccc aga tat ttc aaa atc acc ctg aga aaa aga tgg gtc aaa aat      912
Leu Pro Arg Tyr Phe Lys Ile Thr Leu Arg Lys Arg Trp Val Lys Asn
290                 295                 300 ccc tat ccc atg gcc tcc ctc ata agt tcc ctt ttc aac aac atg ctc      960
Pro Tyr Pro Met Ala Ser Leu Ile Ser Ser Leu Phe Asn Asn Met Leu
305                 310                 315                 320 ccc caa gtg cag ggc caa ccc atg gaa ggg gag aac acc cag gta gag     1008
Pro Gln Val Gln Gly Gln Pro Met Glu Gly Glu Asn Thr Gln Val Glu
            325                 330                 335 gag gtt aga gtg tat gat ggg act gaa cct gta ccg ggg gac cct gat     1056
Glu Val Arg Val Tyr Asp Gly Thr Glu Pro Val Pro Gly Asp Pro Asp
        340                 345                 350 atg acg cgc tat gtt gac cgc ttt gga aaa aca aag act gta ttt cct     1104
Met Thr Arg Tyr Val Asp Arg Phe Gly Lys Thr Lys Thr Val Phe Pro
    355                 360                 365 ccc ggg                                                              1110
Pro Gly
    370
```

<210> SEQ ID NO 19
<211> LENGTH: 370
<212> TYPE: PRT
<213> ORGANISM: Artificial Sequence
<220> FEATURE:
<223> OTHER INFORMATION: Description of Artificial Sequence:
    PyVP1-3C-[N-14] variant of polyomavirus VP1 protein shortened 14
    residues at N-terminus, with 4 of 6 Cys replaced
    by Ser and exchange of Thr 235 to Cys

<400> SEQUENCE: 19

```
Met Ser Thr Lys Ala Cys Pro Arg Pro Ala Pro Val Pro Lys Leu Leu
1               5                   10                  15

Ile Lys Gly Gly Met Glu Val Leu Asp Leu Val Thr Gly Pro Asp Ser
                20                  25                  30

Val Thr Glu Ile Glu Ala Phe Leu Asn Pro Arg Met Gly Gln Pro Pro
            35                  40                  45

Thr Pro Glu Ser Leu Thr Glu Gly Gly Gln Tyr Tyr Gly Trp Ser Arg
        50                  55                  60

Gly Ile Asn Leu Ala Thr Ser Asp Thr Glu Asp Ser Pro Gly Asn Asn
65                  70                  75                  80

Thr Leu Pro Thr Trp Ser Met Ala Lys Leu Gln Leu Pro Met Leu Asn
```

-continued

```
                85                  90                  95
Glu Asp Leu Thr Cys Asp Thr Leu Gln Met Trp Glu Ala Val Ser Val
            100                 105                 110
Lys Thr Glu Val Val Gly Ser Gly Ser Leu Leu Asp Val His Gly Phe
        115                 120                 125
Asn Lys Pro Thr Asp Thr Val Asn Thr Lys Gly Ile Ser Thr Pro Val
    130                 135                 140
Glu Gly Ser Gln Tyr His Val Phe Ala Val Gly Gly Glu Pro Leu Asp
145                 150                 155                 160
Leu Gln Gly Leu Val Thr Asp Ala Arg Thr Lys Tyr Lys Glu Glu Gly
                165                 170                 175
Val Val Thr Ile Lys Thr Ile Thr Lys Lys Asp Met Val Asn Lys Asp
            180                 185                 190
Gln Val Leu Asn Pro Ile Ser Lys Ala Lys Leu Asp Lys Asp Gly Met
        195                 200                 205
Tyr Pro Val Glu Ile Trp His Pro Asp Pro Ala Lys Asn Glu Asn Thr
    210                 215                 220
Arg Tyr Phe Gly Asn Tyr Thr Gly Gly Thr Cys Thr Pro Pro Val Leu
225                 230                 235                 240
Gln Phe Thr Asn Thr Leu Thr Thr Val Leu Leu Asp Glu Asn Gly Val
                245                 250                 255
Gly Pro Leu Ser Lys Gly Glu Gly Leu Tyr Leu Ser Ser Val Asp Ile
            260                 265                 270
Met Gly Trp Arg Val Thr Arg Asn Tyr Asp Val His His Trp Arg Gly
        275                 280                 285
Leu Pro Arg Tyr Phe Lys Ile Thr Leu Arg Lys Arg Trp Val Lys Asn
    290                 295                 300
Pro Tyr Pro Met Ala Ser Leu Ile Ser Ser Leu Phe Asn Asn Met Leu
305                 310                 315                 320
Pro Gln Val Gln Gly Gln Pro Met Glu Gly Glu Asn Thr Gln Val Glu
                325                 330                 335
Glu Val Arg Val Tyr Asp Gly Thr Glu Pro Val Pro Gly Asp Pro Asp
            340                 345                 350
Met Thr Arg Tyr Val Asp Arg Phe Gly Lys Thr Lys Thr Val Phe Pro
        355                 360                 365
Pro Gly
    370
```

<210> SEQ ID NO 20
<211> LENGTH: 1152
<212> TYPE: DNA
<213> ORGANISM: Artificial Sequence
<220> FEATURE:
<223> OTHER INFORMATION: Description of Artificial Sequence:PyVP1-3C
      variant of polyomavirus VP1 protein with 4 of 6
      Cys replaced by Ser and exchange of Thr 249 to Cys
<220> FEATURE:
<221> NAME/KEY: CDS
<222> LOCATION: (1)..(1152)
<223> OTHER INFORMATION: PyVP1-3C variant

<400> SEQUENCE: 20

```
atg gcc ccc aaa aga aaa agc ggc gtc tct aaa agc gag aca aaa agc    48
Met Ala Pro Lys Arg Lys Ser Gly Val Ser Lys Ser Glu Thr Lys Ser
  1               5                  10                  15 aca aag gcc tgt cca aga ccc gca ccc gtt ccc aaa ctg ctt att aaa    96
Thr Lys Ala Cys Pro Arg Pro Ala Pro Val Pro Lys Leu Leu Ile Lys
             20                  25                  30
```

| | | |
|---|---|---|
| ggg ggt atg gag gtg ctg gac ctt gtg aca ggg cca gac agt gtg aca<br>Gly Gly Met Glu Val Leu Asp Leu Val Thr Gly Pro Asp Ser Val Thr<br>         35                       40                        45 | | 144 |
| gaa ata gaa gct ttt ctg aac ccc aga atg ggg cag cca ccc acc cct<br>Glu Ile Glu Ala Phe Leu Asn Pro Arg Met Gly Gln Pro Pro Thr Pro<br> 50                       55                       60 | | 192 |
| gaa agc cta aca gag gga ggg caa tac tat ggt tgg agc aga ggg att<br>Glu Ser Leu Thr Glu Gly Gly Gln Tyr Tyr Gly Trp Ser Arg Gly Ile<br> 65                       70                       75                       80 | | 240 |
| aat ttg gct aca tca gat aca gag gat tcc cca gga aat aat aca ctt<br>Asn Leu Ala Thr Ser Asp Thr Glu Asp Ser Pro Gly Asn Asn Thr Leu<br>                       85                       90                       95 | | 288 |
| ccc aca tgg agt atg gca aag ctc cag ctt ccc atg ctc aat gag gac<br>Pro Thr Trp Ser Met Ala Lys Leu Gln Leu Pro Met Leu Asn Glu Asp<br>                100                      105                     110 | | 336 |
| ctc acc tgt gac acc cta caa atg tgg gag gca gtc tca gtg aaa acc<br>Leu Thr Cys Asp Thr Leu Gln Met Trp Glu Ala Val Ser Val Lys Thr<br>                115                      120                     125 | | 384 |
| gag gtg gtg ggc tct ggc tca ctg tta gat gtg cat ggg ttc aac aaa<br>Glu Val Val Gly Ser Gly Ser Leu Leu Asp Val His Gly Phe Asn Lys<br>      130                      135                     140 | | 432 |
| ccc aca gat aca gta aac aca aaa gga att tcc act cca gtg gaa ggc<br>Pro Thr Asp Thr Val Asn Thr Lys Gly Ile Ser Thr Pro Val Glu Gly<br>145                     150                      155                     160 | | 480 |
| agc caa tat cat gtg ttt gct gtg ggc ggg gaa ccg ctt gac ctc cag<br>Ser Gln Tyr His Val Phe Ala Val Gly Gly Glu Pro Leu Asp Leu Gln<br>                165                      170                     175 | | 528 |
| gga ctt gtg aca gat gcc aga aca aaa tac aag gaa gaa ggg gta gta<br>Gly Leu Val Thr Asp Ala Arg Thr Lys Tyr Lys Glu Glu Gly Val Val<br>      180                      185                     190 | | 576 |
| aca atc aaa aca atc aca aag aag gac atg gtc aac aaa gac caa gtc<br>Thr Ile Lys Thr Ile Thr Lys Lys Asp Met Val Asn Lys Asp Gln Val<br>                195                      200                     205 | | 624 |
| ctg aat cca att agc aag gcc aag ctg gat aag gac gga atg tat cca<br>Leu Asn Pro Ile Ser Lys Ala Lys Leu Asp Lys Asp Gly Met Tyr Pro<br>      210                      215                     220 | | 672 |
| gtt gaa atc tgg cat cca gat cca gca aaa aat gag aac aca agg tac<br>Val Glu Ile Trp His Pro Asp Pro Ala Lys Asn Glu Asn Thr Arg Tyr<br>225                   230                      235                     240 | | 720 |
| ttt ggc aat tac act gga ggc acg tgc acc cca ccc gtc ctg cag ttc<br>Phe Gly Asn Tyr Thr Gly Gly Thr Cys Thr Pro Pro Val Leu Gln Phe<br>                245                      250                     255 | | 768 |
| aca aac acc ctg aca act gtg ctc cta gat gaa aat gga gtt ggg ccc<br>Thr Asn Thr Leu Thr Thr Val Leu Leu Asp Glu Asn Gly Val Gly Pro<br>      260                      265                     270 | | 816 |
| ctc agc aaa gga gaa ggt cta tac ctc tcg agc gta gat ata atg ggc<br>Leu Ser Lys Gly Glu Gly Leu Tyr Leu Ser Ser Val Asp Ile Met Gly<br>                275                      280                     285 | | 864 |
| tgg aga gtt aca aga aac tat gat gtc cat cac tgg aga ggg ctt ccc<br>Trp Arg Val Thr Arg Asn Tyr Asp Val His His Trp Arg Gly Leu Pro<br>      290                      295                     300 | | 912 |
| aga tat ttc aaa atc acc ctg aga aaa aga tgg gtc aaa aat ccc tat<br>Arg Tyr Phe Lys Ile Thr Leu Arg Lys Arg Trp Val Lys Asn Pro Tyr<br>305                     310                      315                     320 | | 960 |
| ccc atg gcc tcc ctc ata agt tcc ctt ttc aac aac atg ctc ccc caa<br>Pro Met Ala Ser Leu Ile Ser Ser Leu Phe Asn Asn Met Leu Pro Gln<br>                325                      330                     335 | | 1008 |
| gtg cag ggc caa ccc atg gaa ggg gag aac acc cag gta gag gag gtt<br>Val Gln Gly Gln Pro Met Glu Gly Glu Asn Thr Gln Val Glu Glu Val | | 1056 |

```
                 340                 345                 350
aga gtg tat gat ggg act gaa cct gta ccg ggg gac cct gat atg acg     1104
Arg Val Tyr Asp Gly Thr Glu Pro Val Pro Gly Asp Pro Asp Met Thr
        355                 360                 365 cgc tat gtt gac cgc ttt gga aaa aca aag act gta ttt cct ccc ggg     1152
Arg Tyr Val Asp Arg Phe Gly Lys Thr Lys Thr Val Phe Pro Pro Gly
    370                 375                 380

<210> SEQ ID NO 21
<211> LENGTH: 384
<212> TYPE: PRT
<213> ORGANISM: Artificial Sequence
<220> FEATURE:
<223> OTHER INFORMATION: Description of Artificial Sequence:PyVP1-3C
      variant of polyomavirus VP1 protein with 4 of 6
      Cys replaced by Ser and exchange of Thr 249 to Cys

<400> SEQUENCE: 21

Met Ala Pro Lys Arg Lys Ser Gly Val Ser Lys Ser Glu Thr Lys Ser
  1               5                  10                  15

Thr Lys Ala Cys Pro Arg Pro Ala Pro Val Pro Lys Leu Leu Ile Lys
             20                  25                  30

Gly Gly Met Glu Val Leu Asp Leu Val Thr Gly Pro Asp Ser Val Thr
         35                  40                  45

Glu Ile Glu Ala Phe Leu Asn Pro Arg Met Gly Gln Pro Pro Thr Pro
     50                  55                  60

Glu Ser Leu Thr Glu Gly Gly Gln Tyr Tyr Gly Trp Ser Arg Gly Ile
 65                  70                  75                  80

Asn Leu Ala Thr Ser Asp Thr Glu Asp Ser Pro Gly Asn Asn Thr Leu
                 85                  90                  95

Pro Thr Trp Ser Met Ala Lys Leu Gln Leu Pro Met Leu Asn Glu Asp
            100                 105                 110

Leu Thr Cys Asp Thr Leu Gln Met Trp Glu Ala Val Ser Val Lys Thr
        115                 120                 125

Glu Val Val Gly Ser Gly Ser Leu Leu Asp Val His Gly Phe Asn Lys
    130                 135                 140

Pro Thr Asp Thr Val Asn Thr Lys Gly Ile Ser Thr Pro Val Glu Gly
145                 150                 155                 160

Ser Gln Tyr His Val Phe Ala Val Gly Gly Glu Pro Leu Asp Leu Gln
                165                 170                 175

Gly Leu Val Thr Asp Ala Arg Thr Lys Tyr Lys Glu Glu Gly Val Val
            180                 185                 190

Thr Ile Lys Thr Ile Thr Lys Lys Asp Met Val Asn Lys Asp Gln Val
        195                 200                 205

Leu Asn Pro Ile Ser Lys Ala Lys Leu Asp Lys Asp Gly Met Tyr Pro
    210                 215                 220

Val Glu Ile Trp His Pro Asp Pro Ala Lys Asn Glu Asn Thr Arg Tyr
225                 230                 235                 240

Phe Gly Asn Tyr Thr Gly Gly Thr Cys Thr Pro Pro Val Leu Gln Phe
                245                 250                 255

Thr Asn Thr Leu Thr Thr Val Leu Leu Asp Glu Asn Gly Val Gly Pro
            260                 265                 270

Leu Ser Lys Gly Glu Gly Leu Tyr Leu Ser Ser Val Asp Ile Met Gly
        275                 280                 285

Trp Arg Val Thr Arg Asn Tyr Asp Val His His Trp Arg Gly Leu Pro
    290                 295                 300
```

```
Arg Tyr Phe Lys Ile Thr Leu Arg Lys Arg Trp Val Lys Asn Pro Tyr
305                 310                 315                 320

Pro Met Ala Ser Leu Ile Ser Ser Leu Phe Asn Asn Met Leu Pro Gln
            325                 330                 335

Val Gln Gly Gln Pro Met Glu Gly Glu Asn Thr Gln Val Glu Val
        340                 345                 350

Arg Val Tyr Asp Gly Thr Glu Pro Val Pro Gly Asp Pro Asp Met Thr
        355                 360                 365

Arg Tyr Val Asp Arg Phe Gly Lys Thr Lys Thr Val Phe Pro Pro Gly
    370                 375                 380
```

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:specific
      binding motif of proline-rich ligand in WW domain
      Type III

<400> SEQUENCE: 22

```
Pro Pro Leu Pro
  1
```

<210> SEQ ID NO 23
<211> LENGTH: 31
<212> TYPE: PRT
<213> ORGANISM: Artificial Sequence
<220> FEATURE:
<223> OTHER INFORMATION: Description of Artificial Sequence:WW domain

<400> SEQUENCE: 23

```
Gly Ser Gly Trp Thr Glu His Lys Ser Pro Asp Gly Arg Thr Tyr Tyr
  1               5                  10                  15

Tyr Asn Thr Glu Thr Lys Gln Ser Thr Trp Glu Lys Pro Asp Asp
             20                  25                  30
```

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence:
      oligonucleotide primer vp1-NImp

<400> SEQUENCE: 24
tatacatatg gcccccaaaa gaaaaagc        28

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence:
      oligonucleotide primer vp1CImp

<400> SEQUENCE: 25
atatcccggg aggaaataca gtctttgttt ttcc        34

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence:

```
       oligonucleotide for cloning in NdeI-EcoRI sites of
       highly-expressing pET-vector with T7lac promoter

<400> SEQUENCE: 26
atatgaattc cagtcattga agctgccaca agg                                  33

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence:
       oligonucleotide FBP11-WWaN

<400> SEQUENCE: 27
atactcttca ggcagcggct ggacagaaca taaatcacct gatgg                     45

<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence:
       oligonucleotide FBP11-WWaC

<400> SEQUENCE: 28
atactcttct accactacca tcatccggct tttcccaggt agactg                    46

<210> SEQ ID NO 29
<211> LENGTH: 47
<212> TYPE: DNA
<213> ORGANISM: Artificial Sequence
<220> FEATURE:
<223> OTHER INFORMATION: Description of Artificial Sequence:
       oligonucleotide vp1-150-WWaC

<400> SEQUENCE: 29
atactcttca ggtagcggcg taaacacaaa aggaatttcc actccag                   47

<210> SEQ ID NO 30
<211> LENGTH: 46
<212> TYPE: DNA
<213> ORGANISM: Artificial Sequence
<220> FEATURE:
<223> OTHER INFORMATION: Description of Artificial Sequence:
       oligonucleotide vp1-150-WWaN

<400> SEQUENCE: 30
atactcttca gccgctgcct gtatctgtcg gtttgttgaa cccatg                    46

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence:
       oligonucleotide for PCR amplification of WW domain with NdeI
       interface

<400> SEQUENCE: 31
aatatatcat atgtccatca tccggctttt cccaggtaga ct                        42

<210> SEQ ID NO 32
<211> LENGTH: 45
<212> TYPE: DNA
<213> ORGANISM: Artificial Sequence
<220> FEATURE:
```

<223> OTHER INFORMATION: Description of Artificial Sequence:
      oligonucleotide for PCR amplification of WW domain

<400> SEQUENCE: 32
tattaatcat atgagcggct ggacagaaca taaatcacct gatgg          45

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence:
      oligonucleotide for PCR on PyVP1 genetic fragment

<400> SEQUENCE: 33
gcgcgcgcat atgagcacca aggctagccc aagacccg          38

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence:
      oligonucleotide with Nde I-cutting site

<400> SEQUENCE: 34
ttatttacat atggtgagca agggcgagga g          31

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence:
      oligonucleotide with Afl II cutting site

<400> SEQUENCE: 35
atatcttaag tacagctcgt ccatgccg          28

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence:proline-rich
      sequence

<400> SEQUENCE: 36

Pro Pro Pro Pro Pro Pro Pro Pro Leu Pro
 1               5                  10

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence:
      oligonucleotide for PCR on vector pEGFP-N1

<400> SEQUENCE: 37
tatagctagc gtgagcaagg gcgaggagct gttc          34

<210> SEQ ID NO 38
<211> LENGTH: 28
<212> TYPE: DNA
<213> ORGANISM: Artificial Sequence
<220> FEATURE:

```
<223> OTHER INFORMATION: Description of Artificial Sequence:
      oligonucleotide for PCR on vector pEGFP-N1

<400> SEQUENCE: 38
gggaattaag tacagctcgt ccatgccg                                            28
```

METHOD FOR LINKING MOLECULAR SUBSTANCES

CROSS-REFERENCES TO RELATED APPLICATIONS

This application is a continuation of U.S. application Ser. No. 10/129,315 filed Nov. 4, 2002, which is a US National Phase Application Under 35 U.S.C. 371 of International Application No. PCT/EP2000/010873 filed Nov. 3, 2000, which claims the priority of German Application No. 19952956.6 filed Nov. 3, 1999, and the contents of each of which are incorporated herein by reference in their entirety.

BRIEF SUMMARY OF THE INVENTION

The present invention concerns a process for the connection of two or more molecular substances by adapter segments which cause a directed interaction, based on the affinity of proline-rich amino acid sequences and protein domains of the type WW.

The interaction of two or more molecular substances is a frequent problem within the realm of biotechnological and pharmaceutical-medical research, development, and application. In particular, the interactions of two or more proteins or peptides as molecular substances are usually considered thereby. Such interactions are often explored as part of biochemical and cellular biological research, for instance, as with intra- and intercellular communication, signal transduction on a molecular level, or analyses of protein-protein interactions (amongst others, in the usage of two-hybrid systems and processes derived therefrom). Moreover, the association of biomolecules, particularly of two or more proteins, for in vitro synthesis of fusion proteins is of great importance for many biotechnological processes. Fusion proteins generated in such a way can be, for instance, heterobifunctional (bivalent) antibodies (so-called diabodies; see O. Perisic, P. A. Webb, P. Holliger, G. Winters & R. L. Williams, Crystal structure of a diabody, a bivalent antibody fragment, *Structure* 2, pp. 1217-1226, 1994), which comprise the binding domains (Fab/Fv/scFv fragments) of two distinct antibodies. If thereby both valences are, for instance, directed respectively at tumor cells or natural killer cells, then the bivalent, hybrid fusion protein can accordingly mediate an attachment of killer cells onto tumor cells. In the case of immunotoxins, antibodies are coupled with toxic substances and the cytotoxin is directed through specific antigen-antibody interaction into predefined cell types (see M. A. Ghetie & E. S. Vitetta, Recent developments in immunotoxin therapy, *Curr. Opin. Immunol.* 6, pp. 707-714, 1994).

With the help of fusion constructs and assemblates of various proteins, fundamentally any effectors can be combined with each other, and through appropriate interactions with antigens or other biological effects, two functions or characteristics can be achieved in a hybrid molecule. A series of examples hereof are published (J. P. McGrath, X. Cao, A. Schutz, P. Lynch, T. Ebendal, M. J. Coloma, S. L. Morrison & S. D. Putney, Bifunctional fusion between nerve growth factor and a transferrin receptor antibody, *J. Neurosci. Res.* 47, pp. 123-133, 1997; J. M. Betton, J. P. Jacob, M. Hofnung, J. K. Broome-Smith, Creating a bifunctional protein by insertion of beta-lactamase into the maltodextrin-binding protein, *Nat. Biotechnol.* 15, pp. 1276-1279, 1997; Y. Maeda, H. Ueda, T. Hara, J. Kazami, G. Kawano, E. Suzuki & T. Nagamune, expression of a bifunctional chimeric protein A-*Vargula hilgendorfii* luciferase in mammalian cells, *Biotechniques* 20, pp. 116-121, 1996; W. Wels, I. M. Harwerth, M. Zwickl, N. Hardman, B. Groner & N. E. Hynes, Construction, bacterial expression and characterization of a bifunctional single-chain antibody-phosphatase fusion protein targeted to the human erbB-2 receptor, *Biotechnology* (N.Y.) 10, pp. 1128-1132, 1992).

Heterobifunctional constructs are frequently produced through synthesis of fusion proteins at the gene level. This generally presupposes suitable connection elements (linkers) between both partners, as well as accessible termini of the polypeptide chains. In unfavorable cases, fusion of the partners can lead to the product of the fusion being inactive, for example because the fusion protein cannot develop a correct three-dimensional folding topology. Thus, it is often desirable that the connection of both fusion partners occurs in vitro, that is, after the separate synthesis and folding of both partners. Such a process would also allow, for instance, the fast production and analysis of various combinations of single components, without requiring new genetic constructions each time. For the fusion of these components, adapter segments are necessary, through which the process of fusion or directed association of the partners involved is isolated from their production. Furthermore, it is thereby necessary that the adapter segments (domains or peptide sequences) are locked onto the involved partners firmly without otherwise changing their specific characteristics.

In other applications, it is desired that a short-term, but strong, interaction results between two molecular species. Thereby, peptides and small protein domains play an especially important role, since in the process of recombinant production of proteins, they can be placed comparatively easily on the desired target proteins. Applications of this are, for instance, the purification of recombinantly produced proteins through specific binding segments. Often, a polyhistidine peptide segment is utilized for binding to nickel chelate columns (see P. Hengen, Purification of His-Tag fusion proteins from *Escherichia coli*, trends Biochem. Sci. 20, pp. 285-286, 1995), or the binding of a peptide segment known as Strep-Tag to Streptavidin (T. G. Schmidt, J. Koepke, R. Frank & A. Skerra, Molecular interaction between the Strep-tag affinity peptide and its cognate target, streptavidin, *J. Mol. Biol.* 255, pp. 753-766, 1996). The His-Tag process has the disadvantage, however, that the polyhistidine peptide segment can only bind to structures containing nickel ions; the connection, for instance, of two natural proteins or peptides is not possible in this way. For the connection of molecular substances, the process is hence not, or only in exceptions, suitable. In preparations that are purified in this manner, one also often finds nickel ions in the solution, which makes the system unattractive for medical-therapeutic applications. With the Strep-Tag process, the region of the binding partners that mediates binding is relatively large, so that for steric reasons it is not suitable for many connections. Additionally, avidin and streptavidin each possess four binding sites, so that a regulated formation of two different linked molecular substances in solution is very difficult.

Apart from use in the purification of proteins labeled in such a way, the immobilization of proteins on a solid, inert matrix is also of high biotechnological significance, for instance with the refolding of proteins on a matrix for the prevention of aggregation processes during folding (see G. Stempfer, B. Höll-Neugebauer & R. Rudolph, Improved refolding of an immobilized fusion protein, *Nat. Biotechnol.* 14, pp. 329-334, 1996), or the immobilization of an enzyme in a bioreactor. Polyionic sequences which have been used up to this time in the aforementioned process have the disadvantage, however, that their interaction is significantly disturbed by the presence of polyions, for instance DNA in the solution, or also through various solvent additives.

The purpose of the invention at hand is to provide a process for the connection of molecular substances that does not exhibit the mentioned disadvantages of the current technology.

This is accomplished in accordance with the invention through a process based upon claim 1 for the connection of two or more molecular substances with each other across adapter segments, distinguished in that one of the molecular substances is modified in such a way that as an adapter segment it displays, in at least one area, a WW domain or a structure derived therefrom, another molecular substance is modified in such a way that as an adapter segment it displays, in at least one area, a proline-rich sequence which binds at the WW domain or a structure derived therefrom, and the molecular substances, through the association of WW domains or structures derived therefrom and of a proline-rich sequence, come into interaction with each other in order to achieve binding of one another.

Advantageous forms of execution emerge in the secondary claims and description.

BRIEF DESCRIPTION OF THE DRAWINGS

The following figures are referred to in the description and the examples.

FIG. 1 shows a schematic representation of the invention. Adapter segments based on the interaction of proline-rich substances with WW domains and forms derived therefrom are employed. (a) linkage of two molecular species A and B through adapter segments. (b) linkage of two molecular species A and B, analogous to (a), however with additional disulfide bridging for covalent linkage of the partners. (c) matrix-immobilization of a molecular substance through the adapter segments (one the molecules represents the matrix or a part of the matrix). The adapter segments can be attached to the molecules at the ends (termini) as well as in the form of insertions.

FIG. 2 shows in (a) a comparison, by means of SDS-PAGE, of the protein masses and the purification efficiencies of different variants of polyoma virus protein VP1, the PyVP1-CallS-T249C variant (comparable to the wild type of the protein) and the PyVP1-WW150 variant, in which a WW domain is inserted in a loop in the vicinity of amino acid position 150. Production and purification of the variants is comprehensively described in example 1. With both variants, degradation products of the protein that exhibit a smaller molecular mass are usually noted to appear. (b) circular dichroism spectra (CD) of the PyVP1-WW150 variant and the PyVP1-CallS-T249C variant. The inserted WW domain at position 150 exhibits a native folding, whereby the β-sheet proportion in the CD-spectrum rises.

FIG. 3 shows the binding of PyVP1-WW150 on a sensor chip with an immobilized proline-rich peptide, according to example 2. The three measurements, based on surface plasmon-resonance, show that the solvent additives exert only minor influence on affinity and specificity of the interaction, with the additives used in (b) and (c) each representing complex physiological mixed substances. (a) binding of PyVP1-WW150 to the sensor's surface under normal solvent conditions. (b) binding of PyVP1-WW150 to the sensor's surface under application of Dulbecco's PBS as running buffer. (c) binding of PyVP1-WW150 to the sensor's surface with addition of fetal calf serum (FCS) as a model for the mixture of biologically relevant substances.

FIG. 4 shows an SDS gel for illustration of the specific binding of PyVP1-WW150 to a matrix containing proline peptide. Lane 1: application VP1-WW150 (purified as in example 1); lane 2 and lane 3: different wash fractions; lane 4 and lane 5: elution fractions with 1% SDS in the elution buffer; lane 6: 10 kDa molecular mass marker. The example shows that WW domain-containing proteins can be reversibly immobilized on a matrix. The detected double band of the PyVP1 variant depicts the native protein, as well as a proteolytic degradation product of the protein, which usually appears in all preparations.

FIG. 5 shows a gel filtration (TSK gel G5000PWXL, TosoHaas) for the demonstration of the binding of a proline-rich peptide to the surface of a virus-like capsid, with the WW domains inserted into VP1 and exposed on the surface of the capsid. Assembly of the PyVP1-WW150 protein into a capsid takes place under the conditions indicated in example 4. A proline-rich peptide can be bound onto the virus-like capsids, which is verified through the specific absorption of a dye coupled to it. Left above: Proof of capsid formation through absorption at 260 and 280 nm; the capsids elute at a volume of 6 to 8 ml, the non-assembled, free pentamers appear at 9 to 10 ml. Left below: Absorption of the fluorescence-labeled peptide at 490 nm; the elution takes place parallel to the capsid elution and the pentamer elution at 6 to 10 ml. Above 10 ml, surplus free peptide elutes along with the fluorescence dye. Right above: The free, unbound peptide shows no interaction with the matrix and elutes exclusively above 10 ml. Right below: Superimposition of the chromatograms from the left above and the left below, for illustration of the coelution of the bound peptide with the capsid fraction.

FIG. 6 shows in (a) the purification of variants PyVP1-3C-WW1 and PyVP1-3C-WW[N-14]. The SDS gel (12%) exhibits the PyVP1 protein without WW domain (lane 2), the PyVP1-WW150 variant from example 1 (lane 3), as well as both variants from example 8 (PyVP1-3C-WW1 on lane 4 and lane 5, PyVp1-3C-WW[N-14] on lane 6). Lane 1 and lane 7, standard molecular mass (10 kDa ladder). (b) purification of the GFP variant GFP-PLP, and illustration on an SDS gel (15%). Lane M, molecular weight marker (10 kDa ladder); lane Int, wash fraction of the intein affinity column; fractions 1 to 9, various elution fractions the GFP-PLP-Proteins.

FIG. 7 shows the packaging of molecular substances in the interior of virus-like coats on the basis of polyoma virus VP1 variants. (a) wrapping of GFP-PLP in coats which contain PyVP1-3C-WW1. GFP-PLP is added before assembly under standard conditions in six-fold molar excess. A gel filtration experiment (TSK gel G6000PWXL, TosoHaas) is shown in which capsid fractions (elution at 9 ml) are detached from free, non-assembled pentamers of PyVP1 variants as well as from the GFP protein (11 to 13 ml). A detectable quantity of GFP, which was directed into the interior of the capsid through the WW domain/polyproline interaction, is present in the capsid fraction. (b) encapsidation of GFP inside of virus-like capsids with WW domain at the N-terminus, assembled from PyVP1-3C-[N-14]-PLP (proline-rich sequence at the shortened N-terminus). Analogous to the example in (a), GFP-WW1 is incubated with PyVP1-3C-[N-14]-PLP and capsids are produced through assembly under standard conditions. The polyproline peptides, through affinity to the WW domain, are thereby brought into the interior of the capsids. (c) encapsidation of a fluorescence-marked peptide (proline-rich sequence) in the interior of virus-like capsids. Analogous to the example in (a), the peptide is incubated with PyVP1-3C-WW[N-14] and capsids are produced through assembly under standard conditions. The polyproline peptides, through affinity to the WW domain, are thereby brought into the interior of the capsids. (d) wrapping of GFP with proline-rich sequence at the C-terminus inside of virus-like capsids, which are assembled with PyVP1-3C-WW[N-14]. Analogous to the example in (a), GFP-PLP is incubated with PyVP1-3C-WW [N-14] and capsids are produced through assembly under standard conditions. The GFP-PLP, through affinity to the WW domain, is thereby brought into the interior of the capsids.

FIG. 8 shows an SDS gel for illustration of the purification of proteins with WW domain from a mixed substance, here a cellular extract. Lane 1: 10 kDa molecular weight marker; lane 2: crude extract of (PyVP1-3C-WW1)-intein-CBD fusion protein; lane 3: run-through; bands 4 to 10: various fractions of the elution of the fusion protein, with 2% SDS in the elution buffer. Immobilization of the fusion protein here takes place through a column with a covalently bound proline-rich peptide. After application of the crude extract, the column is washed with a total of 10 column volumes of a buffer that contains 2 M NaCl. Besides the fusion protein, degradation products therefrom are detected, as well as molecular chaperones, which are known to bind to PyVP1.

FIG. 9 shows the disulfide bridging of a molecular substance with a WW domain, which was fused to Glutathion-S-Transferase (GST) for the purpose of affinity purification. For bridging, two variants of a WW domain were used, at which an amino acid was exchanged for a cysteine at one position of each. That is, for one, the variant D8C, on which the aspartate was exchanged at position 8 in the WW domain for cysteine and, for another, K19C, at which Lysine19 was replaced with cysteine. The molecular substance here is a proline-rich peptide with the sequence $CSGP_8LP$ (SEQ ID NO:15), which was marked with a fluorescence dye (Oregon Green, OG, Firma Molecular Probes) for the purpose of the analysis at the amino group of the N-terminus. The disulfide bridging was performed as described in example 7. In order to analyze the bridging, the sample was subjected to a reversed-phase HPLC (HPLC column: YMC protein-Rp $C_{18}$: running buffers A: 0,1% TFA in $H_2O$, running buffer B: 80% ACN, 0.1% TFA). According to these chromatographs, WW domain and free, non-bridged peptide could be separated from one another (elution times: peptide 12 min., WW domain 25-27 min.), while disulfide-bridged peptide and the WW domain almost coelute (28 min). By means of the fluorescence label of the peptides, the peptide can be detected along with the WW domain. FIG. 9(a) shows that this was the case for the WW domain-variant K19C, not however for D8C. The cause for this can lie in the steric inaccessibility of the cysteines of variant D8C. As proof of the WW-domain specificity of this bridging, the cysteine-free variant of the WW domain was analyzed in a parallel experiment, which likewise showed no bridging. FIG. 9(b) shows that the covalent interaction of the WW domain variant K19C and proline-rich peptide can be broken by addition of a reduction agent (50 mM DTT). The fluorescing peptide exists again thereafter completely in free form.

DETAILED DESCRIPTION OF THE INVENTION

The linkage of two or more different molecular substances (molecular species) into one—usually heterobifunctional—fusion construction is a process of high biotechnological and pharmaceutical interest. Usually, as part of the invention-compliant application, proteins and/or peptides are used as the molecule species to be joined, since the adapter segments of the invention at hand originate from this chemical class.

According to the invention, other molecular substances that possess one of the adapter segments of this invention are also usable. For instance, in compliance with the invention, a solid matrix can be loaded with a molecular substance over the specified adapter segments. Often, both substances to be joined must be stably and covalently linked with each other. Conversely, for some applications it can also be desired that the interaction between both molecular species exists only for a limited time and can be quickly dissolved again, for instance through extraneous additives. In yet other applications, a molecule species must be immobilized for a limited time, hence interact in a specific way with a matrix, for instance for the purification of a protein from a crude cellular extract in the recombinant production of a protein, or for a matrix-supported refolding of the protein. For such applications, the invention at hand is appropriate.

Compliant with the invention, a protein can, for instance, be directed into the interior of a virus-like coat for wrapping, or two or more different proteins can be joined into a chimeric protein with new characteristics, for instance as bivalent antibodies. Analogously, this interaction can be used for the immobilization of a molecular species, for instance for the separation of this substance from a mixture of substances.

In addition to connection through adapter segments, which is based on the interaction between WW domain and proline-rich sequence, covalent linkage of the molecular substances with each other can take place. This covalent linkage, through disulfide bridging via cysteines artificially introduced at a suitable spatial site in both molecular substances, can thereby lead to a durable connection between both molecular substances. Via disulfide bridging, bifunctional fusion molecules can be generated which exist stably under physiological and all ordinary solvent conditions, and are thus also useful for medical, therapeutic, diagnostic, and biotechnological processes.

Possible application forms of the invention as described above are also presented in exemplary manner in FIG. 1.

For the connection of two or more molecular substances in compliance with the invention, the highly specific interaction of protein segments known under the term WW domain with a proline-rich peptide sequence (with a proline content of more than 50% within a short peptide succession of 2 to 6 amino acids) is exploited. These two molecular species show an unusually strong interaction with each other ($K_D$ 20 to 100 nM), when they are incubated together. The slow dissociation of the partners leads to the fact that the interaction is at first only temporarily effective. If this is unwanted, the dissociation can be prevented through the fixation of the binding partners by means of a disulfide bridge. Cysteines are artificially introduced in suitable spatial position into both adapter segments or within the region of the adapter segments. After association of the partners, the cysteine pairs can be oxidized through suitable choice of redox conditions and are, in this way, durably combined covalently with each other. The emerging hybrid fusion protein can display essential characteristics of the respectively underlying molecule species.

The WW domain is a small, globular protein domain, which usually consists of 30 to 40 amino acids (see M. Sudol, The WW Domain Binds Polyprolines and is Involved in Human Diseases, *Exp. & Mol. Medicine* 28, pp. 65-69, 1996), yet shorter variations are also known. WW domains display a high natural affinity to proline-rich ligands, which are bound with dissociation constants of 20 to 100 nM. The proline-rich ligands possess the minimum length necessary for binding of 5 to 15 amino acids with a proline content of more than 50% within this segment, whereby the direct interaction usually appears within a local segment of 2 to 6 amino acids (with more than 50% proline content). Natural ligands are thereby almost exclusively proteins that contain proline-rich segments in their amino acid sequence, however proline-rich peptides are also specific ligands of WW domains.

The designation WW domain derives from the observation that two conserved tryptophan residues (abbreviated WW) appear with a spacing of 20 to 22 amino acids; the second tryptophan, and a series of chiefly likewise-conserved hydrophobic amino acids, thereby form the binding pocket for the proline-rich ligands. A conserved proline is often located with a spacing of 2 amino acids after the second tryptophan. A series of different WW domain-types are known, which are presently arranged in 4 classes and which distinguish themselves from one another, particularly in reference to the preferentially-bound peptic ligands. WW domains can, in principle, compete with the (structurally unrelated) SH3-domains for the binding of proline-rich ligands, yet the ligands of the SH3-domains display deviant consensus sequences, so that proline-rich peptide ligands can be derived, which are specifically bound by WW domains. Furthermore, the binding of WW domains to proline-rich ligands is usually stronger than that of SH3 domains. The following table gives an overview of types and ligand-binding qualities of the of WW domain proteins.

| WW domain type | Specific binding motif of the proline-rich ligands* | Example/Agent |
| --- | --- | --- |
| Type I | Pro-Pro-(arbitrary)-(Tyr) | YAP65, Pin1, Dystrophin |
| Type II | Pro-Pro-Leu-Pro (SEQ ID NO: 22) | FBP11, FE65 |
| Type III | Pro-Gly-Met | FBP21, PRP40 |
| Type IV | Phospho-Ser/phospho-Thr | Pin1, Nedd4 |

*in direct proximity to a proline-rich sequence (>50% proline content)

The transmutation of a WW domain from type I into one of type II, along with the consequent change in the specificity with reference to the proline-rich peptides, can be achieved, for instance, through the amino acid exchanges L14W and H16G in the WW-type I-domain sequence. The structure of an agent from class I (Yes associated protein, YAP) shows that this WW domain consists of three β-strands which form a β-sheet (see M. Macias, M. Hyvonen, E. Baraldi, J. Schultz, M. Sudol, M. Saraste & Mr. Oschkinat, The Structure of the WW Domain in Complex with a Proline-Rich Peptide, Nature 382, pp. 646-649, 1996). The ligand binding pocket is formed from the second β-strand of the beta sheet with cooperation from the second conserved tryptophan.

The most important biological role of WW domains evidently exists in intracellular signal transduction. WW domains furthermore have been implicated directly or indirectly with a number of diseases, for instance inherited Liddle's syndrome, muscular dystrophy, and Alzheimers disease; thus, they are the target of a series of therapeutic strategies. Finally, WW domains play a biological role in the embryonic development of kidneys and in the intracellular life cycle of retroviruses.

As part of this invention it was found that, astonishingly, WW domains can form a stable structure (folding topology) under ordinary solvent conditions, even if they are isolated from their original molecular context and are genetically fused in or, dependent on the situation, to other proteins, for instance a viral coat protein. This applies, for instance, to a WW domain from the class of formin binding proteins with an unusually small size of only 31 amino acids, which forms a stable structure (folding topology) under these conditions. Remarkably, the introduction under favorable conditions of the WW domain, along with linker segments consisting of the amino acids serine and glycine, into external loops of proteins evidently neither disturbs their folding, nor are the binding qualities of the WW domain thereby negatively influenced. It could be shown that this also applies to variants of the WW domain, in which for instance amino acids were exchanged with cysteine at specific positions. It can also be valid for additional structures derived from WW domains, as for instance several consecutive, strung-together WW domains whose contributions to bonding either respectively add up, or in favorable cases are synergistic, shortened or extended WW domains, or even WW domains with site-directed exchanges of individual amino acids which, dependent upon the desired application, can for example, bind more strongly or weakly at proline-rich sequences than the natural protein domains. Such altered domains can be obtained, for instance, through interaction screening by means of current phage display technology.

Proteins which possess an inserted (that is to say, introduced in suitable loop regions within the polypeptide chain of the host proteins) or fused on (located respectively at the N-terminus and/or at the C-terminus of the host protein) WW domain demonstrate a high affinity to proline-rich sequences. These proline-rich sequences can thereby be fused with other proteins, peptides, or other molecular substances. Two arbitrary molecule species can therewith be brought into contact by means of the appended interaction partners (WW domain and proline-rich sequence). This association rests first of all on a hydrophobic interaction mediated by the WW domain and the proline-rich ligand. This interaction can be adjusted, however, with regard to higher specificity and more flexible use, through enlistment of ionic interactions or the introduction of covalent links between WW domain and proline-rich ligand, for example. Thus through placement of additional amino acids which are differently charged, or through point mutations in or near the adapter segments, the aggregation of the proline-rich ligands with the WW domain can be strengthened or more specifically configured. A covalent disulfide bridging of both components allows, in turn, a lasting and firm bond of the adapter segments and the molecular substances joined thereto.

A connection of more than two molecular substances with each other in compliance with the invention is also possible.

The kinetic parameters of interaction, such as the dissociation constant ($k_D$) could be determined as part of the investigations by interaction measurements based on surface plasmon resonance measurements. With these, it can be shown that the interactions between WW domains and proline-rich peptide sequence are fundamentally suitable for the applications described in the invention at hand.

The nature of the interaction of adapter segments leads exclusively to the development of a heteromeric hybrid species, consisting of a part with WW domain and a part with a proline-rich sequence. The formation of homofunctional molecules (homodimers) can be excluded. Compared to other systems with comparable characteristics, the utilized WW domain has the advantage of being extraordinarily small and compact. Thereby it is clearly superior for many applications, for instance antigen antibody interactions, to other ligand binding domains (for example lipocalins and anticalins).

Furthermore, it could be shown that the introduction of cysteine residues at specific locations within the WW domain and in the proline-rich substrate can be used, beyond the interaction between WW domain and proline-rich sequence, to cause covalent coupling of the association partner and as a result to bring together the protein parts fused onto the adapter segments in a stable connection. Thus, a dissociation of the interaction partners can not result even under unfavorable conditions, for instance especially high or very low salt concentrations, or under physiologically extreme temperatures. For that, an exchange with cysteine is undertaken for example at position Asp8 (numbering follows the WW domain from the formin-binding protein FBP11) or alternatively at position Lys19. These positions are merely selected exemplary; the introduction of specific cysteines can also be useful and successful at other sites of the WW domain or the surroundings hereof, or in the proline-rich sequence or the surroundings hereof.

The particular advantage is that again only heterobifunctional species will be formed (heterodimers), since due to the strong interaction of proline-rich peptide and WW domain, only associates between both of these two adapter segments can at first be formed. The subsequent disulfide bridging under oxidizing conditions then leads to the directed formation of covalently bridged, heteromeric species. Due to the high local concentration (approximation) of cysteines in the associated form, the disulfide bridging can also be successful under slightly reducing conditions and can therewith take place with particular specificity. In contrast, in case of accidental disulfide bridging, that is to say without the necessary strong affinity of the adapter segments to one another (that is, in a non patent-compliant application), undesirable homodimers of both interaction partners would also be formed as byproducts under oxidizing conditions.

The procedure described in the invention at hand is suitable to attach arbitrary interaction partners together in solution (in vitro), whereby both a temporary as well as a lasting link of both partners is possible. Likewise, the procedure can be used to specifically separate proteins, peptides or other molecular substances, those of which are equipped with one of the two adapter types (WW domain or proline-rich sequence), from a mixture of substances. This takes place through reversible binding to a matrix that has bound the respective interaction partners covalently. The strong bond is effective insomuch that the molecules also adhere to the matrix under stringent solvent conditions. The process thereby allows, for instance, the fast and efficient purification of recombinant proteins from the crude cellular extract of bacteria or eukaryotic cells, on the condition that the recombinant (to be purified) molecule carries one of the two adapter segments (WW domain or proline-rich sequence) in fusion or as an insertion, while the corresponding counterpart to the adapter segment is immobilized at the fixed phase.

Likewise, this immobilization procedure is suitable to implement specific modifications or a refolding of the immobilized protein on the matrix, avoiding aggregation processes. Finally, with the invention at hand, applications are also possible in which a simple and stable immobilization of a molecular substance plays a key role, for instance in biosensors or in bioreactors (see R. S. Phadke, Biosensors and enzyme immobilized electrodes, *Biosystems* 27, pp. 203-206, 1992; M. Abdul-Mazid, Biocatalysis and immobilized enzyme/cell bioreactors. Promising techniques in bioreactor technology, *Biotechnology* (N.Y.) 11, pp. 690-695, 1993).

Apart from proteins and peptides, other substances can be used for the procedure described in the invention at hand. Thus peptide derivatives, peptide antibiotics, proteins with modified side chains such as fluorescence labels, alkylation, acetylation, disulfide mixtures with thiol-containing substances, and analogous changes can be deployed in a similar manner. Peptide or protein conjugates with carbohydrate, nucleic acid or lipid content can also be utilized in the procedure. Nucleic acids such as DNA, RNA, ribozyme, synthetic nucleic acids such as, for example, peptide nucleic acids, or hybrids thereof can likewise be coupled with an adapter segment, for example with chemical means. They are then likewise suitable to partake in an interaction with an analogous interaction partner. The only requirement is the stable attachment of one of the utilized adapter segments.

Within the realm of invention-compliant application, antibodies, antibody-analogous substances, enzymes, structural proteins, and capsomers of viruses or phages come in particular into consideration as proteins.

The insertion or attachment of proline-rich sequence or WW domain, or a structure derived therefrom, into or in a molecular substance can, in principle, take place at every site of the molecular substance, if the structure of the WW domain is not substantially influenced thereby. If applicable, it can be advantageous to implement the attachment or insertion under utilization of suitable linker segments, as described in example 1 for the protein PyVP1-WW150. In the case of insertion in proteins, it is expedient to seek out such areas of the protein structure in which no periodic secondary structural elements like α-helix or β-sheet exist. The insertion of WW domains or proline-rich sequences in protein structures takes place most favorably where turn areas or random coil areas of conventional definition exist.

The binding of both adapter segments to each other can be considered under the aspect of different physical interactions. Thus, a hydrophobic effect can dominate the interaction during stabilization of the interaction, as will be demonstrated in the following example 7. Other forms of interaction can however also contribute to binding, such as ionic interactions, ion-dipole interactions, dipole-dipole interactions, hydrogen bridge bonds, van der Waals forces, or dispersion forces. Ultimately, besides the aforementioned examples for non-covalent connections, a covalent connection of both molecular substances can also be brought about. Thereby a chemically stable atomic bond between two atoms of the interaction partners is created, preferably in the form of disulfide bridging of two participating cysteine side chains.

For immobilization of one of the adapter segments (WW domain or proline-rich sequence) the matrix can be charged, for instance, through the N-terminus of the proline-rich sequence or the WW domain (coupling through N-hydroxysuccinimide ester of the matrix) or through a thiol group of one of the cysteines contained in the proline-rich sequence or the WW domain (coupling of the matrix through iodacetamide group). As matrices, for example, agarose and agarose derivatives, agarose beads, sepharose, dextrans, carbohydrates, or similar polymer material come into consideration based on current technology.

Applications of this invention are demonstrated in the following examples, through which the extent of protection of the invention should not, however, be limited.

EXAMPLE 1

Insertion of a WW Domain in the Outer Segment of an In-Vitro Assembled, Virus-Like Protein Coat (PyVP1-WW150)

In the first example, a WW domain of the amino acid sequence Gly-Ser-Gly-Trp-Thr-Glu-His-Lys-Ser-Pro-Asp-Gly-Arg-Thr-Tyr-Tyr-Tyr-Asn-Thr-Glu-Thr-Lys-Gln-Ser-Thr-Trp-Glu-Lys-Pro-Asp-Asp (SEQ ID NO:23) is inserted in a specific loop of a viral coat protein. At the same time, a linker is additionally inserted before and after the WW domain, consisting of alternating Gly-Ser amino acids. In the given example, the employed viral core protein is the pentameric polyoma virus VP1 core protein in solution, which based on current technology, is capable of assembly in vitro into a virus-like coat. Based on the crystal structure of the protein it can be recognized that a loop region in the structure near to amino acid position 150 is possibly suitable for the insertion of the WW domain, since this loop region is found on the outside of the coat when assembly of the pentamer protein to a virus-like coat takes place.

The expression and purification of PyVP1-WW150 takes place as fusion protein with a C-terminally fused intein domain and a chitin binding domain (CBD) connecting to that. For this, first of all, a plasmid is constructed based on the vector pCYB2 of the IMPACT-System (New England Biolabs). Through the multiple cloning site of pCYB2, with help of the restriction sites NdeI-XmaI (New England Biolabs), a DNA-fragment, coding for a variant of the VP1 gene of mouse polyoma virus, is amplified by PCR and cloned by standard methods.

As basis for this, a polyoma virus variant is used which displays no cysteines in the sequence whatsoever; the six cysteines of the wild type protein were previously replaced with serine with the help of conventional mutation techniques. This variant of PyVP1 has the advantage that the redox conditions of the solution have no influence on the condition of the protein; it is thereby easily manageable in many applications. Additionally, by the later introduction of a cysteine in the inserted WW domain, a specific disulfide bridge of WW domain and proline-rich sequence can be achieved. As a further variation, a modification to site 249 is used; the threonine found there in the wild-type protein is replaced with cysteine. At this site in the protein, a marking with help of fluorescence dyes is, based on current technology, advantageously possible. The protected localization in the pentamer allows the marking at this site without unwanted side-effects. The variant of polyoma virus VP1 used is correctly named PyVP1-CallS-T249C, subsequently abbreviated with the term PyVP1.

For the PCR, the following oligonucleotides are used as primer: vp1NImp (5'-TAT ACA TAT GGC CCC CAA AAG AAA AAG C-3'; SEQ ID NO:24), and vp1CImp (5'-ATA TCC CGG GAG GAA ATA CAG TCT TTG TTT TTC C-3'; SEQ ID NO:25). With this PCR, the C-terminal amino acids of the wild-type VP1 protein of Gly383-Asn384 are transformed simultaneously into Pro383-Gly384, since a C-terminally localized asparagine is very unfavorable regarding the cleavage characteristics for the intein cleavage system. The point mutations named do not further influence the essential characteristics of the PyVP1 protein. The tac promotor of the pCYB2 vector provides only slight expression quantities of the fusion protein, thus the fusion construction PyVP1-intein-CBD is isolated from the pCYB2 vector through an additional PCR, and cloned in the NdeI-EcoRI sites of a highly-expressing pET-vector with T7lac promotor (plasmid pET21a, Novagen. Oligonucleotide:

```
vp1-NImp
(5'-TAT ACA TAT GGC CCC CAA AAG AAA AAG C-3'),
and

5'-ATA TGA ATT CCA GTC ATT GAA GCT GCC ACA AGG-3'.
```

The cloning of the WW domain as insertion in the external Loop of PyVP1 between the amino acid positions 148 and 149 takes place in several steps. With the oligonucleotides FBP11-WWaN (5'-ATA CTC TTC AGG CAG CGG CTG GAC AGA ACA TAA ATC ACC TGA TGG-3'; SEQ ID NO:27) and FBP11-WWaC (5'-ATA CTC TTC TAC CAC TAC CAT CAT CCG GCT TTT CCC AGG TAG ACT G-3'; SEQ ID NO:28), a PCR is implemented on a DNA-fragment which contains the formin-binding protein 11 (FBP11) from the organism *Mus musculus* (mouse). Among other things, a WW domain is encoded in this gene sequence. The oligonucleotides simultaneously insert a short linker sequence of 5 amino acids apiece, consisting of alternating glycine-serine amino acids. A second PCR on the previously described vector amplifies the N-terminal fragment of PyVP1 between amino acids 1 and 148 with help of the oligonucleotide vp1NImp (see above) and vp1-150-WWaC (5'-ATA CTC TTC AGG TAG CGG CGT AAA CAC AAA AGG AAT TTC CAC TCC AG-3'; SEQ ID NO:29). Finally, a third PCR also amplifies the C-terminal fragment of PyVP1 between amino acids 149 and the C-terminal end of the protein, with help of the oligonucleotide vp1-150-WWaN (5'-ATA CTC TTC AGC CGC TGC CTG TAT CTG TCG GTT TGT TGA ACC CAT G-3'; SEQ ID NO:30) and vp1CImp (see above).

All three PCR products are subsequently digested with type IIS restriction enzyme EamI 104 I (Stratagene). The N-terminal and the C-terminal fragment of PyVP1 (PCR products 2 and 3, see above) are dephosphorylated with help of alkaline phosphatase (CIP, New England Biolabs) to create a gene sequence in the following ligation step from the three prepared PCR-fragments, with the following sequence: (PyVP1-N-terminus)-WW domain fragment-(PyVP1-C-terminus). A PCR afterwards with the oligonucleotides vp1NImp and vp1CImp (see above) amplifies the ligation product of the three fragments, subsequently abbreviated with the term PyVP1-WW150. The PCR product can then be cloned by means of the standard method in the vector pCR-blunt (Invitrogen). After cutting out the cloned fragment PyVP1-WW150 with help of the restriction enzyme Nde 1-Sma, the final cloning in the previously described plasmid pET21a can subsequently take place.

The lastly generated vector allows the expression of the fusion protein (PyVP1-WW150)-intein-CBD with help of highly expressive T7lac promotors in *E. coli* BL21 (DE3) cells (mfr.: Novagen). For this purpose, transformed cells in 5 l.-Erlenmeyer flasks that contain 2 l. LB medium each, are cultivated at 37° C., until the $OD_{600}$ of the culture reaches 2.0 to 2.5. Protein expression is induced by 1 mM IPTG in the medium. The cultures are thereafter incubated at 15° C. for a further 20 hours; the low temperature minimizes the cleavage of the intein part in the fusion protein under in vivo conditions. The cells are harvested by centrifugation, dissolved in 70 ml resuspension buffer (20 mM HEPES, 1 mM EDTA, 100 mM NaCl, 5% (w/v) Glycerol, pH 8.0), and lysed through high pressure homogenization. After centrifugation of the crude extract for 60 min. at 48,000 G, a clear cellular extract is obtained. This extract is applied with a flow rate of 0.5 ml/min at a temperature of 10° C. on a 10 ml chitin affinity column (New England Biolabs). The column is subsequently washed with 3 column volumes of the resuspension buffer, 15 column volumes of a wash buffer with high ionic strength (20 mM HEPES, 1 mM EDTA, 2 M NaCl, 5% (w/v) glycerol, pH 8.0) and again 3 column volumes of the resuspension buffer; thereby all undesirable *E. coli* host proteins are removed from the chitin matrix.

The cleavage of the PyVP1-WW150 monomer from the fusion protein by means of self-cleaving intein activity is induced in resuspension buffer through a pulse (3 column volumes) with respectively 50 mM dithiothreitol (DTT), 50 mM hydroxylamine, or 30 mM DTT along with 30 mM hydroxylamine. For this, the loaded chitin matrix is incubated with one of the indicated solutions for 14 hours at 10° C. The PyVP1-WW150 protein is thereby completely released and can be separated, by means of column chromatographic standard methods, from the chitin matrix and the remaining elements of the fusion protein adhering to the matrix. For that purpose, a linear salt gradient is appropriately used with a concentration between 0.1 and 2.0 M NaCl. The regeneration of the chitin matrix takes place through washing of the chitin material with 3 columns volumes of an SDS-containing buffer (1% SDS (w/v) in resuspension buffer) according to manufacturer's instructions.

The PyVP1-WW150 protein is, in the described process, expressed as a soluble pentamer and is native. FIG. 2a shows an SDS gel with the purified fractions of wild type PyVP1 (or the variant PyVP1-CallS-T249C derived therefrom) and of the PyVP1-WW150 variant, which exhibits a higher mass because of the additionally inserted amino acids. FIG. 2b shows comparable CD spectra of the produced proteins in 10 mM HEPES, 150 mM NaCl, pH 7.2, which exhibit a correct folding of the protein species. A deconvolution of both CD spectra according to current technology shows that in the case of the PyVP1-WW150 domain, an increase in the β-sheet structure can be noted compared to that of the PyVP1 protein. This indicates that the inserted WW domain has kept its native structure as β-sheet.

The example shows that surprisingly, the WW domain can be inserted with correct folding under suitable conditions in loop regions of protein structures, without substantially disturbing their native structure. The PyVP1-WW150 protein, pentameric in solution, contains the native WW domain inserted in the polypeptide chain and presents these, after assembly, on the outside of the virus-like coat (see Example 2).

EXAMPLE 2

Characterization of the Properties of PyVP1-WW150

By means of example 1, a protein (PyVP1-WW150) can be produced which artificially has a WW domain inserted. The binding qualities of PyVP1-WW150 in relation to proline-rich ligands can be characterized with various processes. An advantageous method for this is provided by surface plasmon resonance; in the given example, the instrument Biacore X (Biacore AB) is used. A synthetic peptide of the sequence Cys-Ser-Gly-Pro-Pro-Pro-Pro-Pro-Pro-Pro-Pro-Leu-Pro (SEQ ID NO:15) is coupled, according to manufacturer's instructions via a thiol or amino coupling, to a type CM5 sensor chip. In the process, initially a quantity of 80 resonance units of the indicated peptide (RU) is immobilized on the surface. The following measurements always take place at 25° C. and a flow rate of 20 μl/min.

Binding studies of PyVP1-WW150 at the sensor chip are carried out with immobilized proline-rich peptide under various solvent conditions. The first measurement takes place under standard solvent conditions, with 10 mM HEPES, 1 mM EDTA, 150 mM NaCl, pH 7.2. The protein concentration of PyVP1-WW150 is varied from 5 to 50 nM. In FIG. 3*a*, it is apparent that PyVP1-WW150 binds with high affinity to the sensor chip. The bound quantity is, as expected, proportional to the protein concentration utilized. The binding constant $K_D$ of the PyVP1-WW150 protein is determined thereby to have a value of 5 nM (FIG. 3*a*). As is furthermore obvious from the figure, the binding is not lasting, but the protein dissociates again in a slow process after the loading of the sensor's surface. This shows that the interaction of the interaction partners is reversible.

To test the binding under conditions of physiological ionic strength, Dulbecco's PBS (Gibco) is used as solvent for the second measurement. The remaining experimental conditions are selected analogously to the first experiment previously described. FIG. 3*b* demonstrates that binding of the PyVP1-WW150 with Dulbecco's PBS displays no significant differences compared to binding under standard conditions (FIG. 3*a*). From the experiment, binding parameters can be derived for the association ($K_{on}$=2105 $M^{-1}s^{-1}$) and dissociation ($K_{off}$=1.810$^{-3}$ $s^{-1}$). The example shows that the changed solvent conditions have no substantial influence on the binding of PyVP1-WW150 to the proline-rich peptide, and suggests that the interaction of both partners also takes place stably under physiological conditions. Thus, a fundamental applicability of the system under clinical conditions within the realms of diagnostics or therapeutics is also possible.

For determination of the specificity of the binding, Dulbecco's MEM medium with 10% FCS (fetal calf serum, Gibco) is used as running buffer in a third measurement. FCS here represents a model system for a mixture of different proteins and other substances that are relevant in biological systems. FIG. 3*c* shows that also under these conditions a significant and specific binding of the PyVP1-WW150 protein is to be noted at the sensor's surface. As in both previously described measurements, the response signal at the sensor's surface is here also proportional to the concentration of PyVP1-WW150 protein introduced. Therewith, it is shown that the interaction of PyVP1-WW150 with the immobilized proline-rich peptide is independent of the presence of a mixture of other substances, as for instance occurs in serum.

In summary, these three analyses, with help of Biacore technology and a sensor surface with immobilized proline-rich peptide, show that binding between molecular substances that contain a WW domain and proline-rich ligands takes place with high affinity and specificity. The interaction is thereby reversible and not essentially dependent on the chosen solvent conditions. The dissociation takes place relatively slowly compared to the association; the dissociation constant lies at 20 nM.

EXAMPLE 3

Immobilization on a Matrix

A further method for the characterization of binding qualities is a reversible immobilization of the WW domain on an inert matrix. For this, a synthetic proline-rich peptide (sequence Cys-Ser-Gly-Pro-Pro-Pro-Pro-Pro-Pro-Pro-Pro-Leu-Pro; SEQ ID NO:15) is connected through a thiol coupling to SulfoLink column material (Pierce) according to manufacturer's instructions. A chromatography column is packed with the matrix modified in this way. This permits a loading of the samples on the matrix and elution with bound proteins under different conditions. The PyVP1-WW150 protein purified as in example 1 is applied to the column (solvent 10 mM HEPES, 1 mM EDTA, 150 mM NaCl, 5% Glycerin, pH 7.2). As evident from FIG. 4, the protein binds to the matrix and appears only in slight quantities in the wash fractions. A subsequent elution of the protein from the matrix is possible through addition of 1% SDS or 300 mM arginine to the running buffer.

This experiment shows that the PyVP1-WW150 protein is able to reversibly bind to a matrix that carries a proline-rich peptide. An temporary immobilization can thereby take place. A detachment of the protein from the matrix is possible through use of additives in the running buffer.

EXAMPLE 4

Binding of a Proline-Rich Peptide to a Capsid

In a further experiment, the binding of a fluorescence-marked peptide with a proline-rich sequence to the surface (exterior) of virus-like capsids is explored. The assembly of the protein takes place in analogy to conditions already described, based on current technology (see Salunke, Caspar & Garcea, Polymorphism in the assembly of polyoma virus capsid protein VP1, *Biophys. J.* 56, pp. 887-900, 1989). The virus-like capsids are obtained after dialysis of the protein against 10 mM HEPES, 50 mM NaCl, 0,5 mM $CaCl_2$, 5% Glycerin, pH 7.2. The proline-rich peptide Cys-Ser-Gly-Pro-Pro-Pro-Pro-Pro-Pro-Pro-Leu-Pro (SEQ ID NO:15) is labeled specifically at the N-terminal cysteine with a fluorescein-maleimide derivative (Molecular Probes) according to manufacturer's instructions. After the assembly into capsids of the virus protein variants, a tenfold molar excess of fluorescence-marked peptide is added. Through gel filtration (column TSKGel G5000PWXL, TosoHaas), virus-like capsid coats can be clearly detected and separated from free, non-assembled capsid elements as well as from surplus peptide and fluorescence dye. The peptide bound to the WW domain located on the surface of the capsid elutes in the capsid fractions and can be verified through the specific absorption of the fluorescence dye (FIG. 5).

This example shows that the PyVP1-WW150 variant can form capsid structures (virus-like coats) under suitable conditions. These capsids are able to bind proline-rich peptide. Thus, molecular substances can be brought in a directed manner to the surface (exterior) of virus-like structures via the specific and strong interaction of WW domain and proline-rich sequence.

EXAMPLE 5

Packaging of GFP in the Interior of a Virus-Like Protein Coat

In this example, it is shown that through favorable positioning of adapter segments, a localization of molecular substances into the interior of viral coats, or of virus-like coats (capsids) can take place. Due to the three-dimensional structure of polyoma virus VP1 it is known, based on current technology, that the N-terminus of the protein is localized in the interior of the coat after assembly into the capsid. The first 14 amino acids of the protein are thereby possibly unnecessary, since they can not be detected in the x-ray structure of the capsids. Hence two different variants of the PyVP1 protein are produced, which contain a WW domain at the amino terminus of the native wild-type protein (variant PyVP1-3C-WW1) or carry the WW domain at an N-terminus shortened by 14 amino acids (variant PyVP1-3C-WW[N-14]), as well as a variant of the PyVP1 protein which carries a proline-rich sequence at the N-terminus (PyVP1-3C-[N-14]-PLP). The basis for these variants is a PyVP1 variant which contains the cysteines C19 and C114, and in which a specific new cysteine is additionally introduced (analogous to the variant PyVP1-CallS-T249C). This variant is hereafter abbreviated with PyVP1-3C.

First of all, an amplification of the WW domain is performed by means of PCR; the FBP11 gene of the mouse serves thereby as a template, analogous to example 1. As oligonucleotide for the PCR, 5'-AAT ATA TCA TAT GTC CAT CAT CCG GCT TTT CCC AGG TAG ACT-3' (SEQ ID NO:31) (with NdeI interface), and 5'-TAT TAA TCA TAT GAG CGG CTG GAC AGA ACA TAA ATC ACC TGA TGG-3' (SEQ ID NO:32) are thereby used. The PCR product obtained is subsequently cloned, through the cutting sites Nde I-Nde I introduced by means of the oligonucleotide, into the expression vector pET21a from example 1, which contains the gene for a fusion protein PyVP1-intein-CBD; at that 5' end of the gene, a singular Nde I restriction site is found. The expressed gene product of this vector is the desired protein PyVP1-3C-WW1. Analogous thereto, cloning with a fragment of PyVP1-3C shortened by 14 amino acids (PyVP1-3C-WW[N-14]) is performed based on the standard method described in example 1. To this end, a PCR is performed on the PyVP1 genetic fragment, with 5'-GCG CGC GCA TAT GAG CAC CAA GGC TAG CCC AAG ACC CG-3' (SEQ ID NO:33) and the oligonucleotide vp1CImp (see Example 1). The PCR product that results is digested with the restriction enzymes Nde I-Sma I, and the fragment cloned into the vector pET21a from example 1 using the standard method. Expression and purification of both proteins takes place in accordance with example 1. The purified proteins are compared to the variants PyVP1 and PyVP1-WW150 in FIG. 6*a*. It shows that the proteins are soluble and natively producible. The change of the N-terminus through the introduction of the WW domains has no important negative influence on the assembly competence of the protein for the creation of virus-like shell structures.

In an analogous manner, the manufacture and purification of a GFP variant is undertaken. GFP is a protein that displays a green fluorescence (absorption maximum at 490 nm) in the native condition. It is excellently suited for the marking of complexes and assemblies. For the manufacture of a GFP variant with a proline-rich terminal sequence, a PCR-based amplification of the GFP gene first of all is carried out, with the plasmid pEGFP-N1 (Clontech) serving as template. Simultaneously, suitable restriction sites are introduced into the PCR product. The PCR takes place by means of the oligonucleotides 5'-TTA TTT ACA TAT GGT GAG CAA GGG CGA GGA G-3' (SEQ ID NO:34) (with Nde I-cutting site) and 5'-ATA TCT TAA GTA CAG CTC GTC CAT GCC G-3' (SEQ ID NO:35) (with AflII cutting site). The PCR product so obtained is cloned, over the restriction site, into the vector pTIP and expressed there. This vector pTIP is a derivative of the intein purification vector documented in example 1, on basis of pET21a, with additionally introduced proline-rich sequences. The vector is constructed so that a proline-rich sequence can be selectively fused to the 5' or 3' ends of a gene integrated in a multiple cloning site. The proline-rich sequence thereby contains mainly Pro-Pro-Pro-Pro-Pro-Pro-Pro-Pro-Leu-Pro (SEQ ID NO:36). The manufacture and purification of the GFP-PLP protein takes place by means of chitin affinity chromatography, in accordance with the method in example 1. The successful manufacture and purification of GFP-PLP is documented in FIG. 6*b*. The GFP-PLP protein, which carries the proline-rich sequence Pro-Pro-Pro-Pro-Pro-Pro-Pro-Pro-Leu-Pro (SEQ ID NO:36) at the C-terminus, can be produced in solution in large quantity. The green luminous color of the protein solution simultaneously shows that the protein can fold to its native structure.

The manufacture of the Py-VP1-3C-PLP variant takes place analogously. For manufacture of this PyVP1 variant, PyVP1-3C-[N-14] is cloned into the vector pTIP, so that the the proline-rich sequence contained in the vector is fused N-terminally to the Py-VP1-3C-[N-14].

For inspection of the functional characteristics of both PyVP1 variants with WW domain at the respective N-terminus of the proteins, both variants are incubated with proteins that contain proline-rich sequences. The PyVP1-3C-WW1 protein is incubated with the prior-produced protein GFP-PLP (molar relationship 1:6) for 10 min. (10 mM HEPES, 1 mM EDTA, 150 mM NaCl, 5% Glycerol, pH 7.2), and the capsid formation of the PyVP1 variants induced through dialysis against a buffer which contains 0.5 mM $CaCl_2$ (see Example 4). The successful detection of capsids (FIG. 7*a*) demonstrates that the variant PyVP1-3C-WW1 is competent for assembly under suitable conditions. Using gel filtration assays (column TSKGel G6000PWXL, TosoHaas), it can be shown that a slight portion of the native GFP-PLP protein (identifiable by the specific absorption of 490 nm) is contained in the capsid fraction (at elution volumes between 9 and 10 ml) (FIG. 7*a*). That means that during the incubation of GFP-PLP protein with the PyVP1-3C-WW[N-14] variant a binding of both proteins to one another takes place, whereby the GFP was directed into the interior the virus-like of particle during the subsequent capsid assembly.

EXAMPLE 6

Packing of a Peptide in the Interior of a Virus-Like Protein Coat

In a second experiment analogous to experiment 5, PyVP1-3C-WW[N-14] is incubated in a molar relationship of 1:10 with a proline-rich peptide that was previously fluorescence-labelled. The labeling of the peptide (Cys-Ser-Gly-Pro-Pro-Pro-Pro-Pro-Pro-Pro-Pro-Leu-Pro; SEQ ID NO:15) here takes place by means of fluorescein maleimide (Molecular Probes) through a maleimide coupling of the dye to the N-terminal cysteine, according to manufacturer's instructions. Again, as in the example 5, it is shown that after assembly of the PyVP1-3C-WW[N-14] variant, PyVP1-3C-WW[N-14] is competent for assembly under suitable conditions. In addition, the protein is able to bind the proline-rich peptide and, during the assembly into a protein coat, to bring the proline-rich peptide into the interior of the capsid. This is shown with the gel filtration in FIG. 7*b* through the specific absorption at 490 nm of the fluorescence dye bound to the peptide covalently, which is found mainly in the elution region of the capsid (9 to 10 ml).

Moreover, using the variants of PyVP1-3C-[N-14]-PLP (proline-rich sequence at the N-terminus) and GFP-WW1 (WW domain at the N-terminus), an analogous assembly attempt can be carried out. This shows that a reciprocal disposition of WW domain and proline-rich ligands at the substances to be joined, that is, the placement of proline-rich sequence on the polyoma core protein (capsid) and the WW domain on the protein to be wrapped, also leads to a successful targeting of GFP into the interior of the virus-like coat.

Summing up, the experiments in examples 5 and 6 show that variants of PyVP1 with WW domain fused to the N-terminal are able to bind proline-rich sequences and to conduct these, as well as any molecular substances located on them, under suitable conditions into the interior of virus-like coats during assembly into capsids. The described process is thereby suitable to cause a directed wrapping of molecular substances in viruses or in virus-like capsids. It could likewise be shown that variants of PyVP1 with a proline-rich sequence fused to the N-terminal are able to bind WW domains and molecular substances located on them.

EXAMPLE 7

Disulfide Bridging for Covalent Linkage on the Basis of Modified WW Domains and Proline-Rich Peptides The investigations described in the previous examples 1 to 6 show that through the interaction of WW domain with a proline-rich peptide sequence, a temporally limited aggregation of both adapter segments can occur. A permanent bridging of interaction partners can be achieved by equipping both adapter segments with specifically-introduced cysteine amino acids, which allow, with suitable positioning, disulfide bridging after the association of the binding partners.

Through point mutations, performed in accordance with conventional processes based on current technology, individual amino acids that are not essential for the association of both adapter segments can be changed to cysteines, both within the WW domain as well as in the proline-rich sequences of the ligands. Under suitable redox (oxidizing) conditions, a specific disulfide bridging can be formed between the bound proline-rich ligands and the WW domain, each containing one or more cysteines. This bridging is thereby decisively favored through the interaction of WW domain and the ligands. The temporally limited interaction between unconnected WW domain and proline-rich ligands lasts long enough to form a covalent linkage through disulfide bridging. The interaction of both adapter segments becomes, in this way, temporally unlimited, since disulfide bridges under physiological conditions, as they exist for instance in extracellular space, are stable. If desired, the disulfide bridge between WW domain and proline-rich ligands can be eliminated again in vitro, under reducing conditions (for instance 50 mM DTT, DTE or -Mercaptoethanol); by removal of the reducing agent, a reconnection is also possible.

Based upon the variant PyVP1-WW150 of the core protein VP1 of murine polyoma virus, an aspartate amino acid (position 8 into the WW domain) is transformed through mutagenesis into a cysteine. The resulting cysteine-containing variant is subsequently named PyVP1-WW150-D8C. Through binding studies based on surface plasmon resonance, it can be shown that this variant of the WW domain binds the proline-rich ligands Cys-Ser-Gly-Pro-Pro-Pro-Pro-Pro-Pro-Pro-Pro-Leu-Pro (SEQ ID NO:15), even without creation of disulfide bridging. The extent of the interaction is, however, somewhat slighter than with PyVP1-WW150. This can evidently be ascribed to the newly introduced cysteine. It can be shown that this accumulation can be strengthened through addition of 500 mM ammonium sulfate. Thereby, the hydrophobic interactions between proline-rich ligands and WW domain are presumably intensified. The intensity of the interaction can thus be modulated through the ammonium sulfate concentration in the solvent.

The formation of the disulfide bridge between proline-rich ligands and WW domain subsequently takes place under slightly oxidizing conditions. For this purpose a buffer is used which both contains ammonium sulfate and maintains defined redox conditions. The latter conditions are achieved through usage of 1 mM GSSG and 5 mM GSH in the redox buffer (50 mM Tris, pH 8.5, 1 mM EDTA, 500 mM ammonium sulfate); oxidized (GSSG) or reduced glutathione (GSH) functions thereby as a redox shuffling system for the formation of disulfide bridges (see R. Rudolph, In vitro folding of inclusion body proteins, *FASEB J.* 10, 49-56, 1996). The disulfide bridging is carried out at 15° C. for 24 h and completed through dialysis against 50 mM Tris, 1 mM EDTA, pH 7. Under the conditions mentioned last, no further disulfide exchange occurs; the formed disulfide bridges are stable.

Summing up, it can be said that the introduction of cysteine amino acid residues into the WW domain make possible the covalent bridging of polyproline-rich ligands which carry at least one cysteine, with the WW domain and thereby lead to a stable covalent linkage of WW domain and ligand (see FIG. 9).

EXAMPLE 8

Purifying of Proteins by Means of Adapter Segments (Polyproline/WW-Affinity Chromatography)

A further area of application of the invention at hand is the separation of molecular substances from mixed substances, as is typically done in the purification of proteins from crude extracts (cellular extracts). In the process, the affinity of the WW domain to proline-rich ligands is exploited to isolate proteins that contain a WW domain from a complex mixture (crude extract) of proteins (principle of affinity chromatography). For this purpose, a column is used as in example 3; the SulfoLink material (Pierce, the reactivity of the matrix with SH groups is based on the iodacetamide group at the end of a linker, consisting of 10 $CH_2$-groups) is thereby loaded through a thiol coupling with the peptide Cys-Ser-Gly-Pro-Pro-Pro-Pro-Pro-Pro-Pro-Leu-Pro (SEQ ID NO:15), according to manufacturer's instructions.

Analogously, the coupling of peptides to other matrices is possible, for instance AffiGel 10 (Biorad, the reactivity of the matrix with $NH_2$ groups is based on the N-hydroxysuccinimide group at the end of a linker, consisting of 10 $CH_2$-groups) through the N-terminus of the peptide. Likewise, the peptide coupling can take place at the N-terminus of the peptide to a matrix based on CH-sepharose 4B, (Sigma, the reactive group of the matrix is likewise an N-hydroxysuccinimide ester). A covalent binding of the proline-rich ligands to a carrier material also results here, which subsequently allows a purification of WW domain proteins.

The PyVP1 variant PyVP1-3C-WW1 from example 5 (WW domain at the N-terminus of the PyVP1 protein) is, analogous to the specifications from example 1, produced as a fusion protein with an intein and a chitin-binding domain ([PyVP1-3C-WW1]-intein-CBD). It is not, however, purified with the described standard method, by means of chitin-affinity chromatography. Instead, the cellular extract, after cellular breakdown and subsequent centrifugation, is applied to the previously-described column. 10 mM HEPES, 150 mM NaCl, 1 mM EDTA, 5% Glycerin, pH 8.0 serve thereby as running buffer. After application of the extract, it is washed with 10 column volumes of a buffer which contains 10 mM HEPES (pH 8.0), 1 mM EDTA, 5% Glycerin, and in addition 2 M NaCl. With this wash procedure, all non-specific adsorbed proteins and cellular components are removed from the SulfoLink matrix. Afterwards, elution of the bound fusion protein [PyVP1-3C-WW1]-intein-CBD takes place with a buffer which contains 2% SDS. As can be recognized in FIG. 8, a binding of the fusion protein [PyVP1-3C-WW1]-intein-CBD takes place through the interaction of the WW domain with the immobilized proline-rich peptide in the SulfoLink matrix. The fusion protein is thereby bound to the matrix and thus most of the other proteins of the cellular extract are removed in flow-through or during the wash process. Subsequently, the elution with SDS almost exclusively delivers the complete WW domain-containing fusion protein, as well as proteolytic degradation products thereof (which in the case of PyVP1, appear in all comparable manufacture processes based on current technology) and molecular chaperones, which, as is commonly known, are able to bind directly to PyVP1 and cannot usually be separated. Instead of elution of the bound WW domain protein by means of SDS, an elution of native protein with 300 mM arginine in the running buffer is also possible. Through subsequent dialysis of the eluate for removal of the arginine, one receives the purified, native protein.

In summary, this example shows that with the described system it is possible to separate and purify specific molecules from a mixture of substances (crude extract).

EXAMPLE 9

Specific Dimerization of Molecules Through Adapter Segments

Using the interaction of adapter segments (WW domain and proline-rich peptide), the manufacture of bifunctional or bivalent hybrid molecules in vitro can also take place. To that end, two molecular substances are produced which, according to application, can have identical or different characteristics, and each of which always carries one of the adapter segments covalently linked. In the chosen example, the manufacture of easily-detectable dimers of the GFP protein is performed.

A variant of GFP is produced for this purpose, analogous to the production of PyVP1 and with help of the intein-based expression system from example 1, with a WW domain at the N-terminus of the GFP (GFP-WW1). First of all, a PCR on the vector pEGFP-N1 (Clontech, see Example 5) is implemented with the oligonucleotides 5'-TAT AGC TAG CGT GAG CAA GGG CGA GGA GCT GTT C-3' (SEQ ID NO:37) and 5'-GGG AAT TAA GTA CAG CTC GTC CAT GCC G-3' (SEQ ID NO:38). The PCR product is ligated through the cutting sites Nhe I-Sma I into the vector pET21a from example 5, which, at the 3' end of the insertion site, contains the fusion protein of intein and chitin binding domain (CBD) described in example 1. On the 5'-side of the insertion site, the WW domain that is described in example 5 is found. Thus, a fusion product is made with the sequence WW domain-GFP-intein-CBD. The plasmid that encodes the fusion protein can be transformed into the *E. coli* strain BL21 (DE3). Analogous to examples 1 and 3, the manufacture and purification of fusion proteins can then take place. With the described process, the protein GFP-WW1 can be produced in purified form.

A second variant of GFP is produced analogously to this, with a proline-rich segment (Pro-Pro-Pro-Pro-Pro-Pro-Pro-Pro-Leu-Pro; SEQ ID NO:36) at the C-terminus. The manufacture and purification of the GFP-PLP protein thereby takes place identically to the description for the protein in example 5.

Both GFP variants are subsequently incubated together. Both proteins are thereby brought into connection with each other through the adapter segments and as a result a GFP dimer is formed that can be distinguished from the GFP monomer through gel filtration in a TSK-PW2000XL gel filtration column (TosoHaas).

The example demonstrates that with help of the procedure described in the invention at hand, a connection of arbitrary molecular substances can take place, which carry appropriate adapter segments on the basis of WW domains or proline-rich peptide segments. Homofunctional or heterofunctional assemblies can thereby be formed.

EXAMPLE 10

Packaging of WW Domain Containing Peptides into the Interior of a Virus-Like Shell In this example it is shown that a direct packaging of proteins (GFP-WW1) which contains a WW domain can be achieved by positioning a proline-rich sequence at a protein shell. This example therefore shows in a mirror fashion to the elaborately documented example 5 in this patent application that the WW domains rsp. proline-rich sequences used as anchoring molecules are interchangeable. The result of this experiment was already represented in a short form in the patent application (FIG. 7b, and figure legend to FIG. 7 in the patent application).

For the production of the expression plasmid for the GFP-WW1 fusion protein the vector pyVP1-3C-WW1 described in example 5 in the patent application is used, which contains a NheI restriction site in the VP1 gene close to the 5' end. The GFP gene was amplified by PCR using the oligonucleotides 5'-TAT AGC TAG CGT GAG CAA GGG CGA GGA GCT GTT C-3'(NheI) and 5'-GGG AAT TAA GTA CAG CTC GTC CAT GCC G-3'(SmaI), thereby introducing a NheI cutting site at the 5' end and a SmaI cutting site at the 3' end. The VP1 gene in the vector pyVP1-3C-WW1 is replaced by the GFP gene, thereby creating an open reading frame for the fusion protein GFP-WW1.

In an analogous way, the production of the VP1 coat protein with an N-terminally fused proline-rich sequence is performed. First, the VP1 gene from the vector pyVP1-3C-WW1 is amplified using PCR, whereby an AflIII restriction site is introduced by the oligonucleotide 5'-TAT ACT TAA GTA CAA AGG CTT GTC CAA GAC CCG C-3' and an EcoRI restriction site is introduced using the oligonucleotide 5'-ATA TGA ATT CCA GTC ATT GAA GCT GCC ACA AGG-3'. Subsequently, the VP1 gene is inserted into the vector pTIP described in example 5 of the patent application which results in an N-terminal fusion of the proline-rich sequence to VP1.

The production and purification of the fusion proteins described before occurs by chitin affinity chromatography in analogy to the procedure described in example 1 of the patent application.

In order to check the functional properties of the two proteins, they are incubated together and the association of the proteins via their adapters is analyzed using gel filtration chromatography. For this, the GFP-WW protein is added in a fivefold molar excess to the VP1-3C-PLP protein and subsequently incubated for 10 min in a buffer in which the VP1 is contained in its pentameric form, and therefore the accessibility of the adapters is ensured (pentamer buffer 10 mM HEPES, 1 mM EDTA, 150 mM NaCl, 5% Glycerol). Subsequently, the capsid formation is induced by addition of 0.5 mM CaCl2. Gel filtration analysis (column TSK Gel G6000PWXL) demonstrate that the VP1-3C-PLP variant is assembly competent under suitable conditions. In addition, it is demonstrated that GFP-WW1 is contained in the capsid fraction (FIG. 7b of the patent application). Therefore, during the incubation over 10 minutes described before, an association between the GFP-WW1 and the VP1-3C-PLP protein has occurred by their adapters, so that the GFP-WW1 was directed directly into the interior of the virus-like particles during the following capsid formation.

The example shows therefore that WW domain and proline-rich sequence can be introduced in different molecular environments, respectively, and the molecular substances modified in this way can so be linked together. Additionally, in the present special case of this example one of the molecular substances is an assembly-competent capsid, so that moreover a direction of the molecular substance into a protein shell was possible.

The invention claimed is:

1. Method for linking of two or more molecular substances with each other through adapter segments, said method comprising:
   (a) modifying one of the molecular substances in such a way that it exhibits as an adapter segment, in at least one region, a WW domain,
   (b) modifying another molecular substance in such a way that it exhibits as an adapter segment, in at least one region, a proline-rich sequence, which binds to the WW domain, and
   (c) forming a covalent bond between the molecular substances by interaction between said WW domain and said proline-rich sequence, wherein said molecular substances are members selected from the group consisting of antibodies, substances analogous to antibodies, enzymes, structural proteins, peptide antibiotics, isolated structure-forming, catalytic, or regulatory protein domains, fragments or proteins, peptides, peptide analogs, antigen-bearing substances, glucoproteins, lipoproteins, and proteoglycans.

2. Method for linking of two or more molecular substances with each other through adapter segments, said method comprising:
   (a) modifying one of the molecular substances in such a way that it exhibits as an adapter segment, in at least one region, a WW domain,
   (b) modifying another molecular substance in such a way that it exhibits as an adapter segment, in at least one region, a proline-rich sequence, which binds to the WW domain, and
   (c) introducing one or several cysteines in the region of the WW domain and one or more cysteines in the region of the proline-rich sequence, and forming a covalent link between said molecular substances at said cysteines, wherein said molecular substances are members selected from the group consisting of antibodies, substances analogous to antibodies, enzymes, structural proteins, peptide antibiotics, isolated structure-forming, catalytic, or regulatory protein domains, fragments or proteins, peptides, peptide analogs, antigen-bearing substances, glucoproteins, lipoproteins, and proteoglycans.

3. Method according to claim 1 or 2, wherein one of the molecular substances is a solid phase matrix molecule.

4. Method according to claim 1 or 2, wherein the WW domain is found in a loop region of a protein structure so modified or a C- or N-terminus of a protein or peptide structure so modified.

5. Method according to claim 1 or 2, wherein the proline-rich sequence is found in a loop region of a protein structure so modified or a C- or N-terminus of a protein or peptide structure so modified.

* * * * *